US011737872B2

(12) United States Patent
Fung et al.

(10) Patent No.: US 11,737,872 B2
(45) Date of Patent: Aug. 29, 2023

(54) VENTRICULAR DEPLOYMENT OF A TRANSCATHETER MITRAL VALVE PROSTHESIS

(71) Applicant: Neovasc Tiara Inc., Richmond (CA)

(72) Inventors: Eric Soun-Sang Fung, Vancouver (CA); Kathleen Hung, New Westminster (CA); Karen Tsoek-Ji Wong, Richmond (CA); David Andrew Moffatt, Richmond (CA)

(73) Assignee: Neovasc Tiara Inc., Richmond (CA)

( * ) Notice: Subject to any disclaimer, the term of this patent is extended or adjusted under 35 U.S.C. 154(b) by 657 days.

(21) Appl. No.: 16/678,364

(22) Filed: Nov. 8, 2019

(65) Prior Publication Data

US 2020/0146814 A1 May 14, 2020

Related U.S. Application Data

(60) Provisional application No. 62/757,462, filed on Nov. 8, 2018.

(51) Int. Cl.
*A61F 2/24* (2006.01)

(52) U.S. Cl.
CPC ............ *A61F 2/243* (2013.01); *A61F 2/2418* (2013.01); *A61F 2/2436* (2013.01); *A61F 2220/0008* (2013.01)

(58) Field of Classification Search
CPC ....... A61F 2/243; A61F 2/2436; A61F 2/2418
See application file for complete search history.

(56) References Cited

U.S. PATENT DOCUMENTS

| | | | |
|---|---|---|---|
| 2,967,856 A | 1/1961 | Coover, Jr. et al. | |
| 6,629,534 B1 | 10/2003 | Goar et al. | |
| 8,449,599 B2 * | 5/2013 | Chau | A61F 2/246 623/1.26 |
| 8,579,964 B2 | 11/2013 | Lane et al. | |
| 9,125,738 B2 | 9/2015 | Figulla et al. | |

(Continued)

FOREIGN PATENT DOCUMENTS

| | | |
|---|---|---|
| AU | 2019374743 B2 | 3/2022 |
| CA | 2874219 C | 7/2020 |

(Continued)

OTHER PUBLICATIONS

"International Application Serial No. PCT/CA2019/051598, International Preliminary Report on Patentability dated May 20, 2021", 8 pgs.

(Continued)

*Primary Examiner* — Brian A Dukert
(74) *Attorney, Agent, or Firm* — Schwegman Lundberg & Woessner, P.A.

(57) ABSTRACT

A method of delivering a prosthetic valve to a native mitral valve of patient's heart may include providing a radially expandable prosthetic mitral valve which has an upstream atrial portion, a downstream ventricular portion and an annular region therebetween. A constraint is removed from the ventricular portion thereby allowing radial expansion of a ventricular portion. A first anchoring tab on the ventricular portion is radially expanded and an annular region is radially expanded. An atrial skirt on the atrial flange is radially expanded after radial expansion of the ventricular portion.

30 Claims, 65 Drawing Sheets

(56) References Cited

U.S. PATENT DOCUMENTS

2006/0241745 A1 10/2006 Solem
2007/0016286 A1 1/2007 Herrmann et al.
2011/0015731 A1 1/2011 Carpentier et al.
2011/0319989 A1 12/2011 Lane et al.
2013/0075215 A1 3/2013 Saito et al.
2013/0211508 A1* 8/2013 Lane .................... A61F 2/2412 623/2.11
2013/0231735 A1 9/2013 Deem et al.
2014/0379074 A1* 12/2014 Spence ................. A61F 2/2427 623/2.11
2015/0238315 A1* 8/2015 Rabito .................. A61F 2/2436 623/2.11
2016/0051362 A1* 2/2016 Cooper ................. A61F 2/2418 623/2.18
2017/0165064 A1* 6/2017 Nyuli ................ A61M 25/0054
2018/0116790 A1 5/2018 Ratz et al.

FOREIGN PATENT DOCUMENTS

CN 113271890 A 8/2021
DE 10103955 B4 11/2001
DE 10033858 B4 1/2002
DE 102005052628 A1 5/2007
DE 102006052564 B3 12/2007
DE 102006013113 B4 12/2008
DE 102008015781 B4 9/2011
DE 102010051632 B4 9/2013
DE 102005032974 B4 11/2013
DE 102005052628 B4 6/2014
DE 10301026 B4 10/2014
DE 212013000104 U1 11/2014
DE 102008012438 B4 12/2014
DE 102011107551 B4 5/2015
DE 102011054176 B4 2/2016
DE 102014114762 B3 3/2016
DE 102013208038 B4 9/2016
DE 102010012677 B4 8/2017
DE 202011110951 U1 10/2017
DE 202011110985 U1 12/2017
DE 202016105963 U1 1/2018
DE 10394350 B4 5/2018
DE 102009024648 B4 5/2018
DE 102015206098 B4 9/2018
DE 10065824 B4 10/2018
DE 202017104793 U1 11/2018
DE 102011106928 B4 2/2019
DE 202016008737 U1 4/2019
DE 102013205519 B4 5/2019
DE 102008014730 B4 7/2019
DE 102018102940 B4 10/2019
DE 102009009158 B4 11/2020
EP 1077072 B1 11/2003
EP 1140244 B1 11/2003
EP 1214106 B1 11/2003
EP 1562522 B1 12/2003
EP 1143864 B1 2/2004
EP 1220651 B1 3/2004
EP 1265534 B1 6/2004
EP 1347785 B1 7/2004
EP 1245202 B1 8/2004
EP 1161204 B1 9/2004
EP 1266641 B1 10/2004
EP 1102567 B1 11/2004
EP 1117446 B1 11/2004
EP 1107710 B1 12/2004
EP 1121070 B1 12/2004
EP 1217966 B1 12/2004
EP 1233731 B1 12/2004
EP 1294318 B1 12/2004
EP 1237510 B1 1/2005
EP 1034753 B1 2/2005
EP 1259194 B1 2/2005
EP 1121069 B1 3/2005
EP 1143879 B1 3/2005
EP 1023879 B1 4/2005
EP 1112043 B1 4/2005
EP 1339356 B1 4/2005
EP 1214022 B1 5/2005
EP 1318774 B1 5/2005
EP 1088529 B1 6/2005
EP 1171060 B1 6/2005
EP 1251803 B1 6/2005
EP 1259776 B1 6/2005
EP 1272123 B1 6/2005
EP 1049422 B1 7/2005
EP 1230901 B1 8/2005
EP 1335883 B1 8/2005
EP 1307246 B1 9/2005
EP 1267753 B1 10/2005
EP 1284688 B1 10/2005
EP 1343536 B1 10/2005
EP 1027020 B1 11/2005
EP 1152780 B1 11/2005
EP 1171059 B1 11/2005
EP 1237508 B1 11/2005
EP 1303234 B1 11/2005
EP 1328215 B1 11/2005
EP 1341487 B1 11/2005
EP 1392197 B1 11/2005
EP 1469797 B1 11/2005
EP 1255505 B1 12/2005
EP 1360942 B1 12/2005
EP 1322260 B1 1/2006
EP 1359870 B1 1/2006
EP 1237586 B1 2/2006
EP 1309360 B1 4/2006
EP 1322259 B1 5/2006
EP 1124592 B1 6/2006
EP 1237516 B1 6/2006
EP 1098673 B1 7/2006
EP 1124591 B1 7/2006
EP 1083845 B1 8/2006
EP 1155666 B1 8/2006
EP 1463462 B1 8/2006
EP 1684671 A1 8/2006
EP 1519695 B1 9/2006
EP 1444993 B1 10/2006
EP 1117350 B1 11/2006
EP 1212011 B1 11/2006
EP 1261294 B1 11/2006
EP 1318775 B1 11/2006
EP 1429690 B1 11/2006
EP 1173111 B1 12/2006
EP 1239795 B1 12/2006
EP 1299049 B1 12/2006
EP 1487382 B1 12/2006
EP 1112044 B1 1/2007
EP 1482997 B1 1/2007
EP 1117352 B1 2/2007
EP 1128849 B1 2/2007
EP 1392666 B1 2/2007
EP 1474077 B1 2/2007
EP 1225948 B1 3/2007
EP 1251805 B1 3/2007
EP 1117334 B1 4/2007
EP 1263484 B1 5/2007
EP 1313410 B1 5/2007
EP 1370200 B1 5/2007
EP 1560526 B1 6/2007
EP 1173117 B1 7/2007
EP 1434615 B1 7/2007
EP 1465546 B1 7/2007
EP 1499366 B1 7/2007
EP 1819304 A2 8/2007
EP 1519962 B1 9/2007
EP 1337285 B1 10/2007
EP 1112042 B1 11/2007
EP 1148821 B1 11/2007
EP 1143882 B1 12/2007
EP 1330189 B1 12/2007
EP 1489996 B1 12/2007
EP 1296618 B1 1/2008
EP 1401356 B1 1/2008

(56) References Cited

FOREIGN PATENT DOCUMENTS

EP 1629795 B1 1/2008
EP 1128786 B1 2/2008
EP 1616532 B1 2/2008
EP 1289447 B1 3/2008
EP 1895942 A2 3/2008
EP 1115353 B1 5/2008
EP 1330190 B1 5/2008
EP 1383448 B1 6/2008
EP 1251804 B1 7/2008
EP 1294310 B1 7/2008
EP 1313409 B1 7/2008
EP 1395202 B1 7/2008
EP 1395204 B1 7/2008
EP 1395205 B1 7/2008
EP 1423066 B1 7/2008
EP 1560545 B1 7/2008
EP 1605871 B1 7/2008
EP 1671608 B1 7/2008
EP 1690515 B1 7/2008
EP 1180987 B1 8/2008
EP 1337386 B1 8/2008
EP 1492579 B1 9/2008
EP 1524942 B1 9/2008
EP 1627091 B1 9/2008
EP 1827577 B1 9/2008
EP 1259195 B1 10/2008
EP 1704834 B1 10/2008
EP 1146835 B1 11/2008
EP 1498086 B1 11/2008
EP 1622548 B1 11/2008
EP 1235537 B1 12/2008
EP 1237509 B1 12/2008
EP 1355590 B1 12/2008
EP 1455680 B1 12/2008
EP 1472995 B1 12/2008
EP 1513474 B1 12/2008
EP 1620042 B1 12/2008
EP 1690514 B1 12/2008
EP 1258232 B1 1/2009
EP 1420723 B1 1/2009
EP 1570809 B1 1/2009
EP 1395182 B1 2/2009
EP 1408882 B1 2/2009
EP 1482868 B1 2/2009
EP 1255510 B3 3/2009
EP 1330213 B1 3/2009
EP 1429651 B1 3/2009
EP 1610727 B1 4/2009
EP 1617788 B1 4/2009
EP 1634547 B1 4/2009
EP 1790318 B1 4/2009
EP 2040645 A1 4/2009
EP 1250165 B1 5/2009
EP 1842508 B1 6/2009
EP 1968482 B1 6/2009
EP 2072027 A1 6/2009
EP 1343438 B1 7/2009
EP 1406608 B1 7/2009
EP 1509256 B1 7/2009
EP 1626681 B1 7/2009
EP 1723935 B1 7/2009
EP 1803420 B1 7/2009
EP 2073755 A2 7/2009
EP 1401359 B1 8/2009
EP 1411865 B1 8/2009
EP 1485033 B1 8/2009
EP 1581120 B1 8/2009
EP 1620040 B1 8/2009
EP 1684667 B1 8/2009
EP 1872743 B1 8/2009
EP 1100378 B1 9/2009
EP 1198203 B1 9/2009
EP 1370201 B1 9/2009
EP 1408850 B1 9/2009
EP 1472996 B1 9/2009
EP 1478364 B1 9/2009
EP 1653888 B1 9/2009
EP 1785154 B1 9/2009
EP 1881804 B1 9/2009
EP 1903991 B1 9/2009
EP 1418885 B1 10/2009
EP 1561437 B1 10/2009
EP 1615595 B1 10/2009
EP 1353612 B1 11/2009
EP 1348406 B1 12/2009
EP 1370202 B1 12/2009
EP 1603492 B1 12/2009
EP 1670364 B1 12/2009
EP 1759663 B1 12/2009
EP 1994887 B1 12/2009
EP 1615593 B1 1/2010
EP 1643938 B1 1/2010
EP 1863402 B1 1/2010
EP 1943942 B1 1/2010
EP 2010101 B1 1/2010
EP 2081518 B1 1/2010
EP 1703865 B1 2/2010
EP 1276437 B1 3/2010
EP 1276439 B1 3/2010
EP 1411867 B1 3/2010
EP 1458313 B1 3/2010
EP 1520519 B1 3/2010
EP 1648340 B1 3/2010
EP 1682048 B1 3/2010
EP 1773239 B1 3/2010
EP 1935377 B1 3/2010
EP 1994912 B1 3/2010
EP 1154738 B1 4/2010
EP 1531762 B1 4/2010
EP 1600178 B1 4/2010
EP 1626682 B1 4/2010
EP 1511445 B1 5/2010
EP 1193213 B1 6/2010
EP 1250097 B1 6/2010
EP 1978895 B1 6/2010
EP 1572033 B1 7/2010
EP 1968491 B1 7/2010
EP 2019652 B1 7/2010
EP 1272249 B1 8/2010
EP 1610722 B1 8/2010
EP 1682047 B1 8/2010
EP 1952772 B1 8/2010
EP 1427356 B1 9/2010
EP 1631218 B1 9/2010
EP 1765224 B1 9/2010
EP 1871290 B1 9/2010
EP 1895288 B1 9/2010
EP 1895913 B1 9/2010
EP 2014257 B1 9/2010
EP 1176913 B1 10/2010
EP 1178758 B1 10/2010
EP 1248579 B1 10/2010
EP 1913899 B1 10/2010
EP 1259193 B1 11/2010
EP 1928357 B1 11/2010
EP 1968660 B1 11/2010
EP 2249711 A2 11/2010
EP 1408895 B1 12/2010
EP 1465554 B1 12/2010
EP 1732473 B1 12/2010
EP 1768610 B1 12/2010
EP 1827314 B1 12/2010
EP 1940321 B1 12/2010
EP 1964532 B1 12/2010
EP 2078498 B1 12/2010
EP 1600182 B1 1/2011
EP 1617789 B1 1/2011
EP 1663332 B1 1/2011
EP 2147659 B1 1/2011
EP 2268231 A2 1/2011
EP 2273951 A1 1/2011
EP 1187582 B1 2/2011
EP 1450733 B1 2/2011
EP 1803421 B1 2/2011

(56) References Cited

FOREIGN PATENT DOCUMENTS

| | | | |
|---|---|---|---|
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | A1 | 8/2011 |
| EP | 2349097 | A1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2536353 | A1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538881 | A1 | 1/2013 |
| EP | 2538882 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 175062281 | | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |

(56) References Cited

FOREIGN PATENT DOCUMENTS

EP 1694246 B1 6/2013
EP 1948087 B1 6/2013
EP 2135559 B1 6/2013
EP 1115335 B1 7/2013
EP 1663339 B1 7/2013
EP 1864687 B1 7/2013
EP 1977719 B1 7/2013
EP 2111337 B1 7/2013
EP 2298237 B1 7/2013
EP 2309949 B1 7/2013
EP 2608741 A2 7/2013
EP 2611388 A2 7/2013
EP 2611389 A2 7/2013
EP 2618781 A2 7/2013
EP 1599151 B1 8/2013
EP 1761211 B1 8/2013
EP 2047871 B1 8/2013
EP 2142144 B1 8/2013
EP 2150206 B1 8/2013
EP 2319459 B1 8/2013
EP 2397108 B1 8/2013
EP 2623068 A1 8/2013
EP 1758523 B1 9/2013
EP 1545392 B1 10/2013
EP 1638627 B1 10/2013
EP 1779868 B1 10/2013
EP 2073756 B1 10/2013
EP 2111190 B1 10/2013
EP 2651336 A1 10/2013
EP 1848375 B1 11/2013
EP 1928356 B1 11/2013
EP 1933766 B1 11/2013
EP 2109417 B1 11/2013
EP 2194925 B1 11/2013
EP 2387977 B1 11/2013
EP 2476394 B1 11/2013
EP 2529701 B1 11/2013
EP 1945142 B1 12/2013
EP 2387972 B1 12/2013
EP 2477555 B1 12/2013
EP 2670349 A2 12/2013
EP 2670351 A1 12/2013
EP 2117476 B1 1/2014
EP 2526895 B1 1/2014
EP 2526899 B1 1/2014
EP 2529696 B1 1/2014
EP 2529697 B1 1/2014
EP 2529698 B1 1/2014
EP 2529699 B1 1/2014
EP 2679198 A1 1/2014
EP 2688516 A1 1/2014
EP 1395214 B1 2/2014
EP 1499266 B1 2/2014
EP 1838241 B1 2/2014
EP 2520250 B1 2/2014
EP 2526977 B1 2/2014
EP 2693985 A1 2/2014
EP 2698129 A1 2/2014
EP 2699302 A2 2/2014
EP 1629794 B1 3/2014
EP 1919398 B1 3/2014
EP 2099508 B1 3/2014
EP 2399549 B1 3/2014
EP 2422823 B1 3/2014
EP 2706958 A1 3/2014
EP 1804860 B1 4/2014
EP 1926455 B1 4/2014
EP 2081519 B1 4/2014
EP 2117477 B1 4/2014
EP 2405966 B1 4/2014
EP 2420205 B1 4/2014
EP 2593048 B1 4/2014
EP 2713894 A2 4/2014
EP 2713955 A2 4/2014
EP 2723273 A2 4/2014
EP 1499265 B1 5/2014
EP 1594569 B1 5/2014
EP 2029056 B1 5/2014
EP 2257243 B1 5/2014
EP 1791500 B1 6/2014
EP 2073753 B1 6/2014
EP 2306933 B1 6/2014
EP 2331017 B1 6/2014
EP 2337522 B1 6/2014
EP 2389897 B1 6/2014
EP 2606723 B1 6/2014
EP 2739250 A1 6/2014
EP 1487350 B1 7/2014
EP 1977718 B1 7/2014
EP 2117469 B1 7/2014
EP 2124826 B1 7/2014
EP 2258316 B1 7/2014
EP 2747708 A1 7/2014
EP 2750630 A1 7/2014
EP 2750631 A1 7/2014
EP 1667604 B1 8/2014
EP 1786368 B1 8/2014
EP 2211779 B1 8/2014
EP 2217174 B1 8/2014
EP 2293740 B1 8/2014
EP 2367504 B1 8/2014
EP 2453942 B1 8/2014
EP 2475328 B1 8/2014
EP 2545884 B1 8/2014
EP 2571460 B1 8/2014
EP 2763708 A2 8/2014
EP 2765954 A1 8/2014
EP 1935378 B1 9/2014
EP 2246011 B1 9/2014
EP 2422749 B1 9/2014
EP 2531139 B1 9/2014
EP 2609893 B1 9/2014
EP 2777616 A1 9/2014
EP 2779945 A1 9/2014
EP 1853199 B1 10/2014
EP 2133039 B1 10/2014
EP 2549955 B1 10/2014
EP 2549956 B1 10/2014
EP 2651335 B1 10/2014
EP 2785281 A1 10/2014
EP 2793743 A1 10/2014
EP 2793749 A1 10/2014
EP 2793752 A1 10/2014
EP 2049721 B1 11/2014
EP 2142143 B1 11/2014
EP 2229921 B1 11/2014
EP 2288403 B1 11/2014
EP 2415421 B1 11/2014
EP 1551274 B1 12/2014
EP 1768735 B1 12/2014
EP 1959865 B1 12/2014
EP 2077718 B1 12/2014
EP 2303185 B1 12/2014
EP 2334857 B1 12/2014
EP 2365840 B1 12/2014
EP 2420207 B1 12/2014
EP 2422750 B1 12/2014
EP 2707073 B1 12/2014
EP 1768630 B1 1/2015
EP 2254515 B1 1/2015
EP 2641569 B1 1/2015
EP 2709559 B1 1/2015
EP 2825203 A1 1/2015
EP 1903990 B1 2/2015
EP 2255753 B1 2/2015
EP 2335649 B1 2/2015
EP 2522308 B1 2/2015
EP 2591754 B1 2/2015
EP 2835112 A1 2/2015
EP 2838473 A1 2/2015
EP 1861045 B1 3/2015
EP 2029057 B1 3/2015
EP 2193761 B1 3/2015
EP 2379010 B1 3/2015

(56) References Cited

FOREIGN PATENT DOCUMENTS

EP 2416737 B1 3/2015
EP 2849678 A1 3/2015
EP 1791495 B1 4/2015
EP 2298252 B1 4/2015
EP 2536359 B1 4/2015
EP 2538879 B1 4/2015
EP 2609894 B1 4/2015
EP 2693984 B1 4/2015
EP 2712633 B1 4/2015
EP 2747707 B1 4/2015
EP 2856973 A1 4/2015
EP 2862546 A1 4/2015
EP 2863842 A1 4/2015
EP 1465555 B1 5/2015
EP 1924224 B1 5/2015
EP 1992369 B1 5/2015
EP 2410947 B1 5/2015
EP 2484311 B1 5/2015
EP 2654616 B1 5/2015
EP 2866741 A1 5/2015
EP 1646332 B1 6/2015
EP 2745805 B1 6/2015
EP 2749254 B1 6/2015
EP 2877123 A2 6/2015
EP 2882374 A1 6/2015
EP 2884906 A1 6/2015
EP 1729685 B1 7/2015
EP 1976439 B1 7/2015
EP 2068767 B1 7/2015
EP 2068769 B1 7/2015
EP 2444031 B1 7/2015
EP 2455041 B1 7/2015
EP 2498719 B1 7/2015
EP 2558030 B1 7/2015
EP 2752209 B1 7/2015
EP 2892467 A1 7/2015
EP 1702247 B1 8/2015
EP 1729688 B1 8/2015
EP 1887979 B1 8/2015
EP 2032079 B1 8/2015
EP 2219558 B1 8/2015
EP 2234657 B1 8/2015
EP 2250976 B1 8/2015
EP 2262447 B1 8/2015
EP 2303384 B1 8/2015
EP 2387365 B1 8/2015
EP 2560579 B1 8/2015
EP 2575621 B1 8/2015
EP 2590595 B1 8/2015
EP 2709560 B1 8/2015
EP 2755603 B1 8/2015
EP 2906147 A1 8/2015
EP 1534185 B1 9/2015
EP 1765225 B1 9/2015
EP 1778127 B1 9/2015
EP 2094194 B1 9/2015
EP 2201911 B1 9/2015
EP 2306934 B1 9/2015
EP 2397113 B1 9/2015
EP 2453843 B1 9/2015
EP 2459127 B1 9/2015
EP 2675396 B1 9/2015
EP 2675397 B1 9/2015
EP 2736454 B1 9/2015
EP 2754414 A4 9/2015
EP 2790609 B1 9/2015
EP 2805893 B1 9/2015
EP 2911611 A1 9/2015
EP 2916781 A2 9/2015
EP 2919712 A1 9/2015
EP 1734903 B1 10/2015
EP 1863546 B1 10/2015
EP 1900343 B1 10/2015
EP 2081515 B1 10/2015
EP 2191792 B1 10/2015
EP 2254513 B1 10/2015
EP 2381896 B1 10/2015
EP 2450008 B1 10/2015
EP 2544626 B1 10/2015
EP 2561830 B1 10/2015
EP 2600798 B1 10/2015
EP 2626039 B1 10/2015
EP 2647354 B1 10/2015
EP 2729093 B1 10/2015
EP 2836165 B1 10/2015
EP 1863545 B1 11/2015
EP 2303395 B1 11/2015
EP 2497446 B1 11/2015
EP 2772228 B1 11/2015
EP 1482869 B1 12/2015
EP 1551473 B1 12/2015
EP 1748745 B1 12/2015
EP 1755459 B1 12/2015
EP 1850796 B1 12/2015
EP 1922030 B1 12/2015
EP 1954212 B1 12/2015
EP 2424472 B1 12/2015
EP 2470120 B1 12/2015
EP 2542179 B1 12/2015
EP 2948100 A1 12/2015
EP 2948103 A2 12/2015
EP 2950752 A2 12/2015
EP 2959866 A1 12/2015
EP 1991168 B1 1/2016
EP 2254512 B1 1/2016
EP 2422748 B1 1/2016
EP 2962664 A1 1/2016
EP 2964153 A1 1/2016
EP 2967700 A1 1/2016
EP 2967807 A2 1/2016
EP 2967834 A1 1/2016
EP 2967856 A1 1/2016
EP 2967858 A2 1/2016
EP 2967860 A1 1/2016
EP 2967866 A2 1/2016
EP 2977026 A1 1/2016
EP 1754684 B1 2/2016
EP 1835948 B1 2/2016
EP 2012712 B1 2/2016
EP 2285318 B1 2/2016
EP 2731550 B1 2/2016
EP 2926766 B1 2/2016
EP 2982337 A1 2/2016
EP 1585463 B1 3/2016
EP 1638621 B1 3/2016
EP 1804726 B1 3/2016
EP 1865886 B1 3/2016
EP 1887982 B1 3/2016
EP 2150205 B1 3/2016
EP 2278944 B1 3/2016
EP 2291126 B1 3/2016
EP 2517674 B1 3/2016
EP 2520253 B1 3/2016
EP 2526897 B1 3/2016
EP 2621409 A4 3/2016
EP 2670353 B1 3/2016
EP 2674130 B1 3/2016
EP 2780042 B1 3/2016
EP 2991584 A1 3/2016
EP 2991587 A2 3/2016
EP 2991588 A1 3/2016
EP 2994072 A1 3/2016
EP 2994075 A1 3/2016
EP 2996632 A1 3/2016
EP 2996633 A1 3/2016
EP 2996641 A1 3/2016
EP 2999435 A1 3/2016
EP 1420730 B1 4/2016
EP 1545371 B1 4/2016
EP 1592367 B1 4/2016
EP 1708649 B1 4/2016
EP 1871300 B1 4/2016
EP 2168536 B1 4/2016
EP 2399550 B1 4/2016

(56) References Cited

FOREIGN PATENT DOCUMENTS

EP 2433591 B1 4/2016
EP 2478871 B1 4/2016
EP 2536355 B1 4/2016
EP 2572676 B1 4/2016
EP 2606852 B1 4/2016
EP 2621408 B1 4/2016
EP 2626041 B1 4/2016
EP 2633821 B1 4/2016
EP 2670354 B1 4/2016
EP 2702965 B1 4/2016
EP 2704669 B1 4/2016
EP 2815725 B1 4/2016
EP 3007651 A1 4/2016
EP 3010564 A1 4/2016
EP 2194933 B1 5/2016
EP 2237746 B1 5/2016
EP 2378947 B1 5/2016
EP 2542184 B1 5/2016
EP 2572684 B1 5/2016
EP 2582326 B1 5/2016
EP 2618784 B1 5/2016
EP 2654623 B1 5/2016
EP 2656816 B1 5/2016
EP 2680791 B1 5/2016
EP 2693986 B1 5/2016
EP 2806805 B1 5/2016
EP 2866739 B1 5/2016
EP 2889020 B1 5/2016
EP 2926767 B1 5/2016
EP 2949292 B1 5/2016
EP 3019092 A1 5/2016
EP 1906884 B1 6/2016
EP 2111800 B1 6/2016
EP 2160156 B1 6/2016
EP 2190379 B1 6/2016
EP 2193762 B1 6/2016
EP 2416739 B1 6/2016
EP 2453989 B1 6/2016
EP 2515800 B1 6/2016
EP 2558031 B1 6/2016
EP 2563236 B1 6/2016
EP 2572675 B1 6/2016
EP 2626040 B1 6/2016
EP 2704668 B1 6/2016
EP 2777811 B1 6/2016
EP 2815724 B1 6/2016
EP 2854710 B1 6/2016
EP 2901966 B1 6/2016
EP 3024527 A2 6/2016
EP 1605866 B1 7/2016
EP 1933756 B1 7/2016
EP 2393452 B1 7/2016
EP 2410948 B1 7/2016
EP 2412397 B1 7/2016
EP 2724690 B1 7/2016
EP 2815723 B1 7/2016
EP 2870945 B1 7/2016
EP 3038567 A1 7/2016
EP 3040054 A1 7/2016
EP 3042635 A1 7/2016
EP 3043745 A1 7/2016
EP 3043747 A1 7/2016
EP 3043755 A1 7/2016
EP 1401358 B1 8/2016
EP 1734902 B1 8/2016
EP 1915105 B1 8/2016
EP 1937186 B1 8/2016
EP 2292186 B1 8/2016
EP 2379012 B1 8/2016
EP 2385809 B1 8/2016
EP 2536345 B1 8/2016
EP 2537490 B1 8/2016
EP 2549954 B1 8/2016
EP 2618779 B1 8/2016
EP 2670352 B1 8/2016
EP 2829235 B1 8/2016
EP 2853238 B1 8/2016
EP 2866738 B1 8/2016
EP 2906150 B1 8/2016
EP 3052053 A1 8/2016
EP 3052611 A1 8/2016
EP 3060171 A1 8/2016
EP 3060174 A1 8/2016
EP 3061421 A1 8/2016
EP 3061422 A1 8/2016
EP 1492478 B1 9/2016
EP 1912697 B1 9/2016
EP 2393449 B1 9/2016
EP 2670356 B1 9/2016
EP 2793969 B1 9/2016
EP 2809271 B1 9/2016
EP 2896425 B1 9/2016
EP 3068345 A1 9/2016
EP 3068346 A1 9/2016
EP 3071148 A1 9/2016
EP 3071149 A1 9/2016
EP 2023858 B1 10/2016
EP 2112912 B1 10/2016
EP 2663257 B1 10/2016
EP 2727612 B1 10/2016
EP 2760384 B1 10/2016
EP 2806829 B1 10/2016
EP 2840319 B1 10/2016
EP 2858599 B1 10/2016
EP 2918250 B1 10/2016
EP 2922592 A4 10/2016
EP 2934387 B1 10/2016
EP 3076901 A1 10/2016
EP 3079633 A1 10/2016
EP 1539047 B1 11/2016
EP 2282700 B1 11/2016
EP 2400926 B1 11/2016
EP 2467104 B1 11/2016
EP 2525743 B1 11/2016
EP 2549953 B1 11/2016
EP 2575696 B1 11/2016
EP 2598045 B1 11/2016
EP 2670355 B1 11/2016
EP 2676640 B1 11/2016
EP 2680792 B1 11/2016
EP 2707053 B1 11/2016
EP 2717803 B1 11/2016
EP 2773297 B1 11/2016
EP 2801387 B1 11/2016
EP 2844192 B1 11/2016
EP 2849679 B1 11/2016
EP 2877122 B1 11/2016
EP 2908778 B1 11/2016
EP 2922500 B1 11/2016
EP 2922501 B1 11/2016
EP 2967854 B1 11/2016
EP 3020365 B1 11/2016
EP 3090703 A1 11/2016
EP 3096713 A1 11/2016
EP 1645244 B1 12/2016
EP 1667614 B1 12/2016
EP 1684656 B1 12/2016
EP 1684670 B1 12/2016
EP 1750592 B1 12/2016
EP 1883375 B1 12/2016
EP 2293739 B1 12/2016
EP 2339988 B1 12/2016
EP 2512375 B1 12/2016
EP 2754417 B1 12/2016
EP 2754418 B1 12/2016
EP 2755562 B1 12/2016
EP 2889019 B1 12/2016
EP 3010442 B1 12/2016
EP 3099271 A1 12/2016
EP 3102150 A1 12/2016
EP 3107495 A1 12/2016
EP 3107498 A2 12/2016
EP 3107500 A1 12/2016
EP 1893127 B1 1/2017

(56) References Cited

FOREIGN PATENT DOCUMENTS

| | | | |
|---|---|---|---|
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 3158975 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384185 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3175823 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774830 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |

(56) References Cited

FOREIGN PATENT DOCUMENTS

| | | | |
|---|---|---|---|
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967869 | B1 | 1/2018 |
| EP | 2967883 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3266417 | A1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277221 | A1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |

(56) References Cited

FOREIGN PATENT DOCUMENTS

EP 3288498 A1 3/2018
EP 3288499 A1 3/2018
EP 3290004 A1 3/2018
EP 3290007 A1 3/2018
EP 3294214 A1 3/2018
EP 3294215 A1 3/2018
EP 3294218 A1 3/2018
EP 3296979 A1 3/2018
EP 3298970 A1 3/2018
EP 3298987 A1 3/2018
EP 3298988 A1 3/2018
EP 2209440 B1 4/2018
EP 2536357 B1 4/2018
EP 2605725 B1 4/2018
EP 2608743 B1 4/2018
EP 2709561 B1 4/2018
EP 2787925 B1 4/2018
EP 2789314 B1 4/2018
EP 2900150 B1 4/2018
EP 2908779 B1 4/2018
EP 2922502 B1 4/2018
EP 2964441 B1 4/2018
EP 2967868 B1 4/2018
EP 2979685 B1 4/2018
EP 2994073 B1 4/2018
EP 3095394 B1 4/2018
EP 3128927 A4 4/2018
EP 3134033 B1 4/2018
EP 3137146 A4 4/2018
EP 3280482 A4 4/2018
EP 3302297 A2 4/2018
EP 3302362 A1 4/2018
EP 3302367 A1 4/2018
EP 3307208 A1 4/2018
EP 3308745 A1 4/2018
EP 3310301 A1 4/2018
EP 3311774 A1 4/2018
EP 3311775 A1 4/2018
EP 3311783 A1 4/2018
EP 1945112 B1 5/2018
EP 2007313 B1 5/2018
EP 2316381 B2 5/2018
EP 2377469 B1 5/2018
EP 2531115 B1 5/2018
EP 2561831 B1 5/2018
EP 2605724 B1 5/2018
EP 2723277 B1 5/2018
EP 2741711 B1 5/2018
EP 2755573 B1 5/2018
EP 2768429 B1 5/2018
EP 2819618 B1 5/2018
EP 2833836 B1 5/2018
EP 2886083 B1 5/2018
EP 2926840 B1 5/2018
EP 2943157 B1 5/2018
EP 2948099 B1 5/2018
EP 3000437 B1 5/2018
EP 3145448 B1 5/2018
EP 3316819 A1 5/2018
EP 3316821 A1 5/2018
EP 3322381 A1 5/2018
EP 3322383 A1 5/2018
EP 3323353 A1 5/2018
EP 3323439 A1 5/2018
EP 3324892 A1 5/2018
EP 3326584 A1 5/2018
EP 315447581 5/2018
EP 2150312 B1 6/2018
EP 2379322 B1 6/2018
EP 2400925 B1 6/2018
EP 2552355 B1 6/2018
EP 2560589 B1 6/2018
EP 2563277 B1 6/2018
EP 2661305 B1 6/2018
EP 2736456 B1 6/2018
EP 2782523 B1 6/2018
EP 3056170 B1 6/2018
EP 3062745 B1 6/2018
EP 3130320 B1 6/2018
EP 3187150 B1 6/2018
EP 3334378 A1 6/2018
EP 3334380 A1 6/2018
EP 3334381 A1 6/2018
EP 3335670 A1 6/2018
EP 3337412 A1 6/2018
EP 3337424 A1 6/2018
EP 2478872 B1 7/2018
EP 2563278 B1 7/2018
EP 2616004 B1 7/2018
EP 2779943 B1 7/2018
EP 2802290 B1 7/2018
EP 2816980 B1 7/2018
EP 2938293 B1 7/2018
EP 3107496 B1 7/2018
EP 3178450 B1 7/2018
EP 3212097 B1 7/2018
EP 3340923 A1 7/2018
EP 3340932 A1 7/2018
EP 3340934 A1 7/2018
EP 3340936 A1 7/2018
EP 3340945 A1 7/2018
EP 3342355 A1 7/2018
EP 3342377 A1 7/2018
EP 3344158 A1 7/2018
EP 3346952 A1 7/2018
EP 3347182 A1 7/2018
EP 3348235 A1 7/2018
EP 3349693 A1 7/2018
EP 2536354 B1 8/2018
EP 2616006 B1 8/2018
EP 2797556 B1 8/2018
EP 2822473 B1 8/2018
EP 2854711 B1 8/2018
EP 2866847 B1 8/2018
EP 2918246 B1 8/2018
EP 2967845 B1 8/2018
EP 2999436 B1 8/2018
EP 3013281 B1 8/2018
EP 3060170 B1 8/2018
EP 3104811 B1 8/2018
EP 3143944 B1 8/2018
EP 3157467 B1 8/2018
EP 3193791 B1 8/2018
EP 3241526 B1 8/2018
EP 3355800 A1 8/2018
EP 3360513 A1 8/2018
EP 3360514 A1 8/2018
EP 3361988 A1 8/2018
EP 3361991 A1 8/2018
EP 1156755 B1 9/2018
EP 2114305 B1 9/2018
EP 2155115 B1 9/2018
EP 2601910 B1 9/2018
EP 2617390 B1 9/2018
EP 2734157 B1 9/2018
EP 2968674 B1 9/2018
EP 2999415 B1 9/2018
EP 3106130 B1 9/2018
EP 3151763 B1 9/2018
EP 3213717 B1 9/2018
EP 3245985 B1 9/2018
EP 3367979 A1 9/2018
EP 3370649 A1 9/2018
EP 3370650 A1 9/2018
EP 3377000 A1 9/2018
EP 1827256 B1 10/2018
EP 1850790 B1 10/2018
EP 2063823 B1 10/2018
EP 2124825 B1 10/2018
EP 2249746 B1 10/2018
EP 2254514 B1 10/2018
EP 2285309 B1 10/2018
EP 2455942 B1 10/2018
EP 2571561 B1 10/2018

(56) References Cited

FOREIGN PATENT DOCUMENTS

| | | | |
|---|---|---|---|
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 3388027 | A1 | 10/2018 |
| EP | 3389557 | A1 | 10/2018 |
| EP | 3390706 | A1 | 10/2018 |
| EP | 283617181 | | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3398562 | A1 | 11/2018 |
| EP | 3400908 | A1 | 11/2018 |
| EP | 3403616 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3407834 | A1 | 12/2018 |
| EP | 3410984 | A1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3427695 | A1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688582 | B1 | 2/2019 |
| EP | 2714068 | B1 | 2/2019 |
| EP | 2720841 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | A4 | 2/2019 |
| EP | 3435919 | A1 | 2/2019 |
| EP | 3441045 | A1 | 2/2019 |
| EP | 3442469 | A1 | 2/2019 |
| EP | 3443937 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3449969 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3454795 | A1 | 3/2019 |
| EP | 3457987 | A1 | 3/2019 |
| EP | 3457988 | A1 | 3/2019 |
| EP | 3457990 | A1 | 3/2019 |
| EP | 3458136 | A2 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |

(56) References Cited

FOREIGN PATENT DOCUMENTS

| | | | |
|---|---|---|---|
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490657 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2841572 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 3517075 | A1 | 7/2019 |
| EP | 1861043 | B1 | 8/2019 |
| EP | 2004095 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |

(56) References Cited

FOREIGN PATENT DOCUMENTS

| | | | |
|---|---|---|---|
| EP | 3531975 | A1 | 9/2019 |
| EP | 3534840 | A1 | 9/2019 |
| EP | 3534841 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |
| EP | 3539509 | A1 | 9/2019 |
| EP | 3541316 | A1 | 9/2019 |
| EP | 3541325 | A1 | 9/2019 |
| EP | 3541328 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3545905 | A1 | 10/2019 |
| EP | 3547936 | A1 | 10/2019 |
| EP | 3547966 | A1 | 10/2019 |
| EP | 3549555 | A1 | 10/2019 |
| EP | 3549556 | A1 | 10/2019 |
| EP | 3552585 | A1 | 10/2019 |
| EP | 3554424 | A1 | 10/2019 |
| EP | 3556323 | A1 | 10/2019 |
| EP | 3558165 | A1 | 10/2019 |
| EP | 3558168 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3563799 | A1 | 11/2019 |
| EP | 3563806 | A1 | 11/2019 |
| EP | 3570779 | A1 | 11/2019 |
| EP | 3572045 | A1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3579788 | A1 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3595588 | A1 | 1/2020 |
| EP | 3600156 | A1 | 2/2020 |
| EP | 3600159 | A1 | 2/2020 |
| EP | 3606443 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 317582261 | | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628239 | A1 | 4/2020 |
| EP | 3628274 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |

(56) References Cited

FOREIGN PATENT DOCUMENTS

EP 3648709 A1 5/2020
EP 3656354 A1 5/2020
EP 1648339 B2 6/2020
EP 2072027 B1 6/2020
EP 2331016 B8 6/2020
EP 2616007 B1 6/2020
EP 2967856 B1 6/2020
EP 3042635 B1 6/2020
EP 3060165 B1 6/2020
EP 3280338 B1 6/2020
EP 3283010 B1 6/2020
EP 3400908 B1 6/2020
EP 3494928 B1 6/2020
EP 3498225 B1 6/2020
EP 3583920 B1 6/2020
EP 3659553 A1 6/2020
EP 3661429 A1 6/2020
EP 3661436 A1 6/2020
EP 3668450 A1 6/2020
EP 3668452 A1 6/2020
EP 3669828 A1 6/2020
EP 3669829 A1 6/2020
EP 2271284 B1 7/2020
EP 2291145 B1 7/2020
EP 2512952 B1 7/2020
EP 2558029 B1 7/2020
EP 2693985 B1 7/2020
EP 2858708 B1 7/2020
EP 2862546 B1 7/2020
EP 2967807 B1 7/2020
EP 2967866 B1 7/2020
EP 3061421 B1 7/2020
EP 3107497 B1 7/2020
EP 3139862 B1 7/2020
EP 3423000 B1 7/2020
EP 3441045 B1 7/2020
EP 3451972 B1 7/2020
EP 3501454 B1 7/2020
EP 3512466 B1 7/2020
EP 3616652 B1 7/2020
EP 3672528 A1 7/2020
EP 3672529 A1 7/2020
EP 3672532 A1 7/2020
EP 3673925 A1 7/2020
EP 3679894 A1 7/2020
EP 3681439 A1 7/2020
EP 3681441 A1 7/2020
EP 3682852 A1 7/2020
EP 3682854 A1 7/2020
EP 3685802 A1 7/2020
EP 2367505 B1 8/2020
EP 2497445 B1 8/2020
EP 2537486 B1 8/2020
EP 2777616 B1 8/2020
EP 3007651 B1 8/2020
EP 3052053 B1 8/2020
EP 3237033 B1 8/2020
EP 3388005 B1 8/2020
EP 3410986 B1 8/2020
EP 3451974 B1 8/2020
EP 3463192 B1 8/2020
EP 3554423 B1 8/2020
EP 3568089 A4 8/2020
EP 3573544 B1 8/2020
EP 3634255 B1 8/2020
EP 3689299 A1 8/2020
EP 3691567 A1 8/2020
EP 3695810 A1 8/2020
EP 3697342 A1 8/2020
EP 3697346 A1 8/2020
EP 2485795 B1 9/2020
EP 3125777 B1 9/2020
EP 3182930 B1 9/2020
EP 3285690 B1 9/2020
EP 3459500 B1 9/2020
EP 3570782 B1 9/2020
EP 3700467 A1 9/2020
EP 3711711 A1 9/2020
EP 3714936 A1 9/2020
EP 2979667 B2 10/2020
EP 3193783 B1 10/2020
EP 3490501 B1 10/2020
EP 3718509 A1 10/2020
EP 3720363 A1 10/2020
EP 3721811 A1 10/2020
EP 2387973 B1 11/2020
EP 2427144 B1 11/2020
EP 2506777 B1 11/2020
EP 2793743 B1 11/2020
EP 2825203 B1 11/2020
EP 2863842 B1 11/2020
EP 2967700 B1 11/2020
EP 2977026 B1 11/2020
EP 3139864 B1 11/2020
EP 3145451 B1 11/2020
EP 3156007 B1 11/2020
EP 3244834 B1 11/2020
EP 3298987 B1 11/2020
EP 3302362 B1 11/2020
EP 3311777 B1 11/2020
EP 3316819 B1 11/2020
EP 3361988 B1 11/2020
EP 3503813 B1 11/2020
EP 3527170 B1 11/2020
EP 3530236 B1 11/2020
EP 3590471 B1 11/2020
EP 3593762 B1 11/2020
EP 3737336 A1 11/2020
EP 3740162 A1 11/2020
EP 2370138 B1 12/2020
EP 2445450 B1 12/2020
EP 2739250 B1 12/2020
EP 2877123 B1 12/2020
EP 2967834 B1 12/2020
EP 2996632 B1 12/2020
EP 3090703 B1 12/2020
EP 3191025 B1 12/2020
EP 3202371 B1 12/2020
EP 3316822 B1 12/2020
EP 3334382 B1 12/2020
EP 3337424 B1 12/2020
EP 3367896 B1 12/2020
EP 3368582 B1 12/2020
EP 3397208 B1 12/2020
EP 3476366 B1 12/2020
EP 3481303 B1 12/2020
EP 3538028 B1 12/2020
EP 3539510 B1 12/2020
EP 3544548 B1 12/2020
EP 3545906 B1 12/2020
EP 3572117 B1 12/2020
EP 3593763 B1 12/2020
EP 3744291 A1 12/2020
EP 3749254 A1 12/2020
EP 3753535 A1 12/2020
EP 3756623 A1 12/2020
EP 1906883 B1 1/2021
EP 2334261 B1 1/2021
EP 2349096 B1 1/2021
EP 2568924 B1 1/2021
EP 2699202 B1 1/2021
EP 2713894 B1 1/2021
EP 2835112 B1 1/2021
EP 2996641 B1 1/2021
EP 3040054 B1 1/2021
EP 3131502 B1 1/2021
EP 3197397 B1 1/2021
EP 3256178 B1 1/2021
EP 3290007 B1 1/2021
EP 3316821 B1 1/2021
EP 3337412 B1 1/2021
EP 3432834 B1 1/2021
EP 3454786 B1 1/2021
EP 3474778 B1 1/2021

(56) References Cited

FOREIGN PATENT DOCUMENTS

| | | | |
|---|---|---|---|
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 3769721 | A1 | 1/2021 |
| EP | 2273951 | B1 | 2/2021 |
| EP | 2379008 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773271 | A1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |

(56) References Cited

FOREIGN PATENT DOCUMENTS

| | | | |
|---|---|---|---|
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3886763 | A1 | 10/2021 |
| EP | 3892240 | A1 | 10/2021 |
| EP | 3897454 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912595 | A1 | 11/2021 |
| EP | 3912596 | A1 | 11/2021 |
| EP | 2358307 | B1 | 12/2021 |
| EP | 2765954 | B1 | 12/2021 |
| EP | 2777608 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 3915493 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |
| EP | 3334380 | B1 | 3/2022 |
| EP | 3355800 | B1 | 3/2022 |
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 3962415 | A1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | A1 | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |

(56) References Cited

FOREIGN PATENT DOCUMENTS

| | | | |
|---|---|---|---|
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3908228 | B1 | 8/2022 |
| EP | 3915493 | B1 | 8/2022 |
| EP | 3967274 | B1 | 8/2022 |
| EP | 2670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3220857 | B1 | 9/2022 |
| EP | 3448315 | B1 | 9/2022 |
| EP | 3481335 | B1 | 9/2022 |
| EP | 3520715 | B1 | 9/2022 |
| EP | 3645065 | B1 | 9/2022 |
| EP | 3737336 | B1 | 9/2022 |
| EP | 2104470 | B1 | 10/2022 |
| EP | 2536353 | B1 | 10/2022 |
| EP | 2991588 | B1 | 10/2022 |
| EP | 3043755 | B1 | 10/2022 |
| EP | 3288491 | B1 | 10/2022 |
| EP | 3466373 | B1 | 10/2022 |
| EP | 3552585 | B1 | 10/2022 |
| EP | 3791828 | B1 | 10/2022 |
| EP | 3914191 | B1 | 10/2022 |
| EP | 2538882 | B1 | 11/2022 |
| EP | 2698129 | B1 | 11/2022 |
| EP | 2959866 | B1 | 11/2022 |
| EP | 3175823 | B1 | 11/2022 |
| EP | 3280358 | B1 | 11/2022 |
| EP | 3340923 | B1 | 11/2022 |
| EP | 3478224 | B1 | 11/2022 |
| EP | 3490659 | B1 | 11/2022 |
| EP | 3744291 | B1 | 11/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 8/2016 |
| FR | 3023704 | B1 | 8/2016 |
| FR | 300888581 | | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |
| GB | 2538749 | B | 8/2017 |
| GB | 2538072 | B | 11/2017 |
| GB | 2536538 | B | 7/2018 |
| GB | 2548891 | B | 7/2018 |
| JP | 2012523894 | A | 10/2012 |
| JP | 2015504337 | A | 2/2015 |
| JP | 2022506775 | A | 1/2022 |
| WO | WO-2008103722 | A2 | 8/2008 |
| WO | WO-2009134701 | A2 | 11/2009 |
| WO | WO-2011137531 | A1 | 11/2011 |
| WO | 2013075215 | | 5/2013 |
| WO | WO-2015188066 | A1 | 12/2015 |
| WO | WO-2020093172 | A1 | 5/2020 |

OTHER PUBLICATIONS

"European Application Serial No. 19883080.4, Response filed Dec. 23, 2021 to Communication pursuant to Rules 161(1) and 162 EPC", 31 pgs.

"Australian Application Serial No. 2019374743, First Examination Report dated Dec. 15, 2021", 3 pgs.

"Australian Application Serial No. 2019374743, Response filed Feb. 7, 2022 to First Examination Report dated Dec. 15, 2021", 18 pgs.

"Chinese Application Serial No. 201980088422.X, Voluntary Amendment filed Nov. 19, 2021", with English claims, 73 pgs.

"International Application Serial No. PCT CA2019 051598, International Search Report dated Feb. 5, 2020", 6 pgs.

"International Application Serial No. PCT CA2019 051598, Written Opinion dated Feb. 5, 2020", 6 pgs.

"Canadian Application Serial No. 3,118,599, Examiner's Rule 86(2) Report dated Oct. 13, 2022", 4 pgs.

"Japanese Application Serial No. 2021-524365, Notification of Reasons for Refusal dated Jul. 25, 2022", w/ English Translation, 9 pgs.

(56) References Cited

OTHER PUBLICATIONS

"Japanese Application Serial No. 2021-524365, Response filed Oct. 24, 2022 to Notification of Reasons for Refusal dated Jul. 25, 2022", with English translation of claims, 12 pgs.
"Australian Application Serial No. 2022203596, Voluntary Amendment filed Jul. 26, 2022", 21 pgs.
"European Application Serial No. 19883080.4, Extended European Search Report dated Jul. 7, 2022", 8 pgs.
"Canadian Application Serial No. 3,118,599, Response filed Feb. 9, 2023 to Examiner's Rule 86(2) Report dated Oct. 13, 2022", 47 pgs.

* cited by examiner

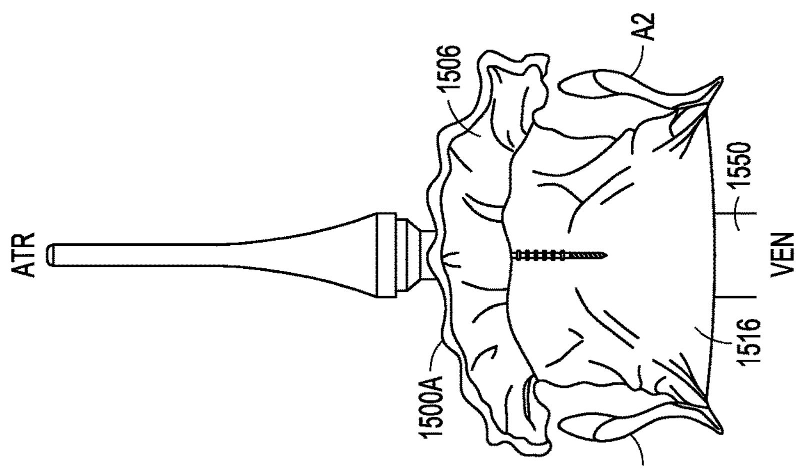
FIG. 15E
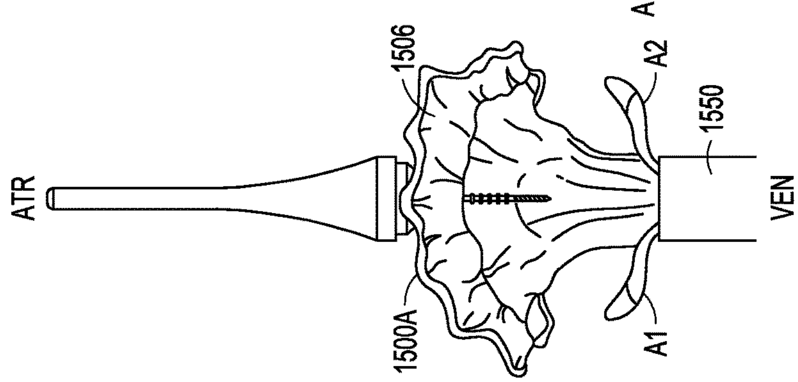
FIG. 15D
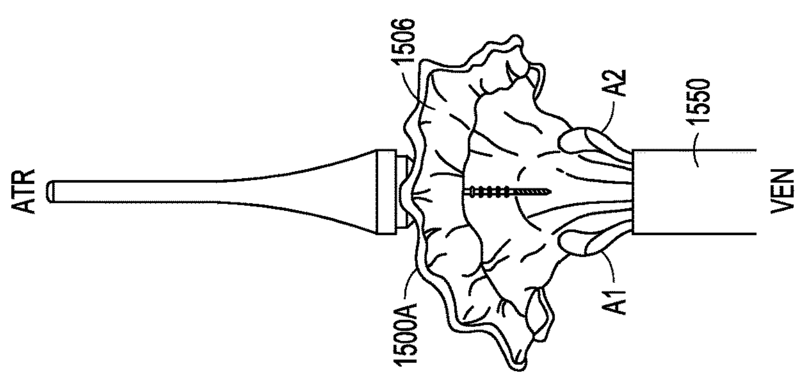
FIG. 15C
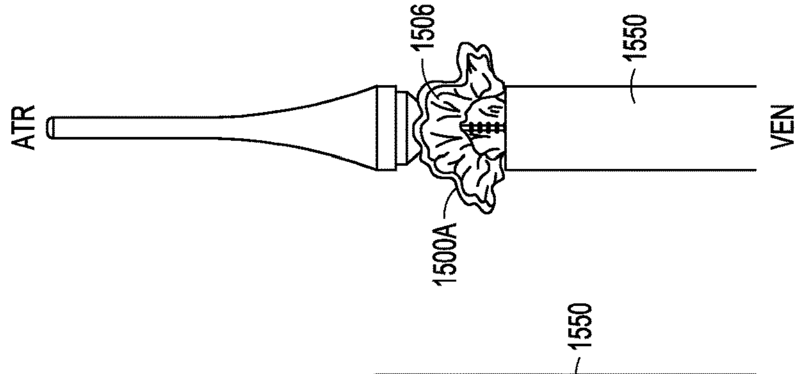
FIG. 15B
ATR
1550
VEN
FIG. 15A

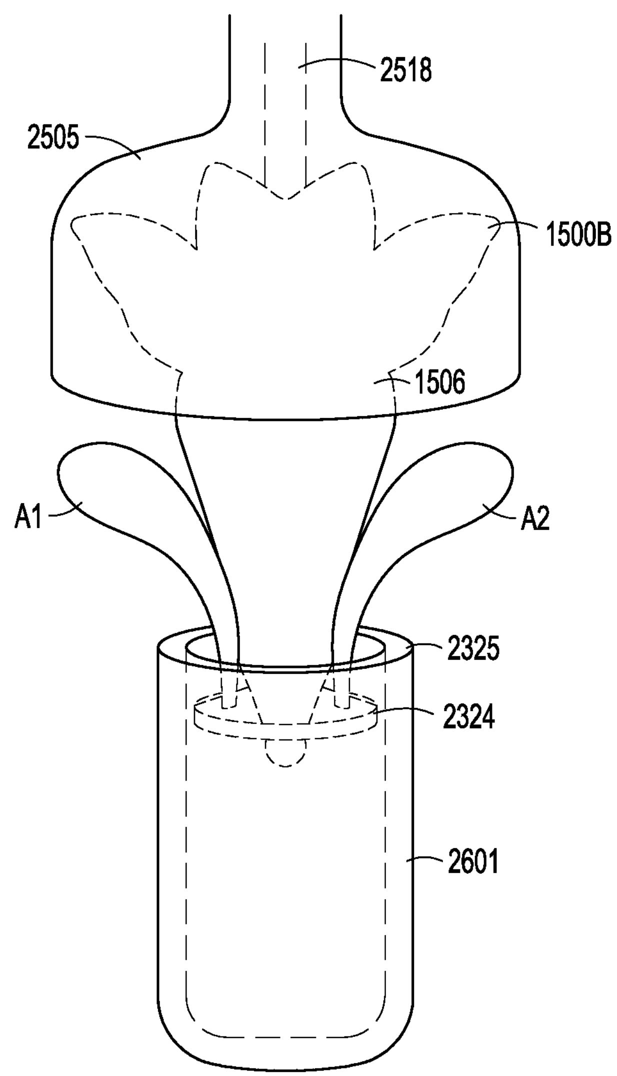
FIG. 25D1
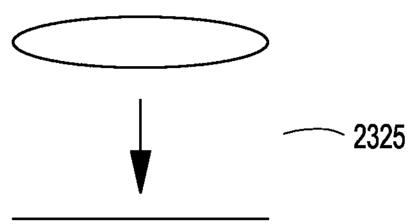
FIG. 25D2

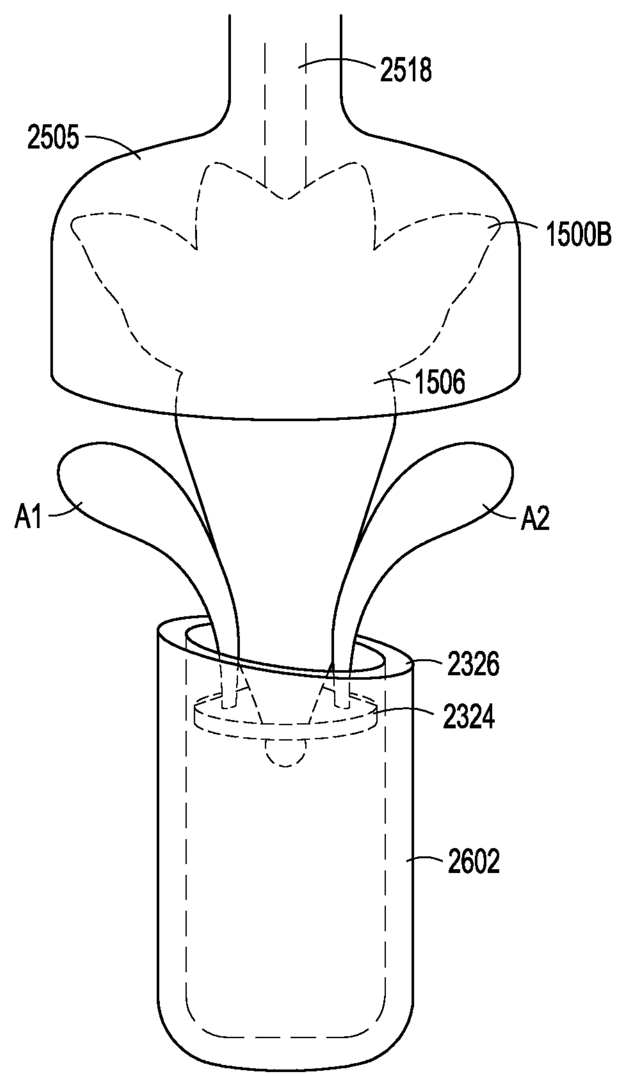
FIG. 25E1
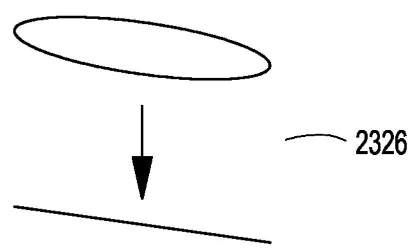
FIG. 25E2

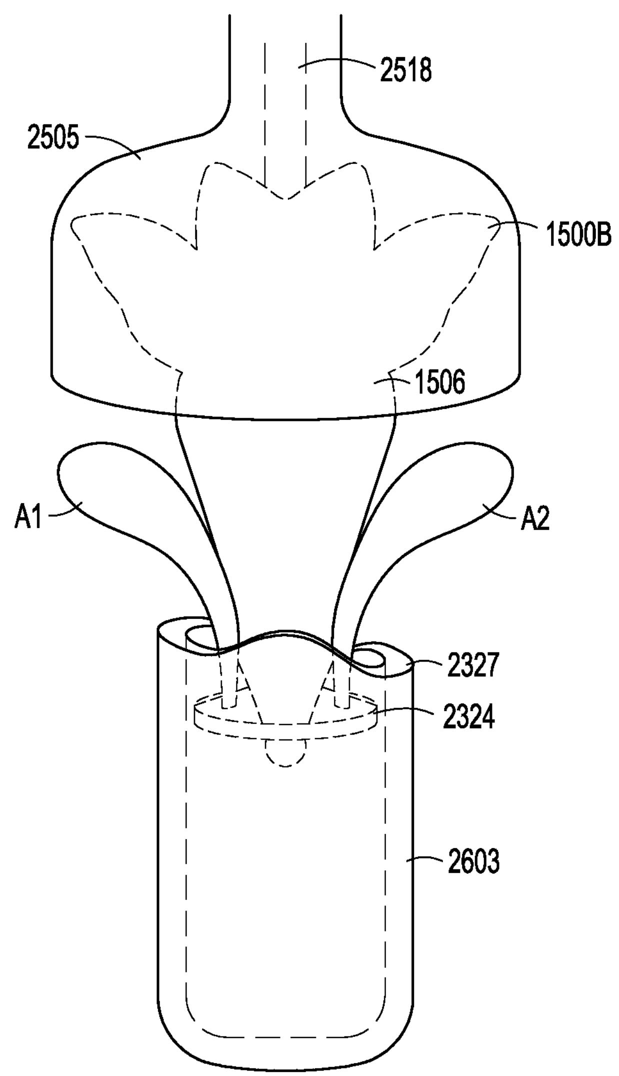
FIG. 25F1
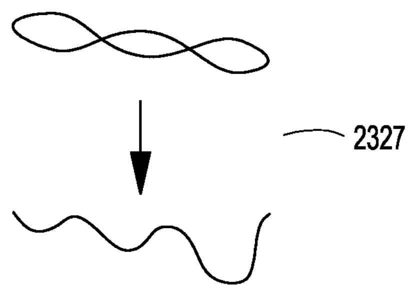
FIG. 25F2

403
22
12
11
16
30
24
34
23
9
37
41
27
25
401
6
402
13
14

VENTRICULAR DEPLOYMENT OF A TRANSCATHETER MITRAL VALVE PROSTHESIS

CLAIM OF PRIORITY

This patent application claims the benefit of priority to U.S. Provisional Patent Application Ser. No. 62/757,462, entitled "VENTRICULAR DEPLOYMENT OF A TRANSCATHETER MITRAL VALVE PROSTHESIS," filed on Nov. 8, 2018 (5131.014PRV); the entire contents of which is incorporated by reference herein in its entirety.

CROSS-REFERENCE TO RELATED PATENT DOCUMENTS

This patent application is also related to that of U.S. Pat. No. 8,579,964; US Patent Application Publication No. 2017/0165064; and U.S. patent application Ser. No. 16/111,898; the entire contents of which are incorporated herein by reference.

BACKGROUND OF THE INVENTION

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

Patents and publications which may be related include but are not limited to: PCT Publication Nos. WO2008/103722, WO2009/134701, and WO2011/137531. Other patent and publications which may be related but are not limited to, include: U.S. Patent Publication Nos. US2007/0016286, US2006/0241745, US2011/0015731, 2013/075215 and U.S. Pat. Nos. 9,125,738, 6,629,534.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

The novel features of the invention are set forth with particularity in the appended claims. A better understanding of the features and advantages of the present invention will be obtained by reference to the following detailed description that sets forth illustrative examples, in which the principles of the invention are utilized, and the accompanying drawings of which:

FIGS. 15A-15E schematically illustrates a method of deploying a prosthetic cardiac valve whereby the first and second anterior tabs are concurrently deployed, according to many examples.

FIGS. 25D1-25D2 show an example of a capsule.

FIGS. 25E1-25E2 show another example of a capsule.

FIGS. 25F1-25F2 show still another example of a capsule.

DETAILED DESCRIPTION

While examples will be discussed primarily with reference to prosthetic mitral valves, one of skill in the art will appreciate this this is not intended to be limiting and the devices disclosed herein may be used in other valves such as aortic valves, pulmonary valves, tricuspid valves, or even other valves such as venous valves.

Numerous surgical methods and devices have been developed to treat mitral valve or other valvular dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvular insufficiency, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed below.

Also, while some of these devices and methods are promising, there still is a need for improved devices and methods that will further allow more accurate delivery and deployment of a prosthetic valve and that will also more securely anchor the valve in place. At least some of these objectives will be met by the examples disclosed herein. Specific examples of the disclosed device, delivery system, and method will now be described with reference to the drawings. Nothing in this detailed description is intended to imply that any particular component, feature, or step is essential to the invention.

Cardiac Anatomy.

Figure 1:
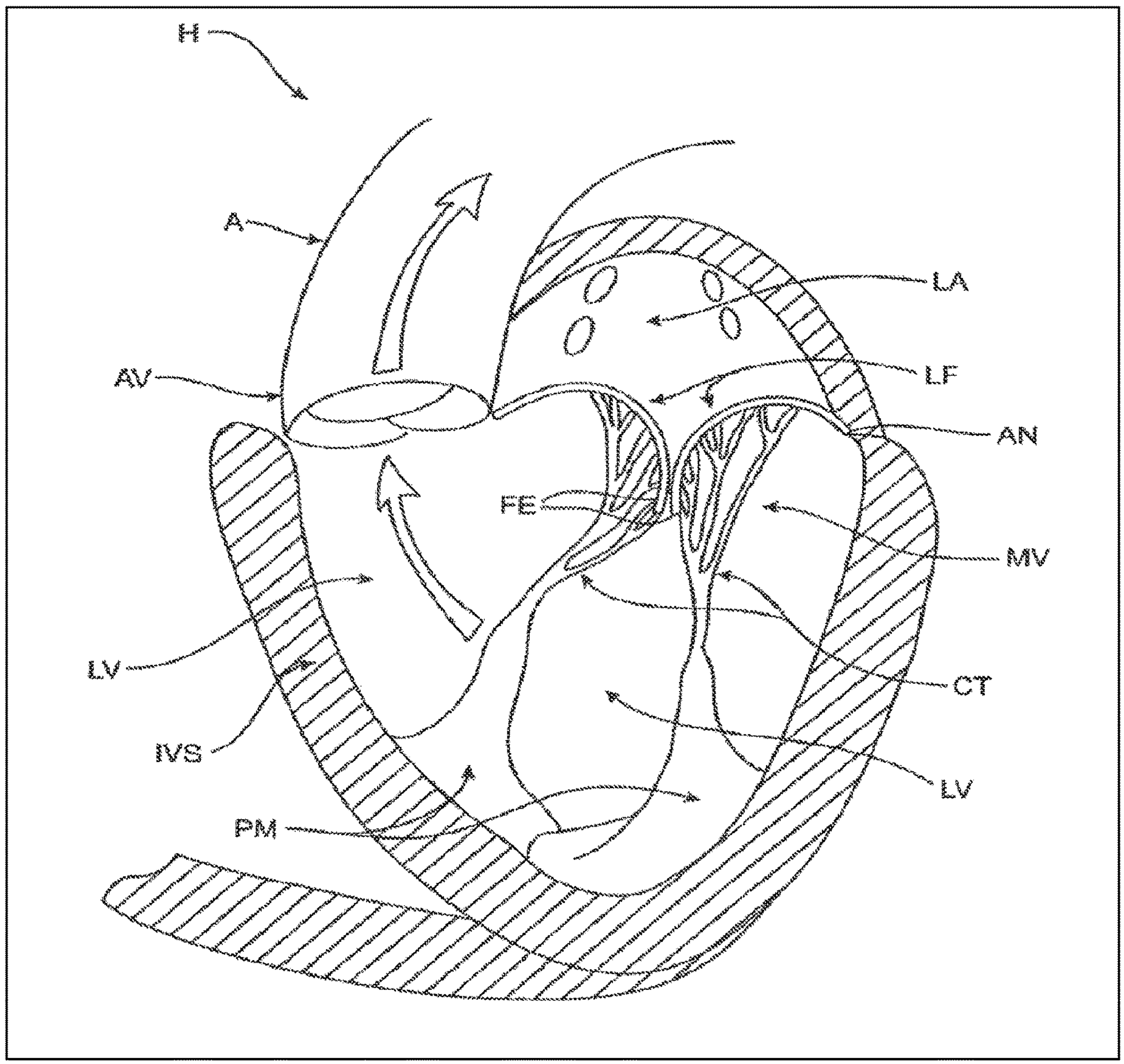
FIG. 1 is a schematic illustration of the left ventricle of a heart showing blood flow during systole with arrows.

The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
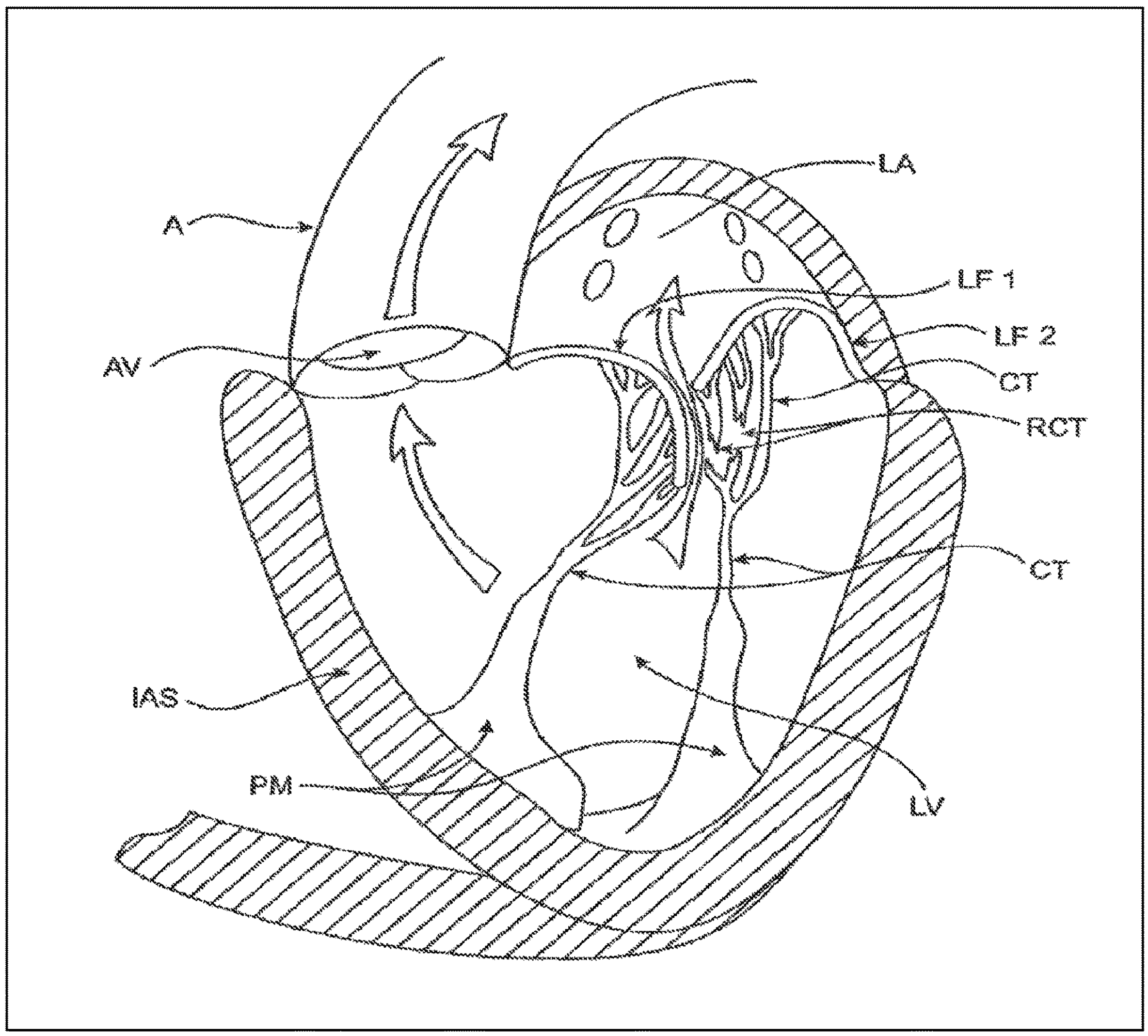
FIG. 2 is a schematic illustration of the left ventricle of a heart having prolapsed leaflets in the mitral valve.
Figure 3:
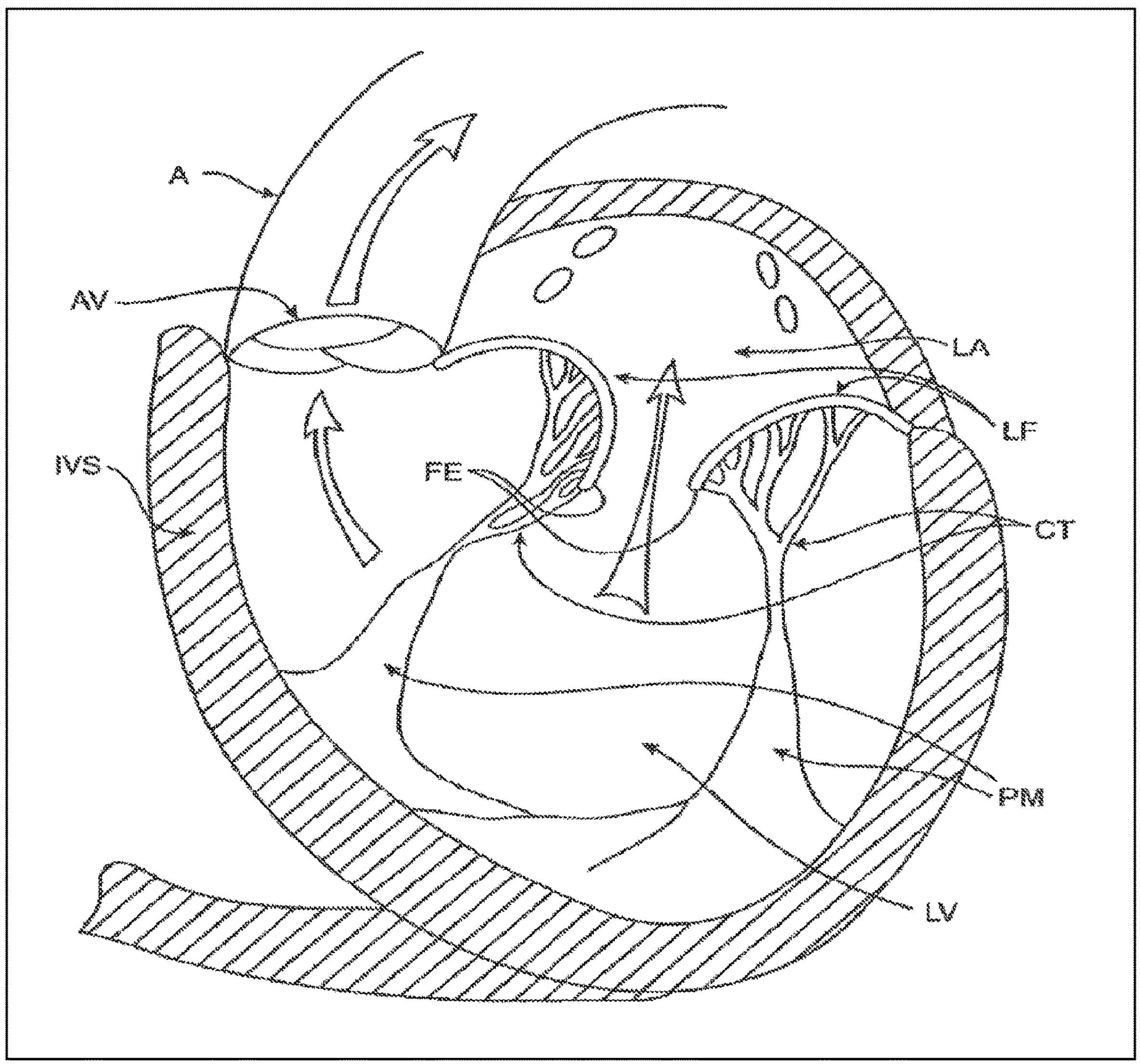
FIG. 3 is a schematic illustration of a heart in a patient suffering from cardiomyopathy where the heart is dilated and the leaflets do not meet.
Figure 4:
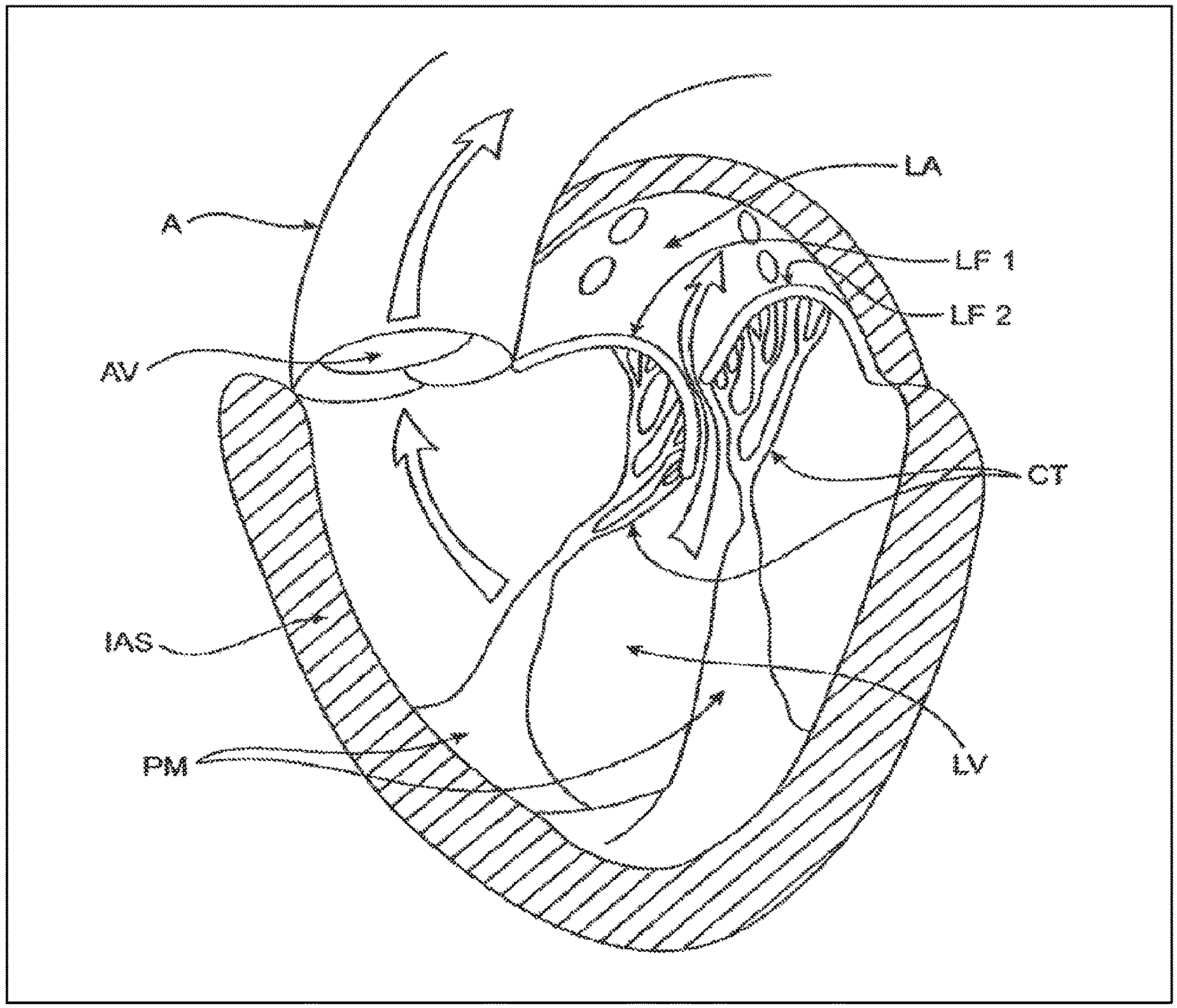
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
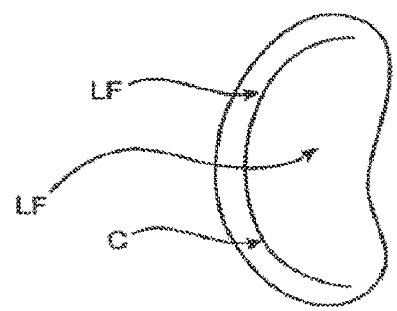
FIG. 3A shows normal closure of the valve leaflets.
Figure 3B:
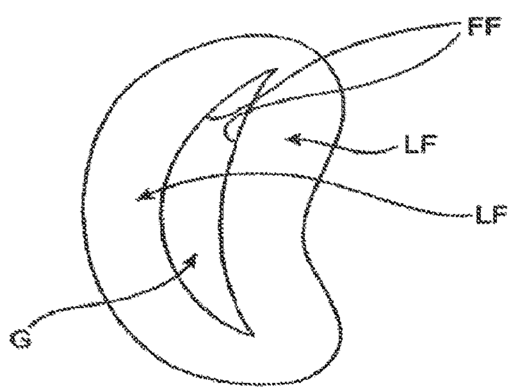
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
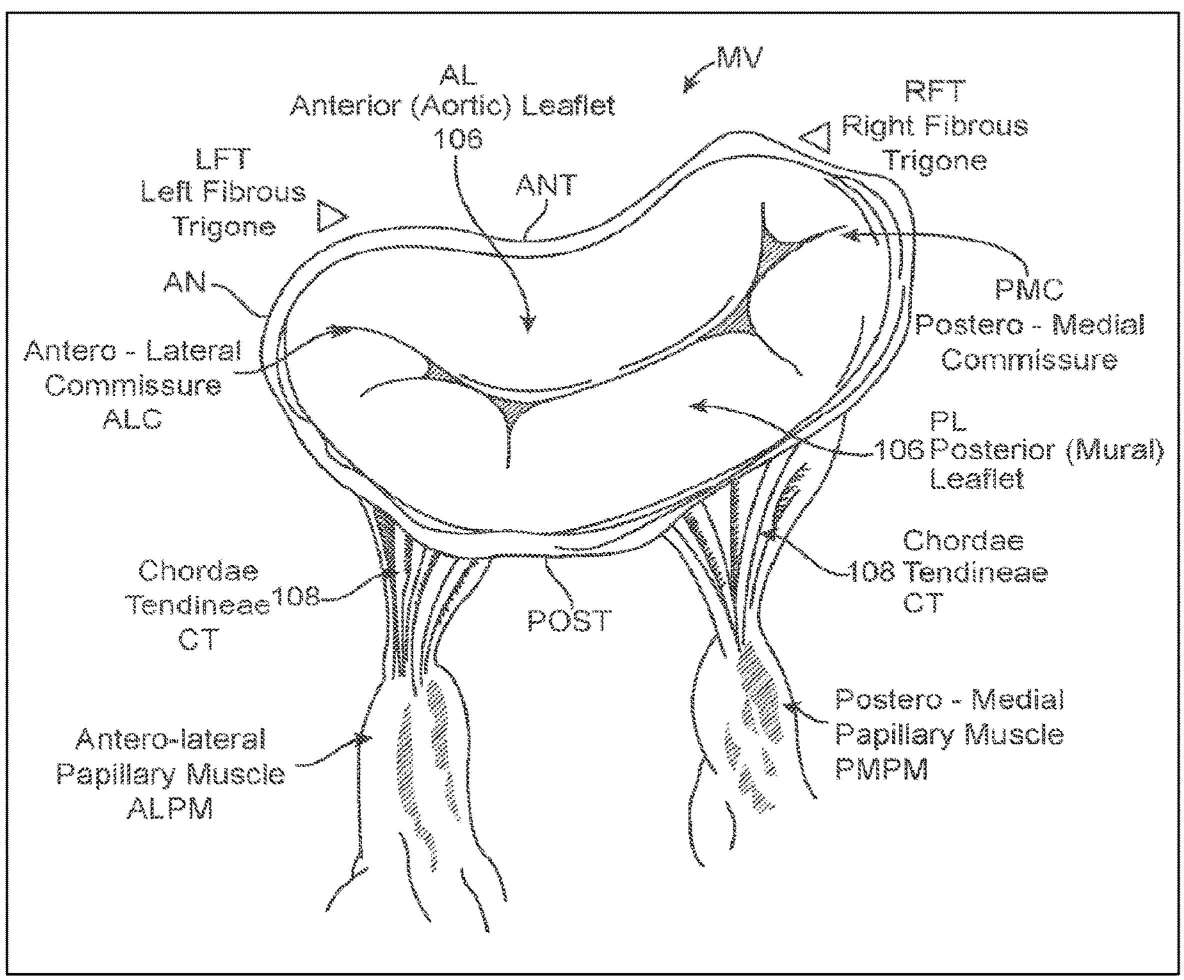
FIGS. 5A-5B illustrate anatomy of the mitral valve.

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT.

Figure 5B:
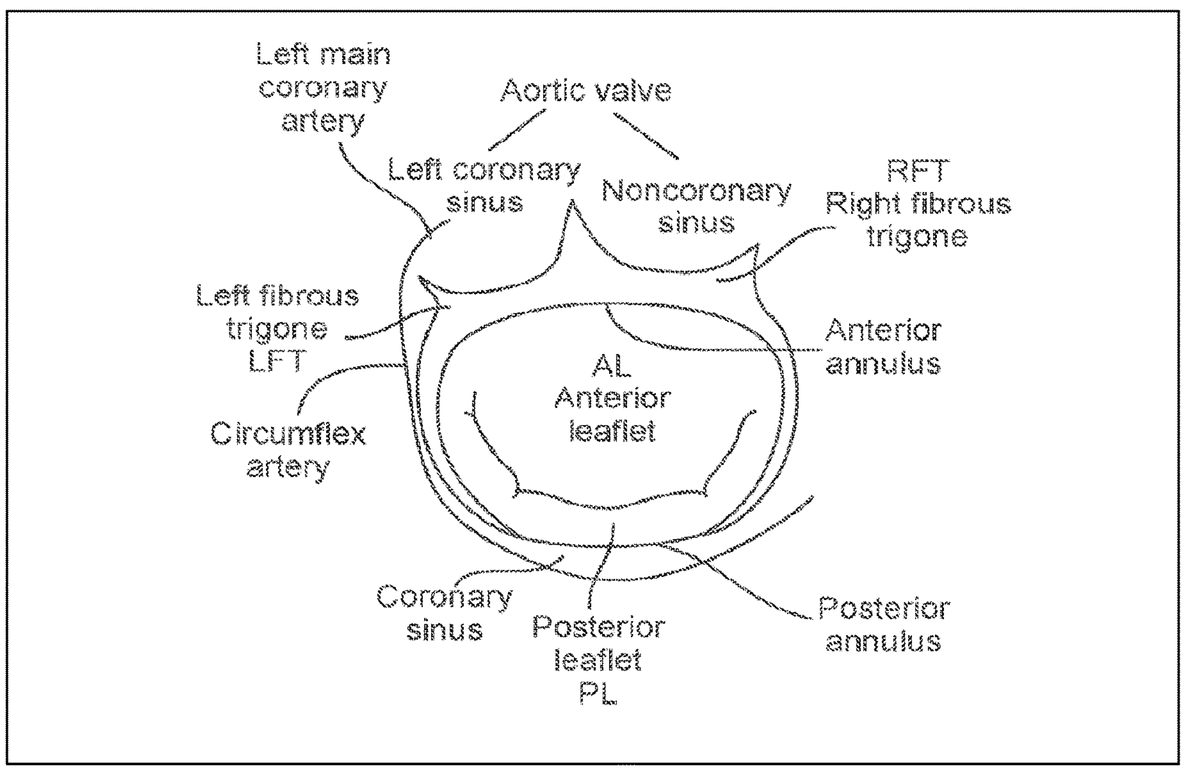

These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the examples disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc., as well as other valves in the body such as venous valves.

Prosthetic Valve.

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for the malfunctioning native valve, thereby reducing or eliminating valvar insufficiency. While some of these valves appear promising, there still is a need for improved valves. Positioning and anchoring the prosthetic valve in the native anatomy remains a challenge. The following specification discloses a prosthetic valve, a delivery system for the prosthetic valve, and methods of delivering the valve that overcome some of the challenges associated with existing prosthetic valves.

Figure 6:
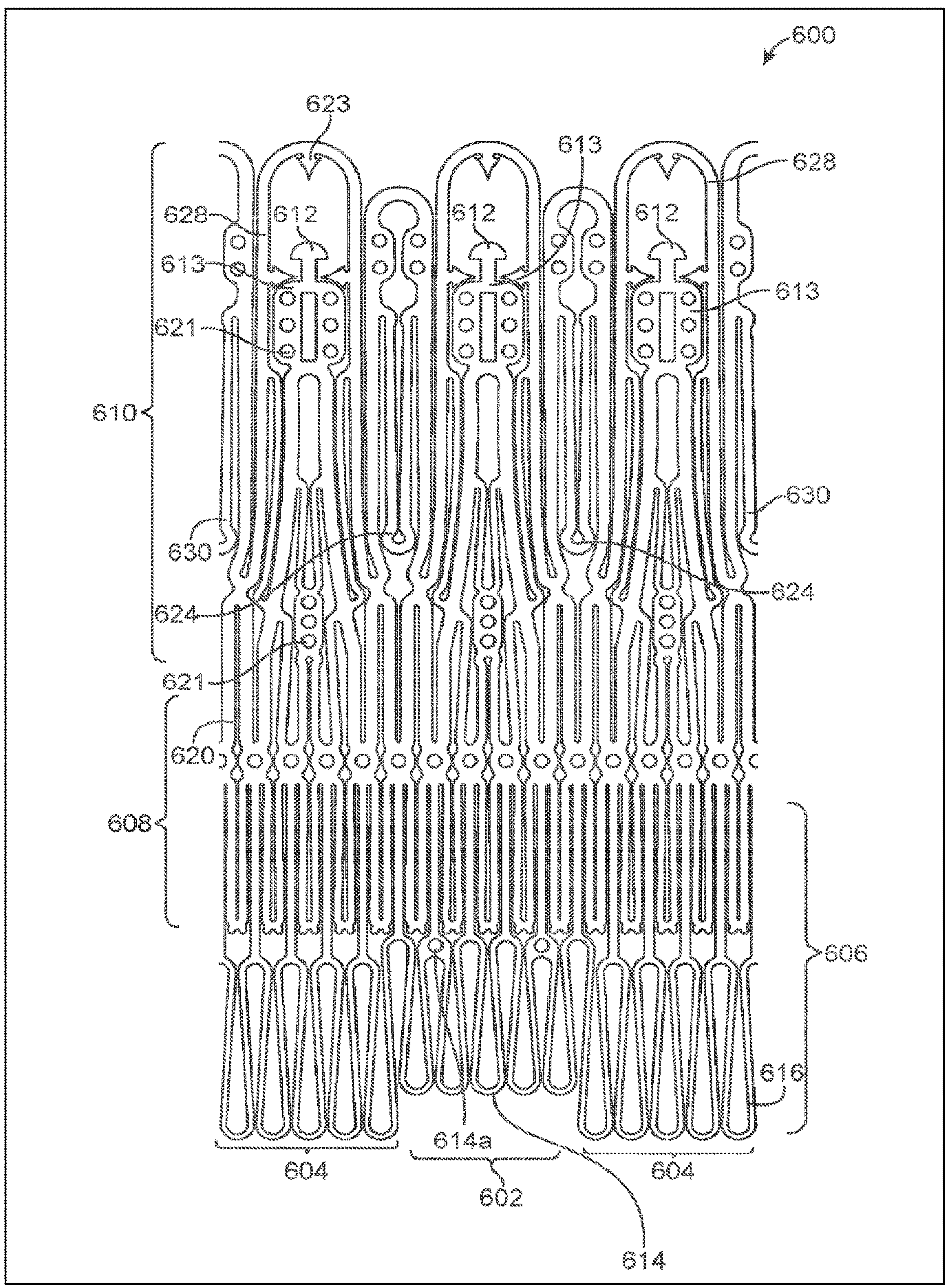
FIG. 6 illustrates an uncovered frame in a prosthetic cardiac valve, with the frame flattened out and unrolled.

FIG. 6 illustrates a prosthetic cardiac valve in the cut and unrolled flat pattern. Coverings from the frame (e.g. fabric or tissue) have been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. The frame is self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skewed relative to one another and thus the resulting cell pattern has an enlarged end and the opposite end tapers to a smaller end. The anterior portion of the atrial skirt does not have a flanged region like the posterior portion, thus the anterior portion 602 of the atrial region may have shorter struts than the posterior region 604. Thus, the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician with visualization of delivery of the prosthetic valve to the mitral valve and with alignment of the prosthetic valve prior to expansion of the prosthetic valve. Optional radiopaque markers 614*a* are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded against the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, the sequence of the deployment of the tabs may be controlled. Thus, in this example, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to more accurately be delivered and more securely anchored into position. For example, either the anterior tab(s) or the posterior tab(s) may be more easily visualized than the other in at least some cases, and the more easily visualized tab may be configured to deploy first as a guide to orient the frame during implantation. In at least some cases, the Inventors have found that the posterior tab is easier to visualize using ultrasound and/or fluoroscopy. The sequence of tab deployment may be customized to the individual patient and their anatomy in some cases and the customization may be based on pre-screening imaging data for the individual patient. The tabs that are projected to be more easily visualized, such as by using ultrasound and/or fluoroscopy, may be configured to deploy first. The initially deployed tabs can allow for intermediate movement of the imaging source, e.g., the C-arm controlling the ultrasound or X-ray device for fluoroscopy, so as to provide verification of the initial tab placements. If needed, the prosthetic valve may be repositioned and/or reoriented with the initial tab(s) deployed (and the remaining tab(s) yet to be deployed) based on the imaging or visualization. To further improve the visibility of the tabs, the length and/or curvature of one or more of the tabs may be customized for the individual patient and their anatomy. The length and/or curvature of the one or more tabs may be customized to provide an optimum fit for the individual patient's anatomy, such as the deployment area behind the valve leaflet(s) and/or the chordae tendinae.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting.

The frame may be formed by electrical discharge machining (EDM), laser cutting, photochemical etching, or other techniques known in the art. Hypodermic tubing or flat sheets may be used to form the frame. Once the frame has been cut and formed into a cylinder (if required), it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the prosthesis to self-expand into its unbiased pre-set shape. In other forms, an expandable member such as a balloon may be used to radially expand the prosthesis into its expanded configuration.

Figure 7:
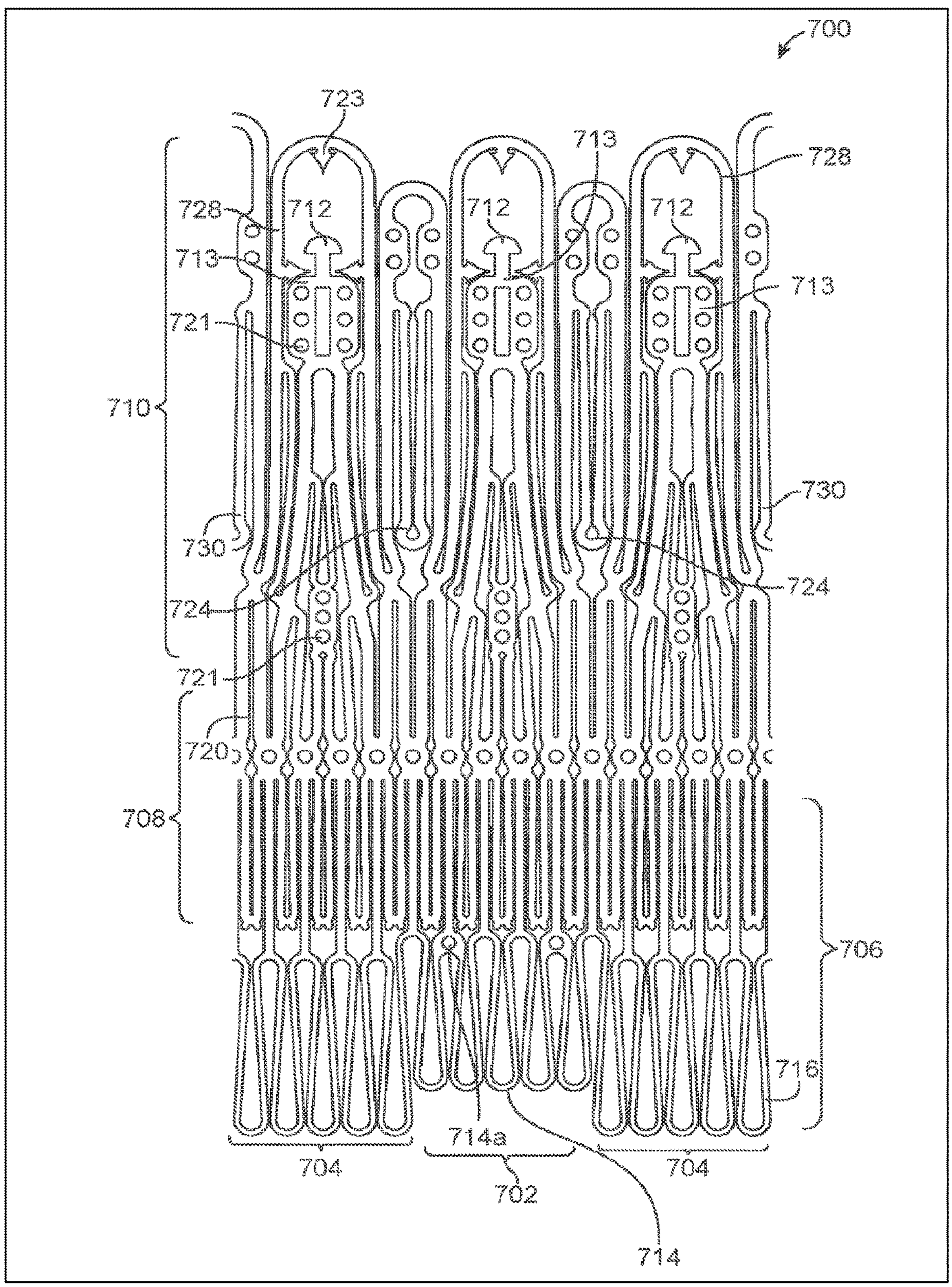
FIG. 7 illustrates another an uncovered frame in a prosthetic cardiac valve, with the frame flattened out and unrolled.

FIG. 7 illustrates another example of a prosthetic cardiac valve in the flat and unrolled cut pattern, and similar to the previous example with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Some examples are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skewed relative to one another and thus the resulting cell pattern has an enlarged end and the opposite end tapers to a smaller end. An anterior portion 702 of the atrial region has shorter struts than the posterior region 704. Thus, the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714*a* are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and against the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus, in this example, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish its radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above with respect to FIG. 6.

Figure 8:
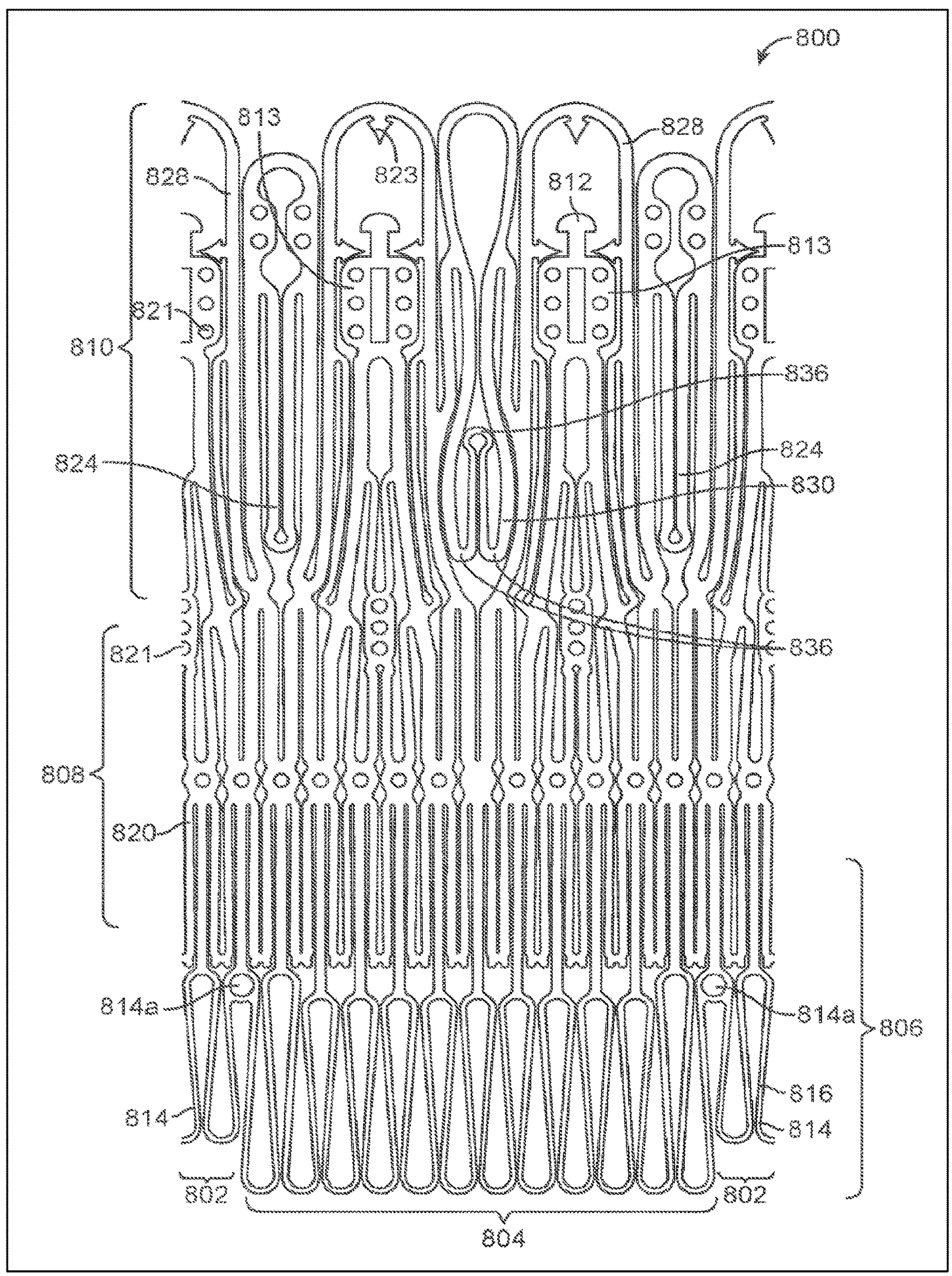
FIG. 8 illustrates still another uncovered frame in a prosthetic cardiac valve, with the frame flattened out and unrolled.

FIG. 8 illustrates another form of a prosthetic cardiac valve in the flat, unrolled cut pattern, and is similar to the previous examples, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. Here, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Examples are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skewed relative to one another and thus the resulting cell pattern has an enlarged end and the opposite end tapers to a smaller end. An anterior portion 802 of the atrial region has shorter struts than the posterior region 804. Thus, the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814*a* are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and against the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this example, the posterior tab comprises four interconnected struts as opposed to two interconnected struts. Thus, in this example the plurality of interconnected struts contain three hinged regions 836 along the tab. Upon expansion of the posterior tab, the hinged regions will also expand, thereby showing an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior tab may be substituted with any of the other posterior tabs described in this specification.

By controlling strut length or axial position of the anterior or posterior tabs along the frame, deployment of the tabs may be controlled. Thus, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be shown similarly as described above.

Figure 9A:
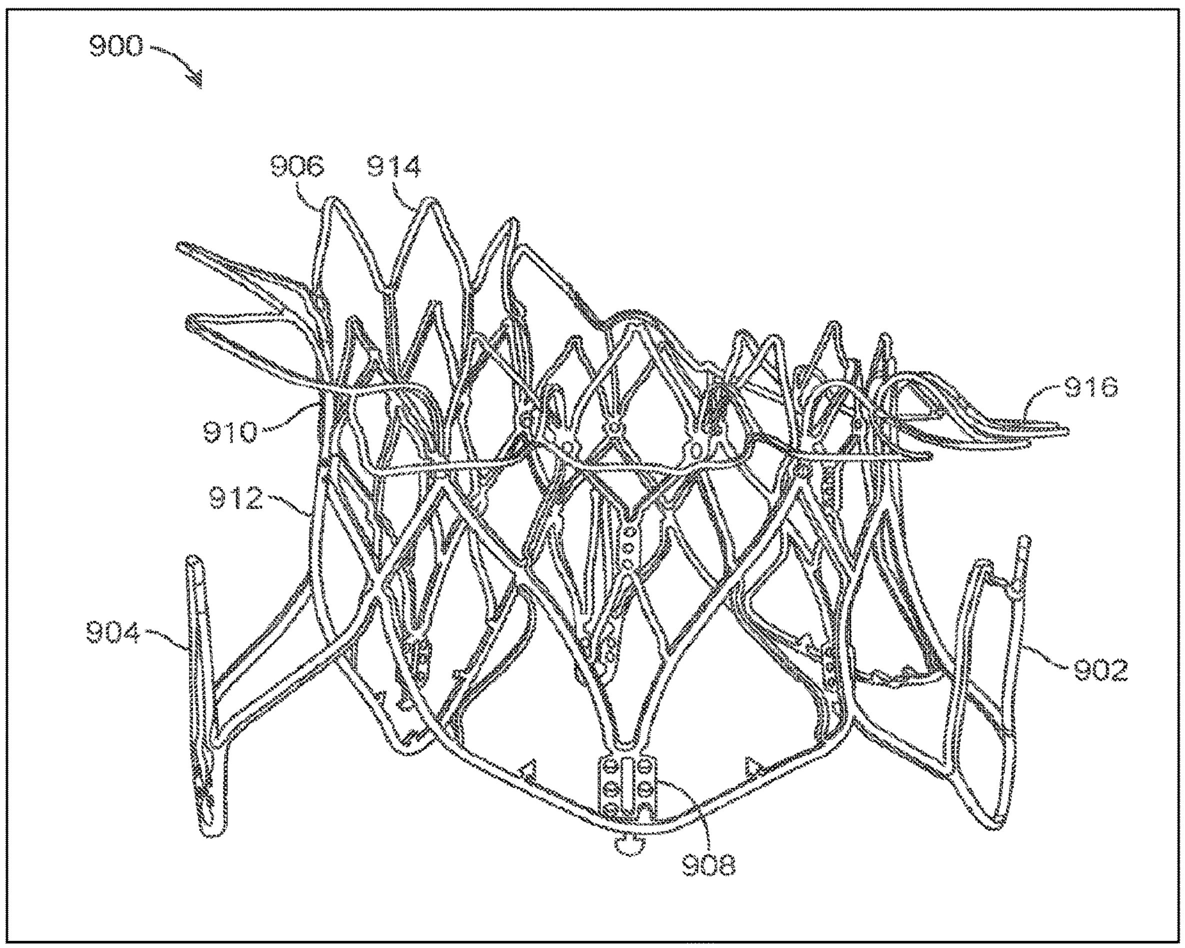
FIG. 9A illustrates a perspective view of an uncovered frame in a prosthetic cardiac valve after it has expanded.
Figure 9B:
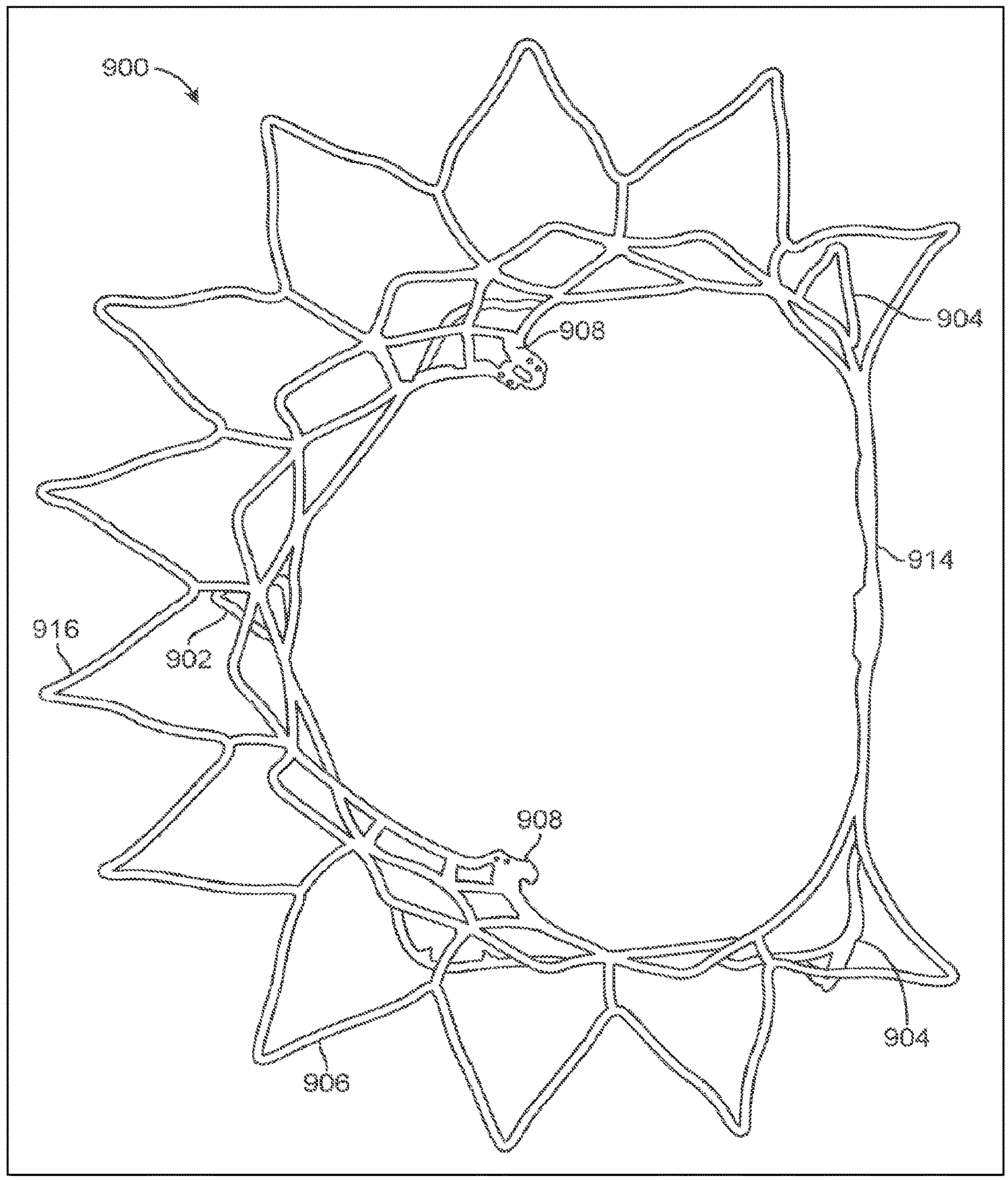
FIG. 9B illustrates a top view of the structure in FIG. 9A.

FIG. 9A illustrates the frame 900 of a prosthetic cardiac valve after it has expanded. Any of the frame examples described above may take this form as each of the above frames have similar geometry but they expand in different order. The frame includes the atrial skirt 906 with anterior portion 914 and posterior portion 916. A flanged region is disposed around the posterior portion and the anterior portion remains flangeless. Additionally, the anterior portion is generally flat, while the posterior portion is cylindrically shaped, thereby showing a D-shaped cross-section which accommodates the mitral valve anatomy. FIG. 9B is a top view of the structure in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and an outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel shown by the frame. The commissure posts are used to hold the prosthetic mitral valve leaflets. The overall shape of the expanded frame is D-shaped, with the anterior portion flat and the posterior portion cylindrically shaped.

Figure 10:
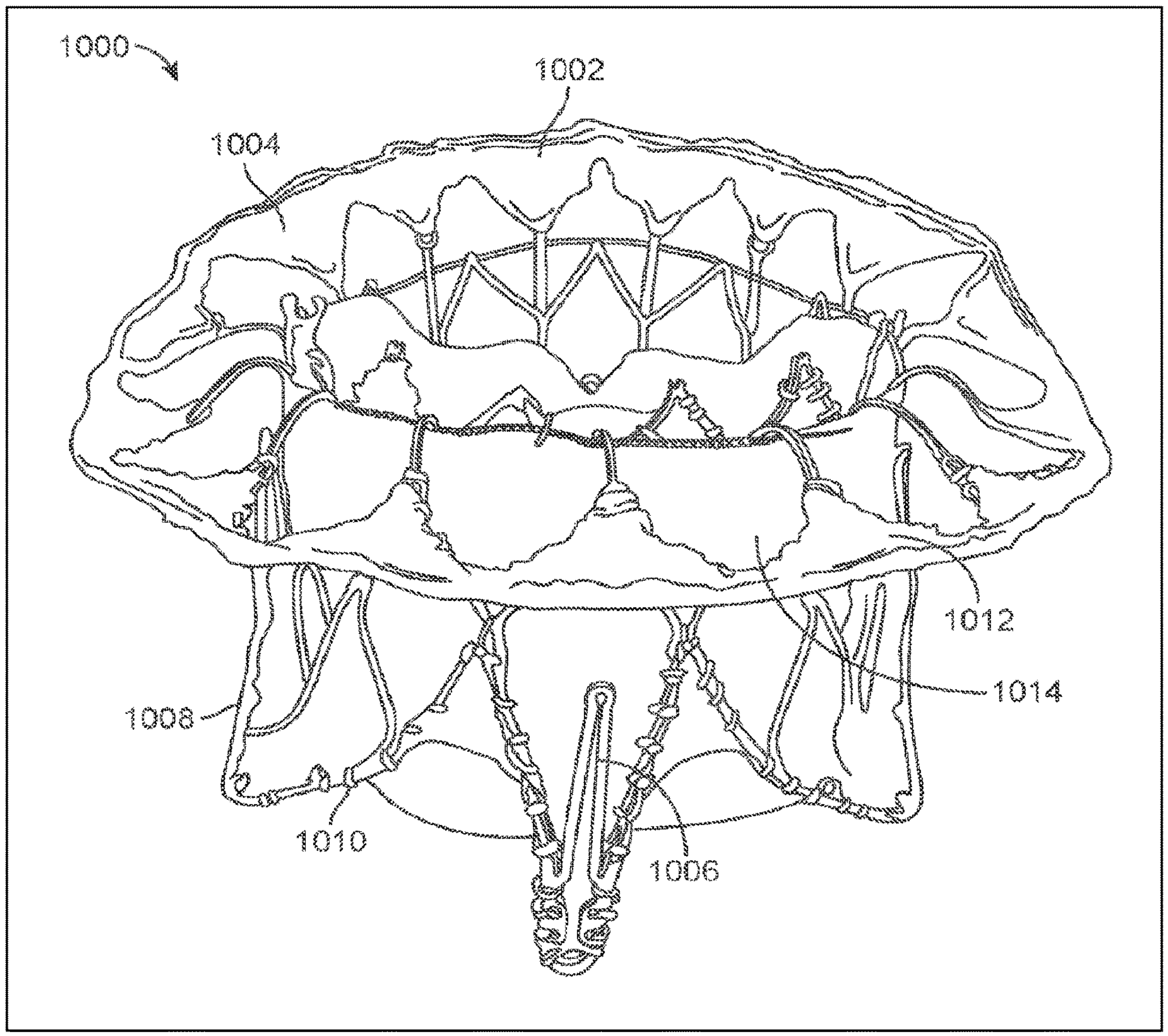
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby showing the prosthetic cardiac valve 1000. The atrial skirt may be entirely covered by a material, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Delivery System.

FIGS. 11A-11D illustrate an example of a delivery system that may be used to deliver any of the prosthetic cardiac valves disclosed in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
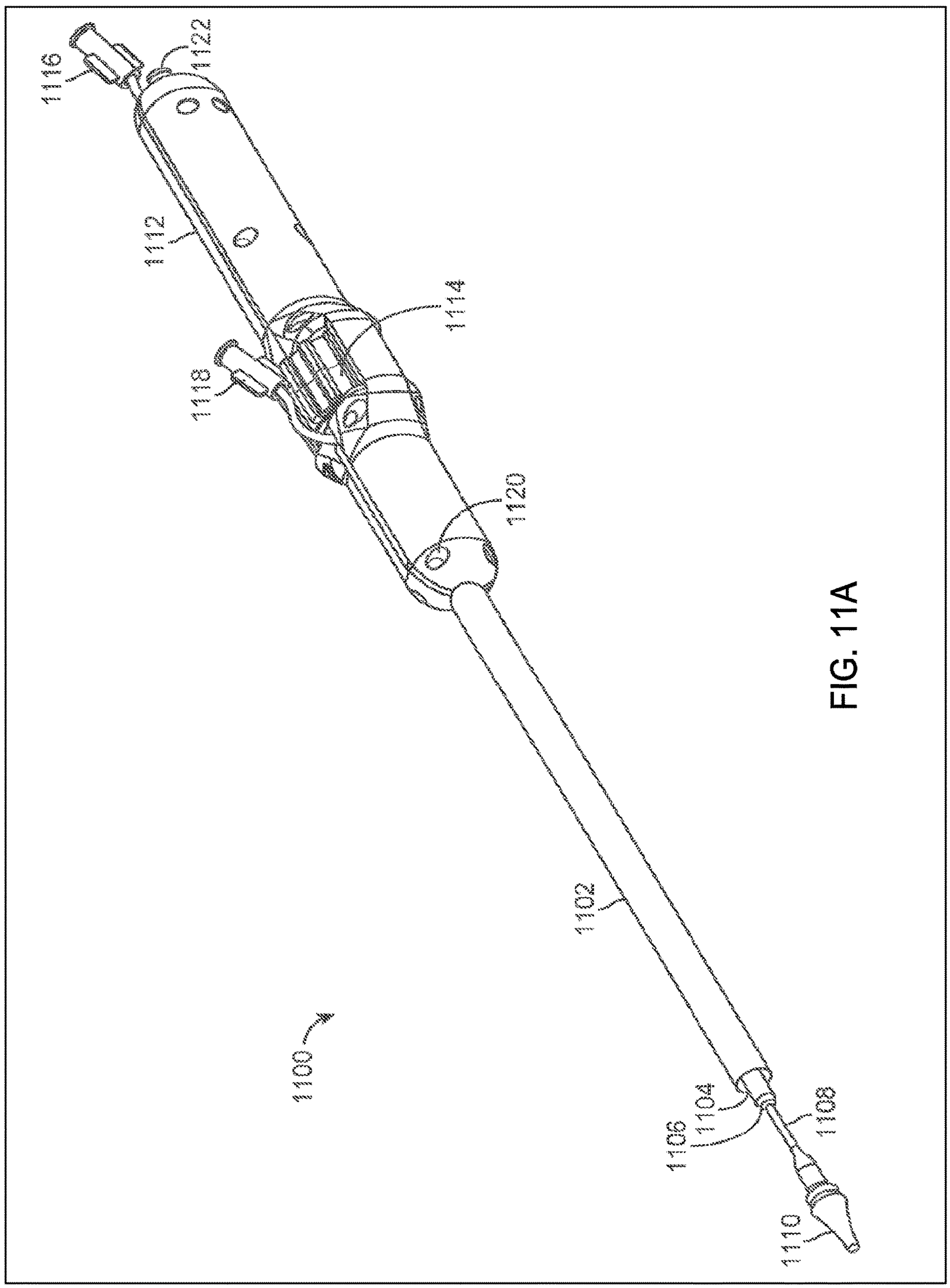
FIGS. 11A-11D illustrate a delivery system used to transapically deliver a prosthetic cardiac valve.
Figure 11B:
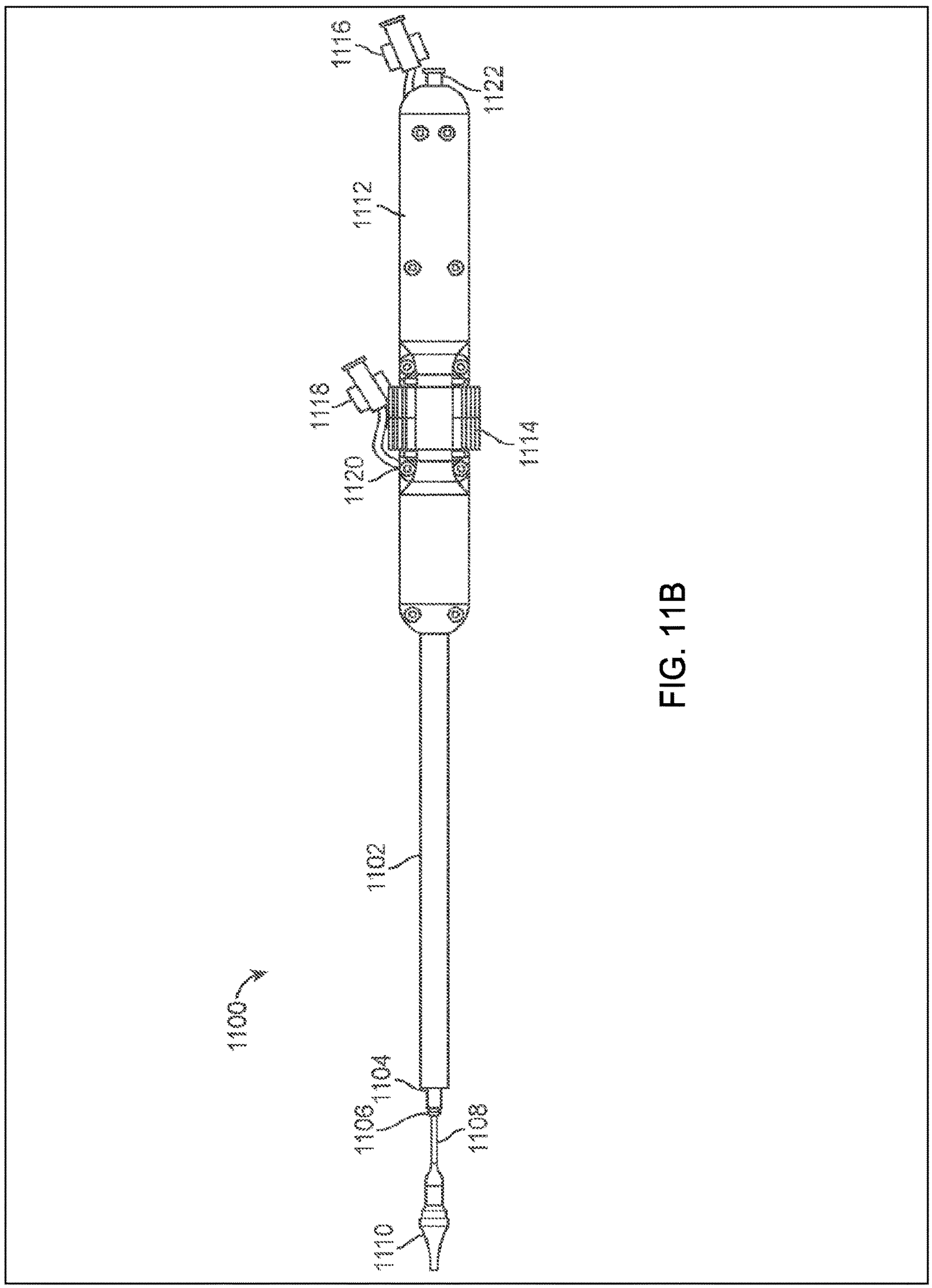

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with Luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an O-ring or other material. Luer connector 1122 allows flushing of the guidewire lumen and a hemostatic valve such as a Tuohy-Borst may be coupled to the Luer connector to allow a guidewire to be advanced through the guidewire catheter shaft while maintaining hemostasis. Screws 1120 keep the handle housing coupled together. FIG. 11B illustrates a side view of the delivery system 1100.

Figure 11C:
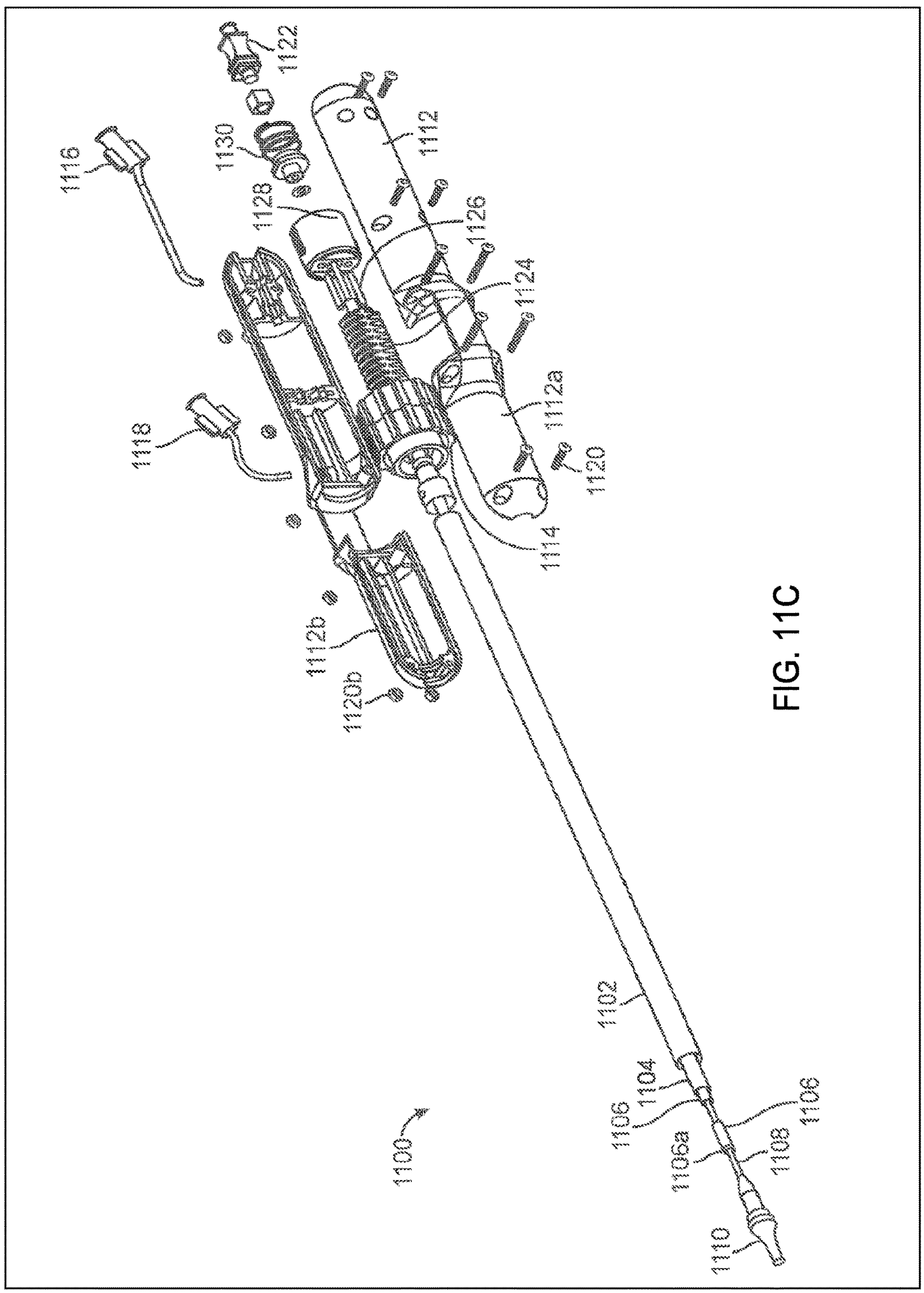

FIG. 11C is a partial exploded view of the delivery system 1100 and more clearly illustrates the components in the handle 1112 and how they interact. The handle 1112 includes a housing having two halves 1112*a*, 1112*b* which hold all the components. The handle is preferably held together with screws 1120 and nuts 1120*b*, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106*a* on the distal portion of hub catheter 1106 and then the bell catheter shaft is disposed thereover, thereby releasably engaging the commissures with the delivery catheter. Once other portions of the prosthetic cardiac valve have expanded, the commissures may be released.

Figure 11D:
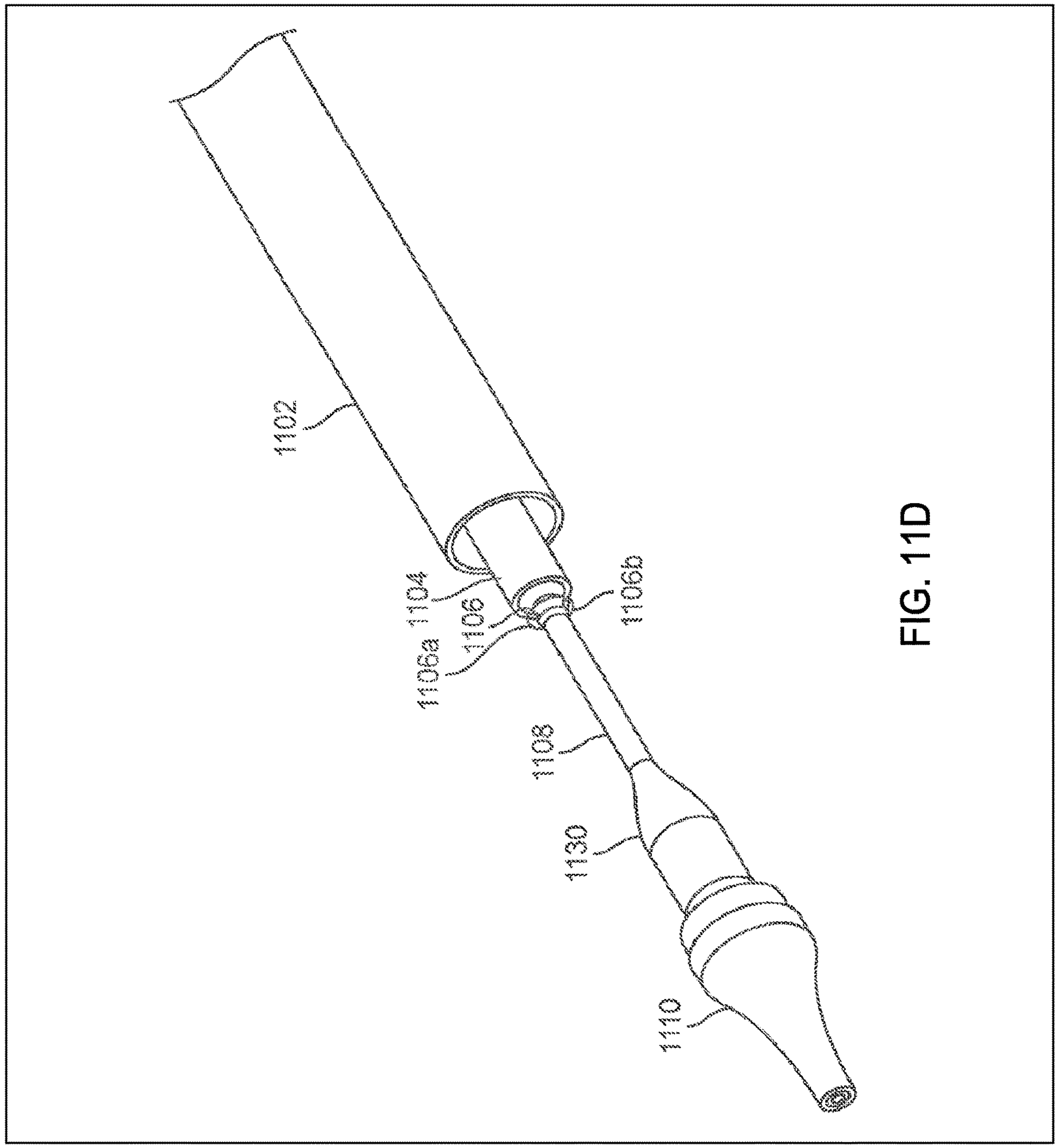

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106*a* having slots 1106*b* that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Delivery Method.

A number of methods may be used to deliver a prosthetic cardiac valve to the heart. methods of delivering a prosthetic mitral valve may include a transluminal delivery route which may also be a transseptal technique which crosses the septum between the right and left sides of the heart, or in other examples, a transapical route may be used such as illustrated in FIGS. 12A-12L. The delivery device previously described above may be used to deliver any of the prosthetic valves described herein, or other delivery devices and other prosthetic valves may also be used, such as those disclosed in U.S. patent application Ser. No. 13/096,572, previously incorporated herein by reference. However, in this example, the prosthetic cardiac valve of FIG. 6 is used so that the anterior tabs deploy first, followed by the posterior tab, and then the ventricular skirt.

Figure 12A:
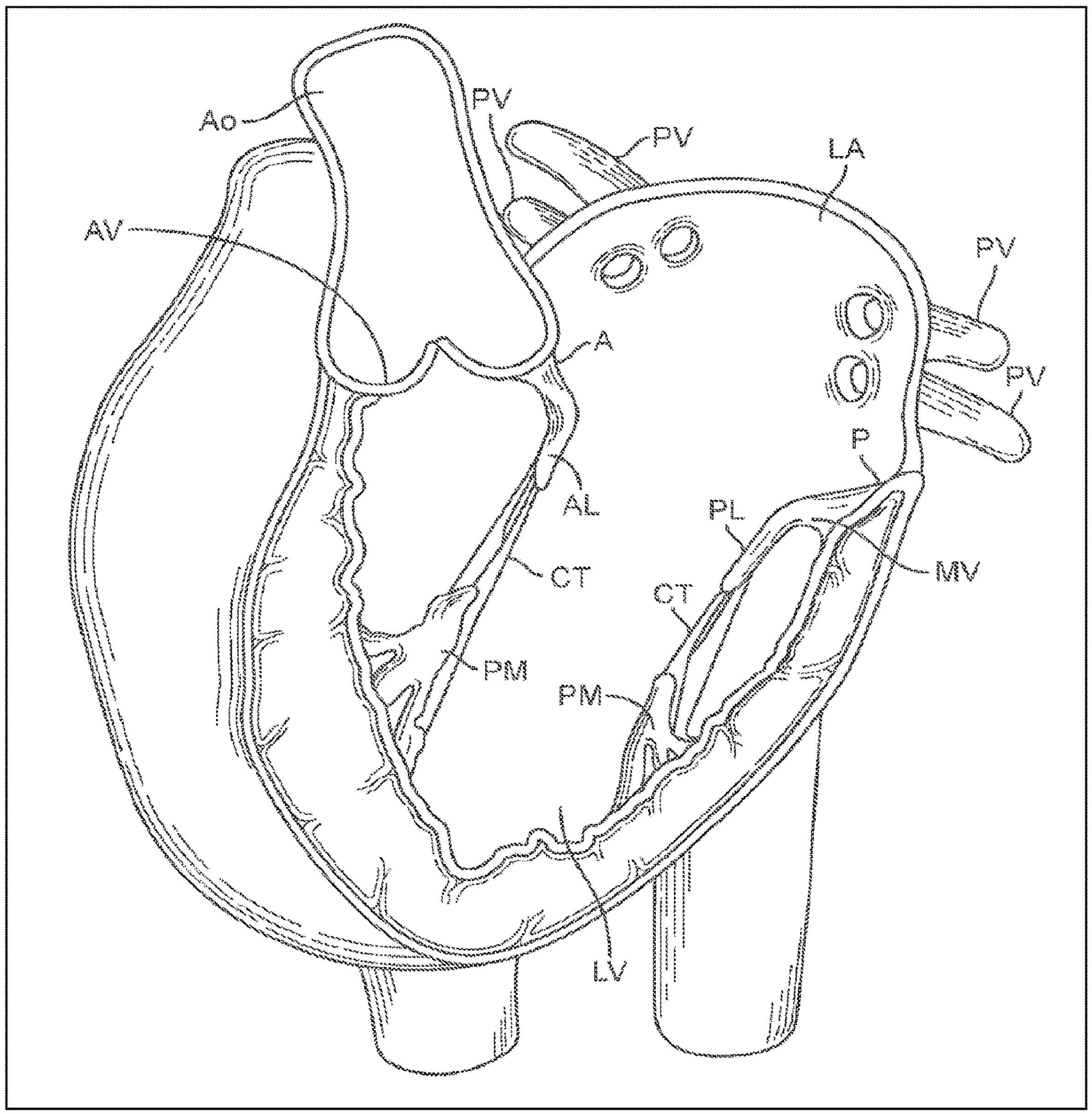
FIGS. 12A-12L illustrates a method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
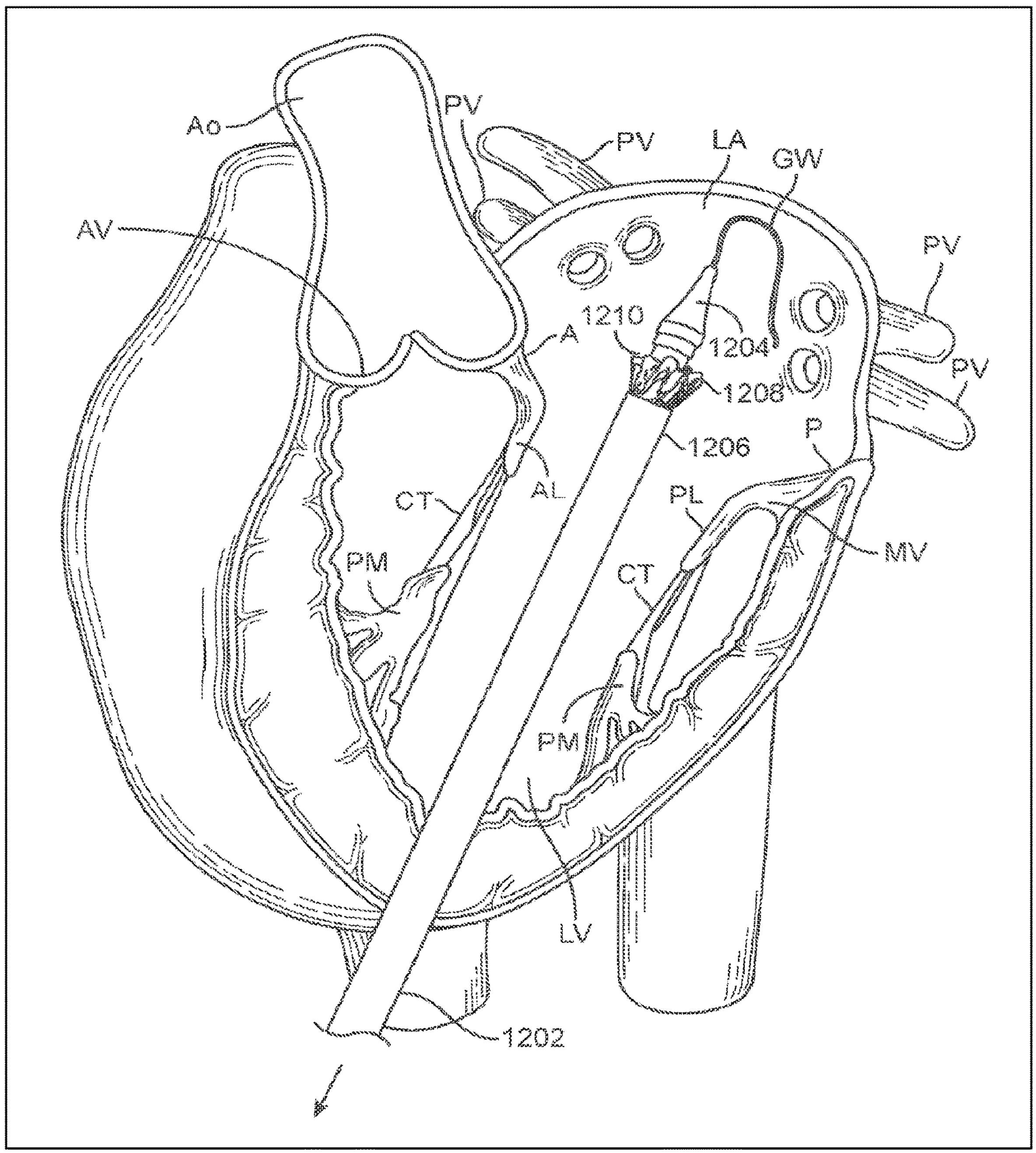
Figure 12C:
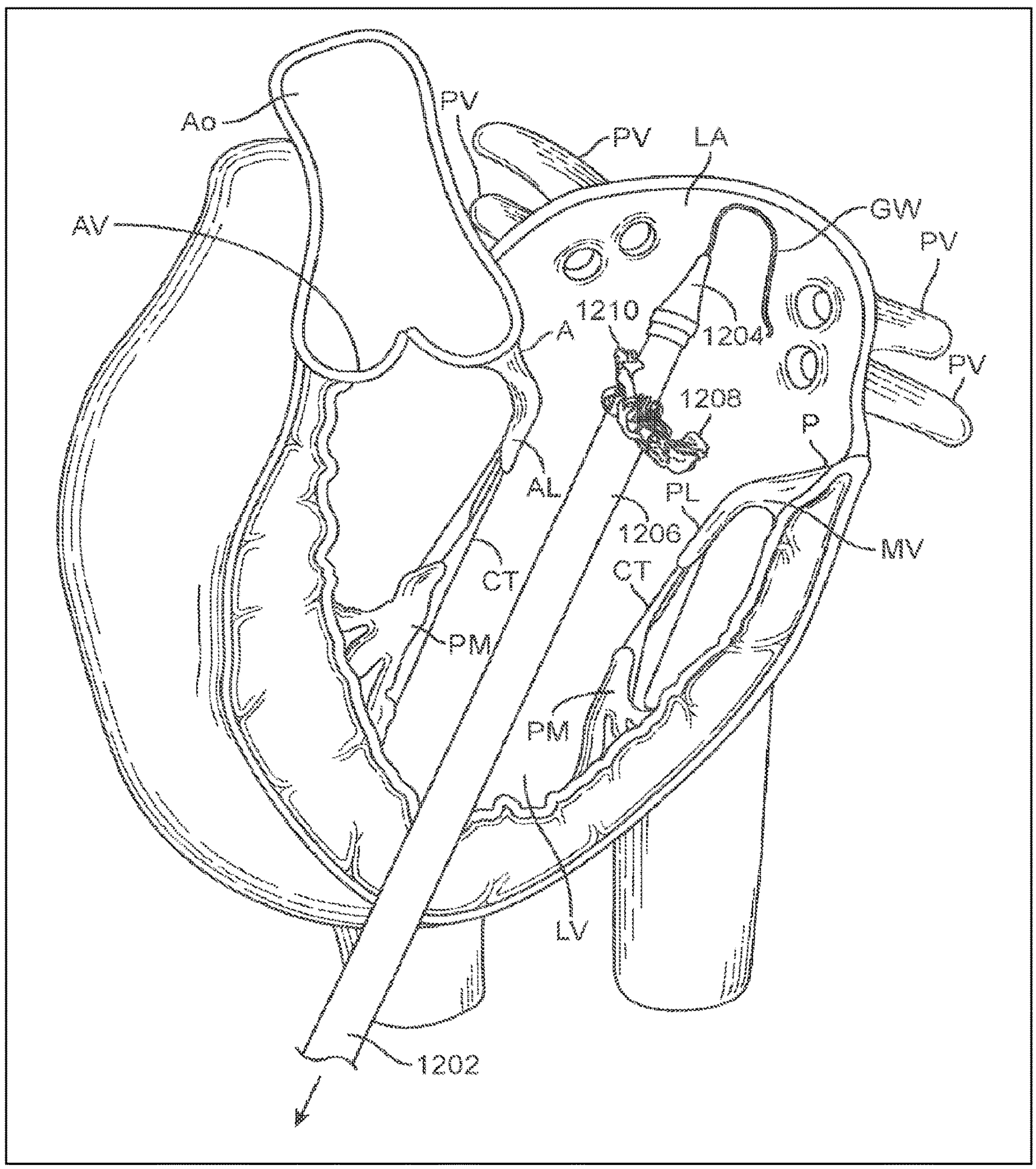
Figure 12D:
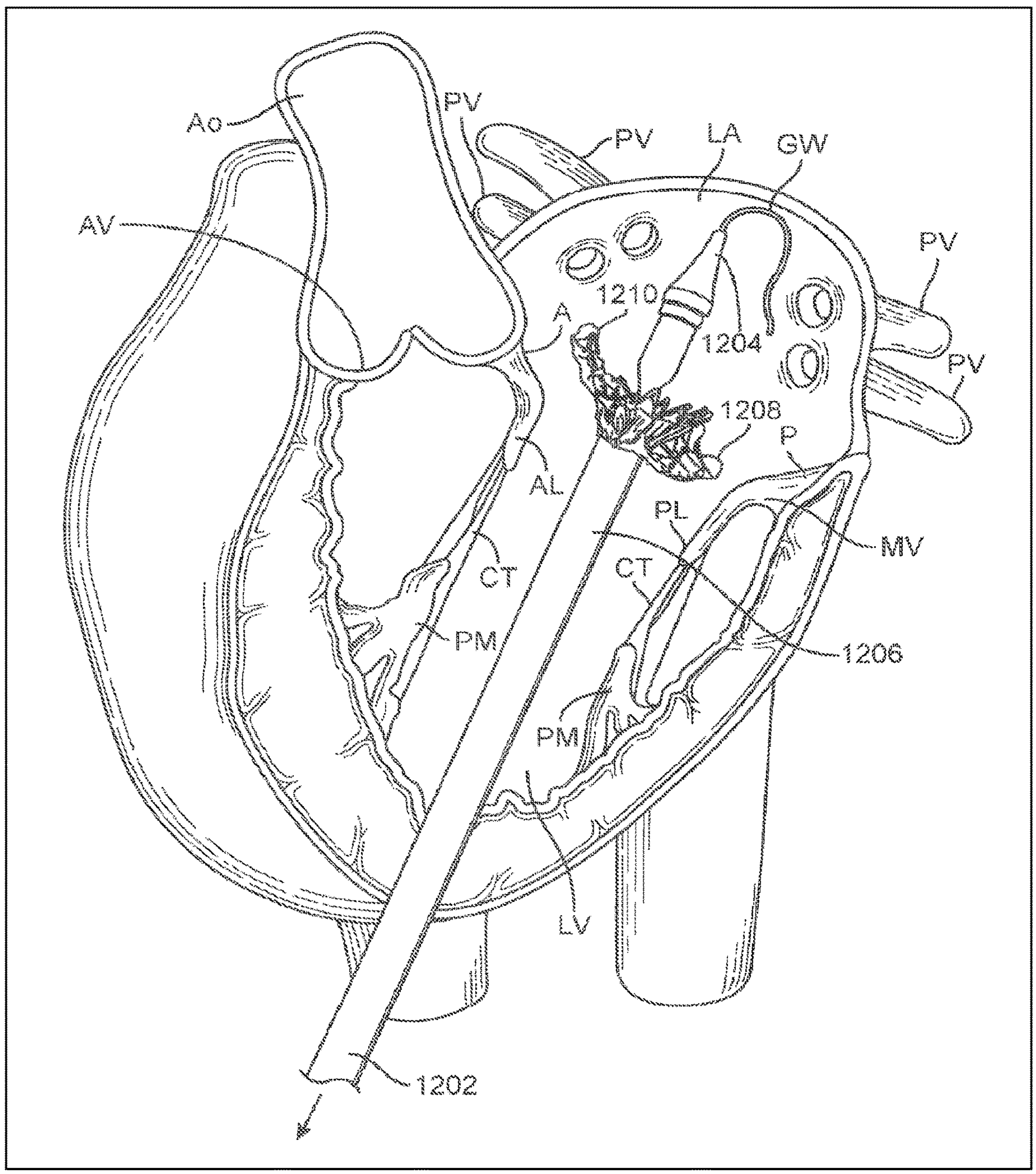

FIG. 12B illustrates transapical delivery of a delivery system 1202 through the apex of the heart into the left atrium LA via the left ventricle LV. The delivery system 1202 may be advanced over a guidewire GW into the left atrium, and a tissue penetrating tip 1204 helps the delivery system pass through the apex of the heart by dilating the tissue and showing a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. The atrial skirt disposes a flange that rests against a superior surface of the mitral valve and this anchors the prosthetic valve and prevents it from unwanted movement downstream into the left ventricle.

Figure 12E:
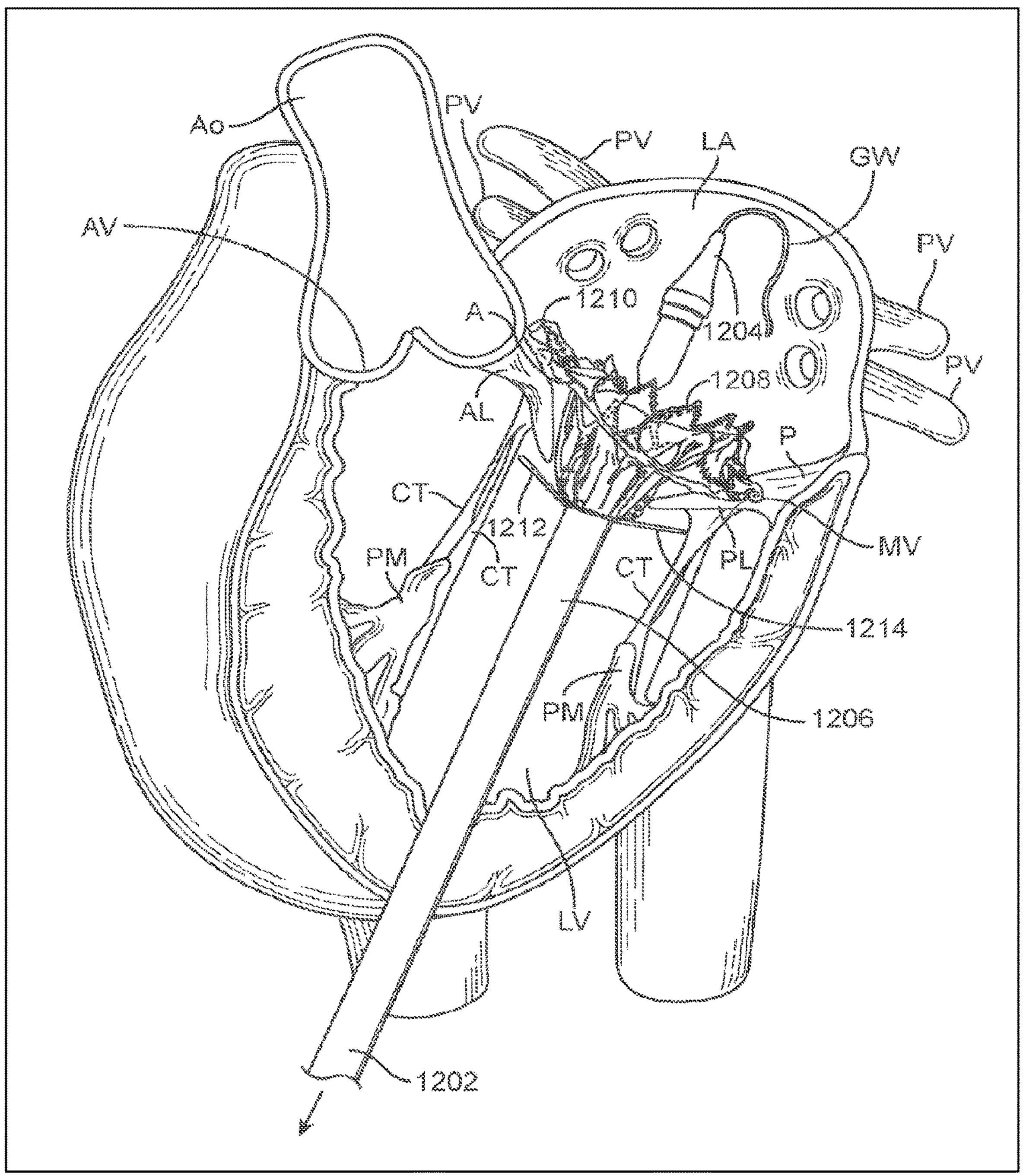
Figure 12F:
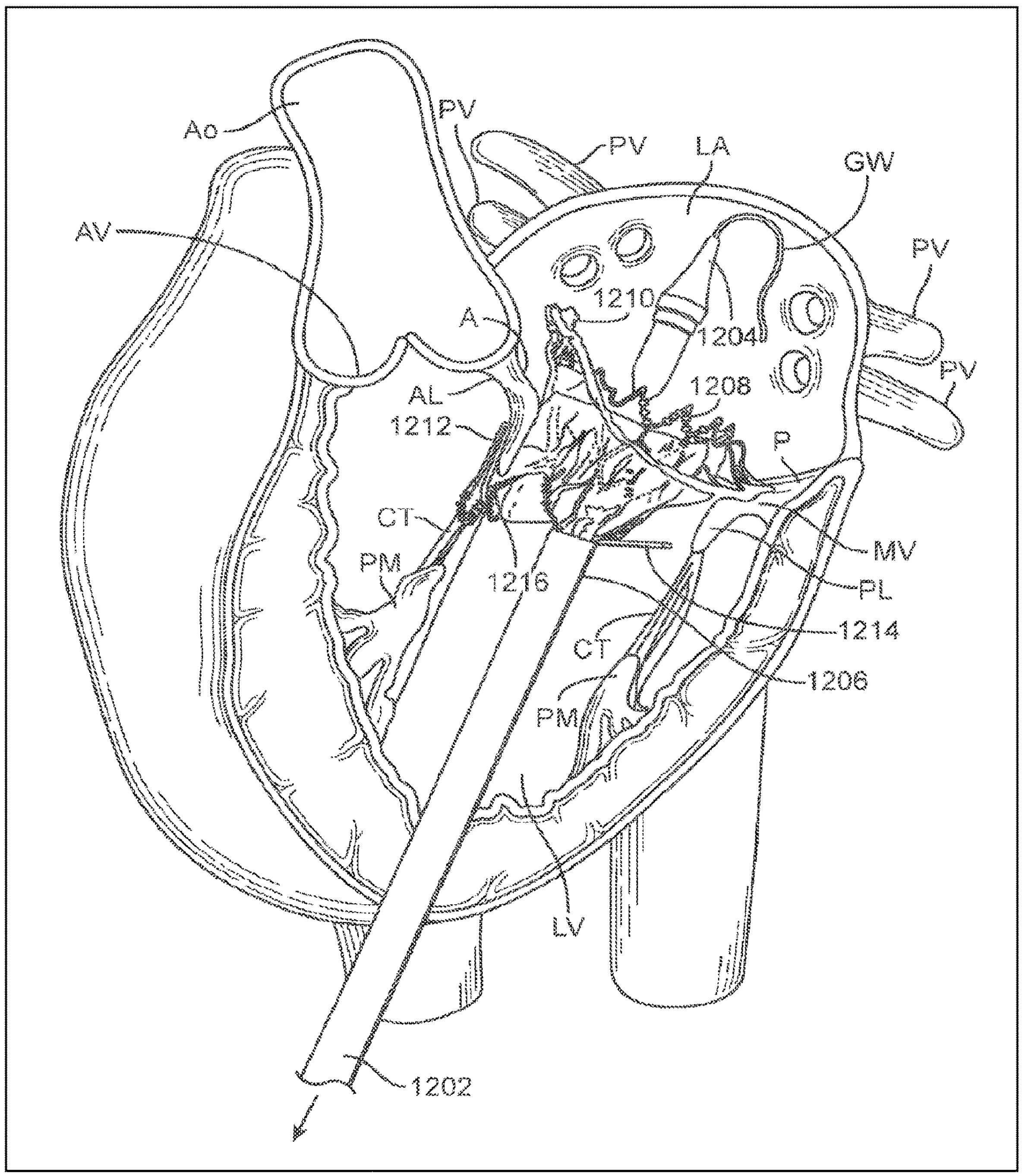

As the outer sheath 1206 continues to be proximally retracted, the annular region of the prosthetic cardiac valve self-expands within the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this example, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
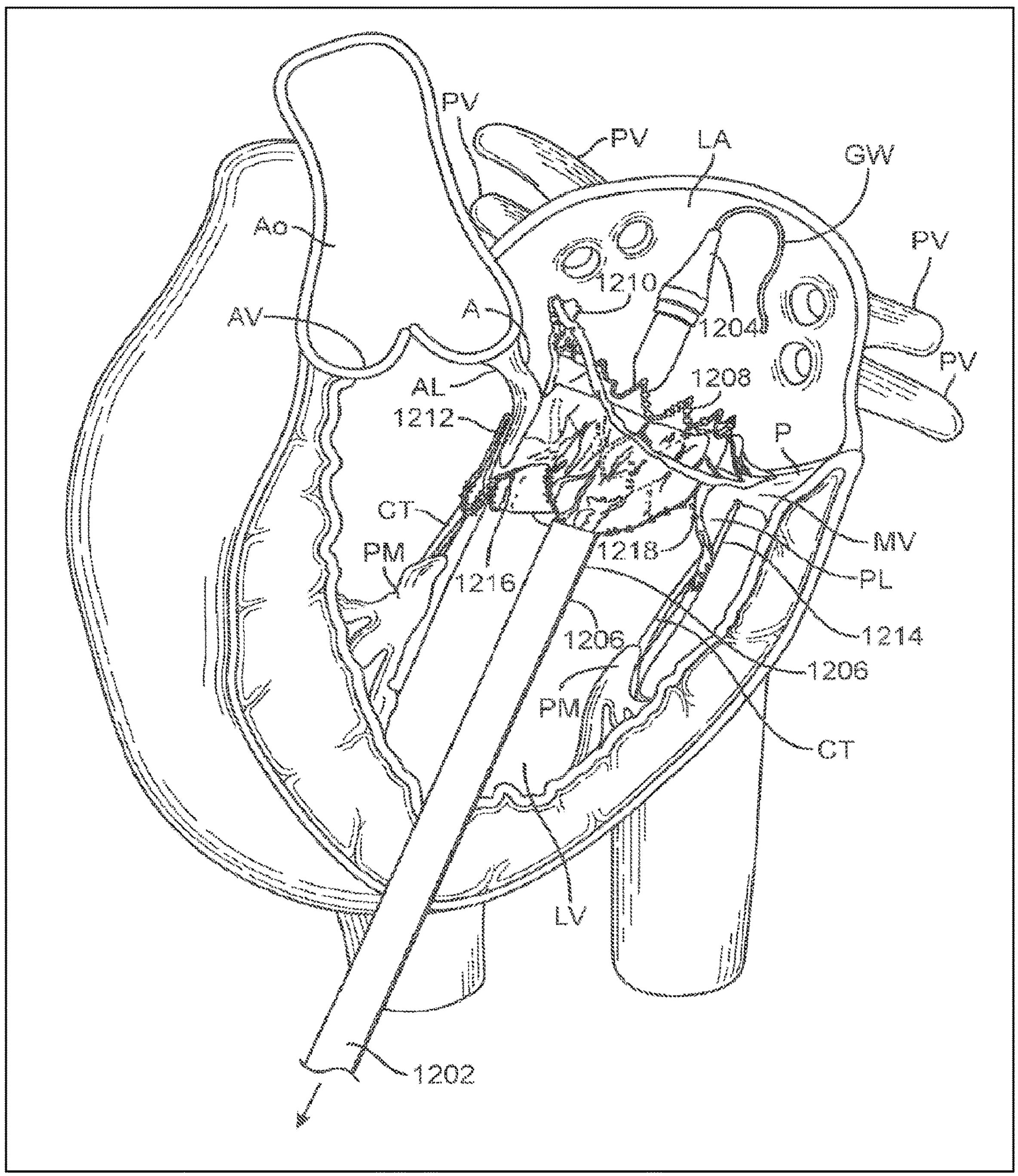
Figure 12H:
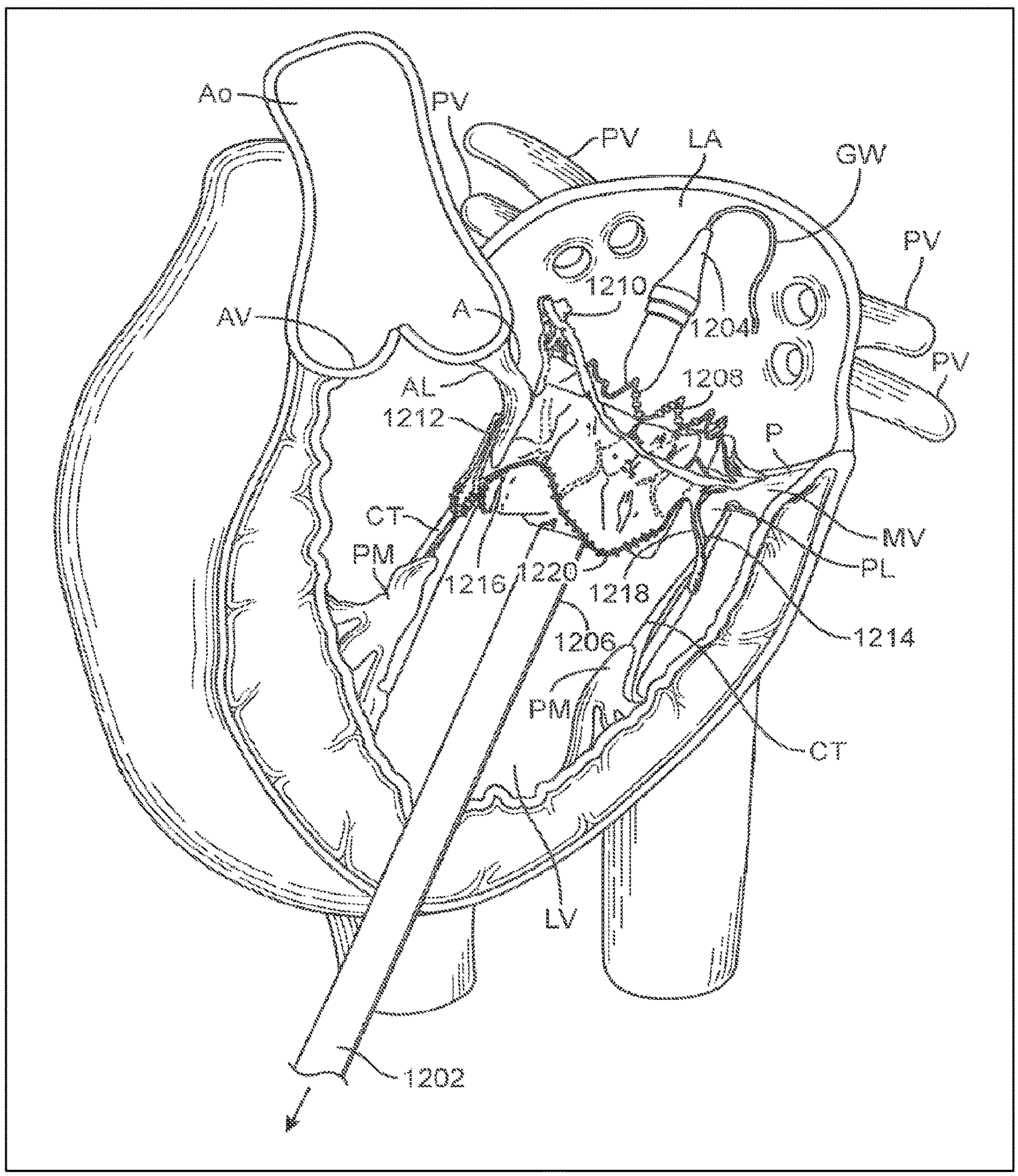

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
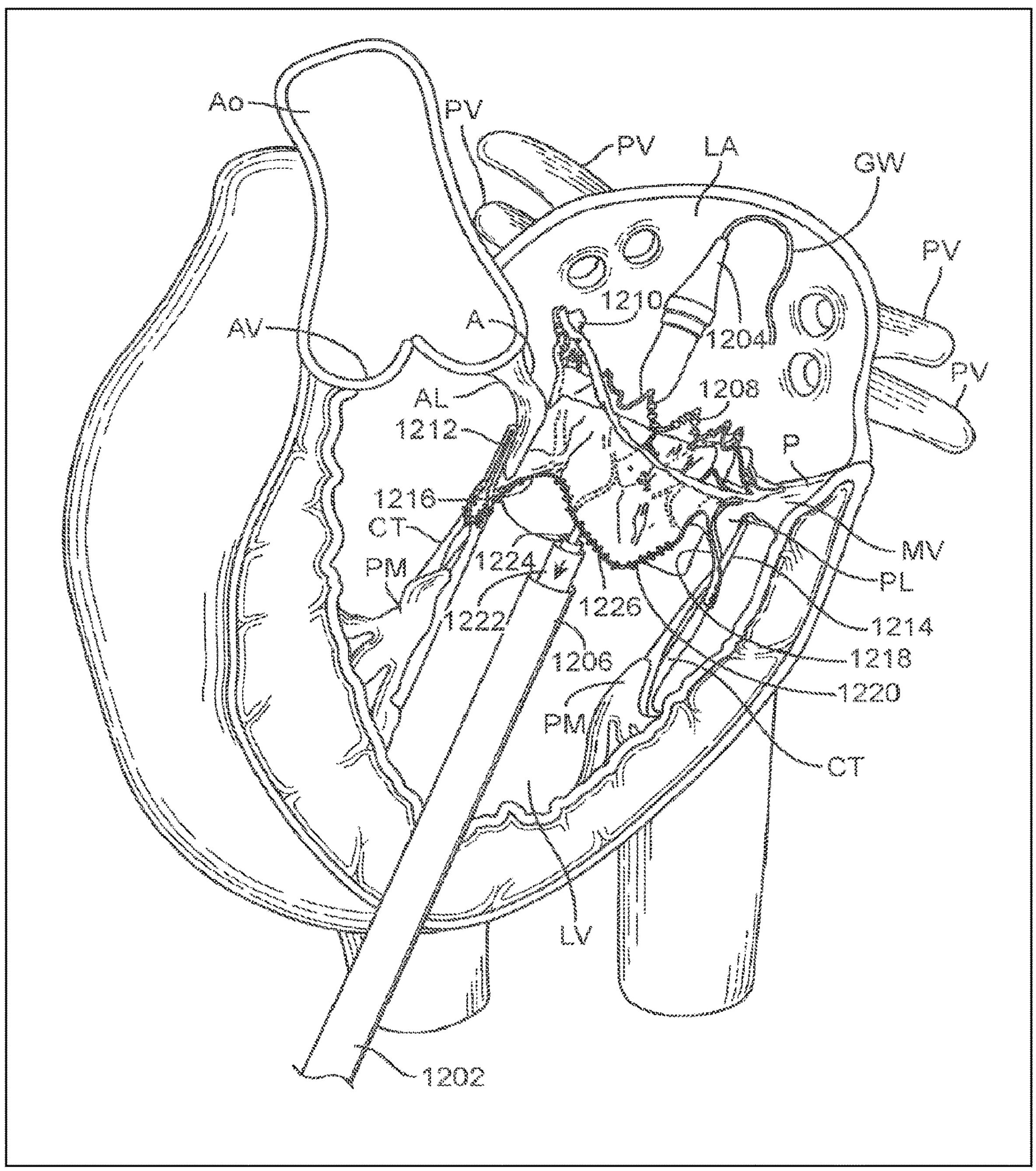
Figure 12J:
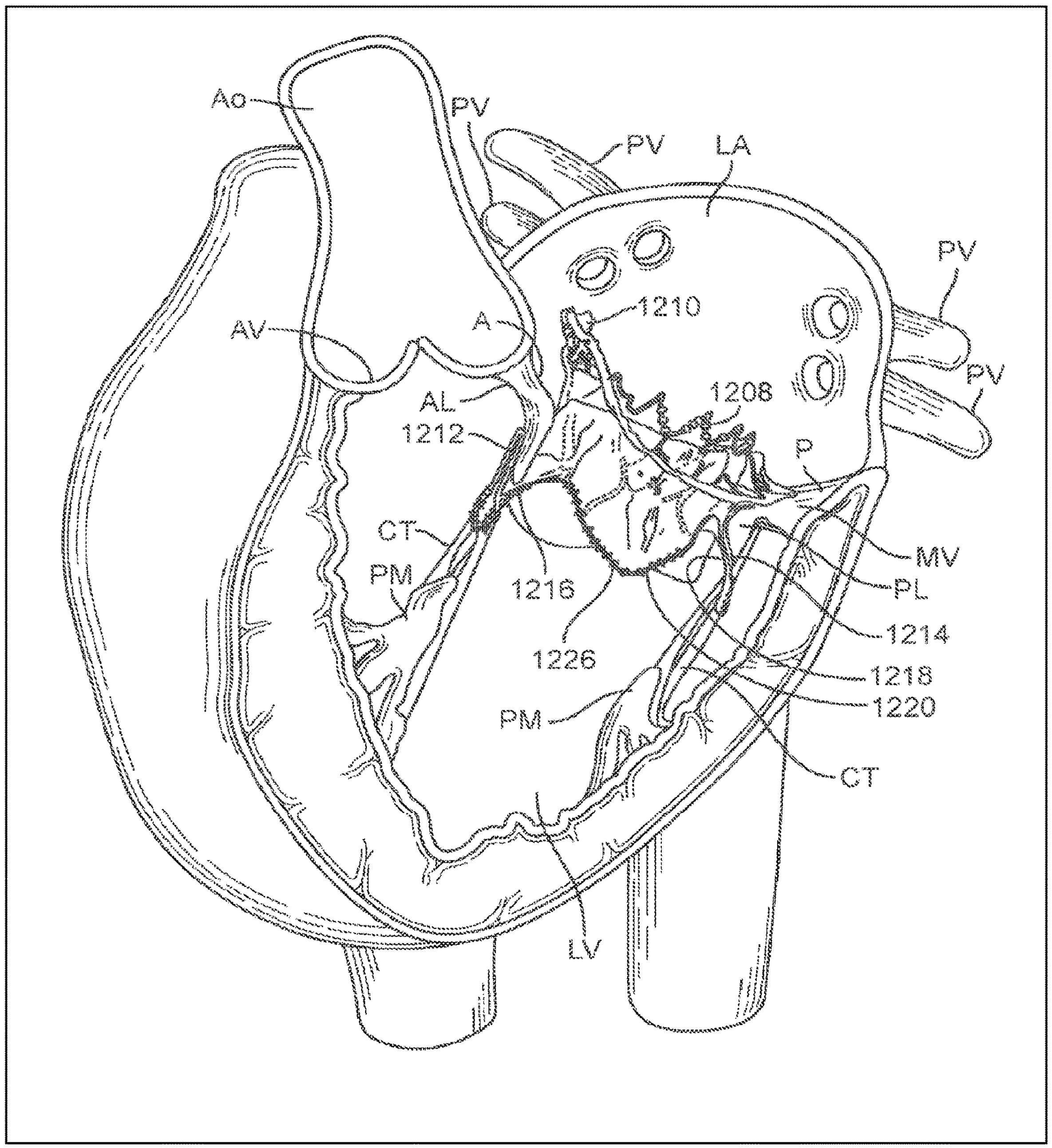

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
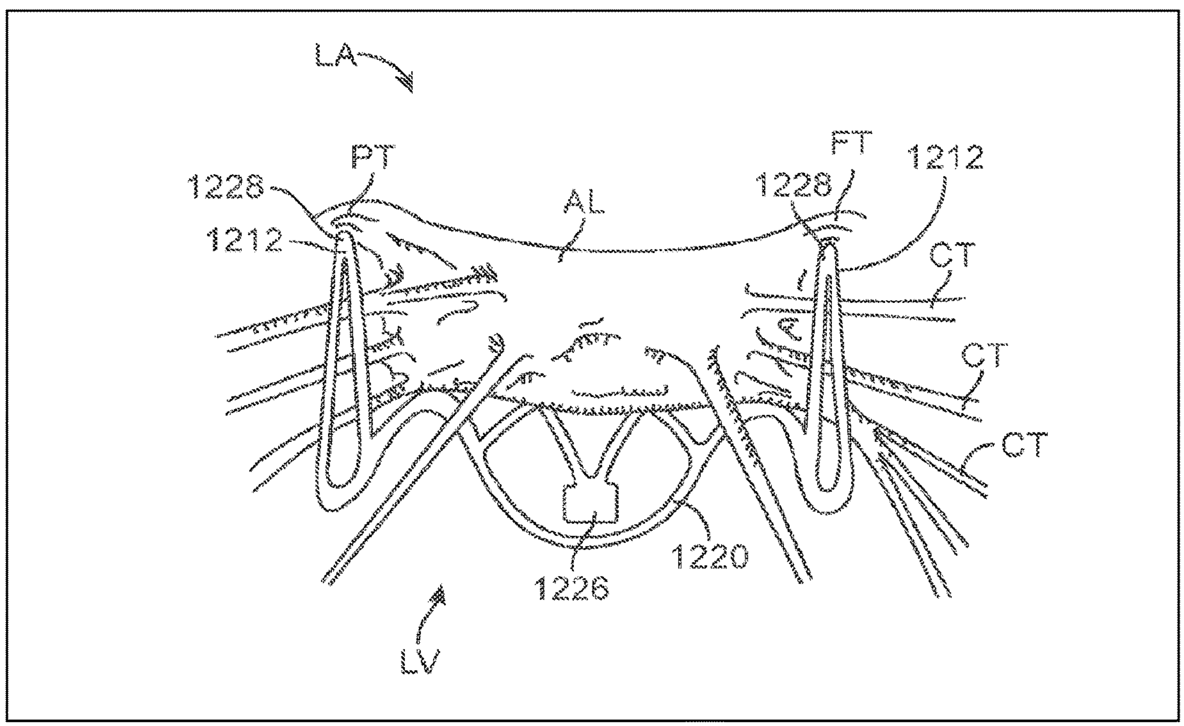
Figure 12L:
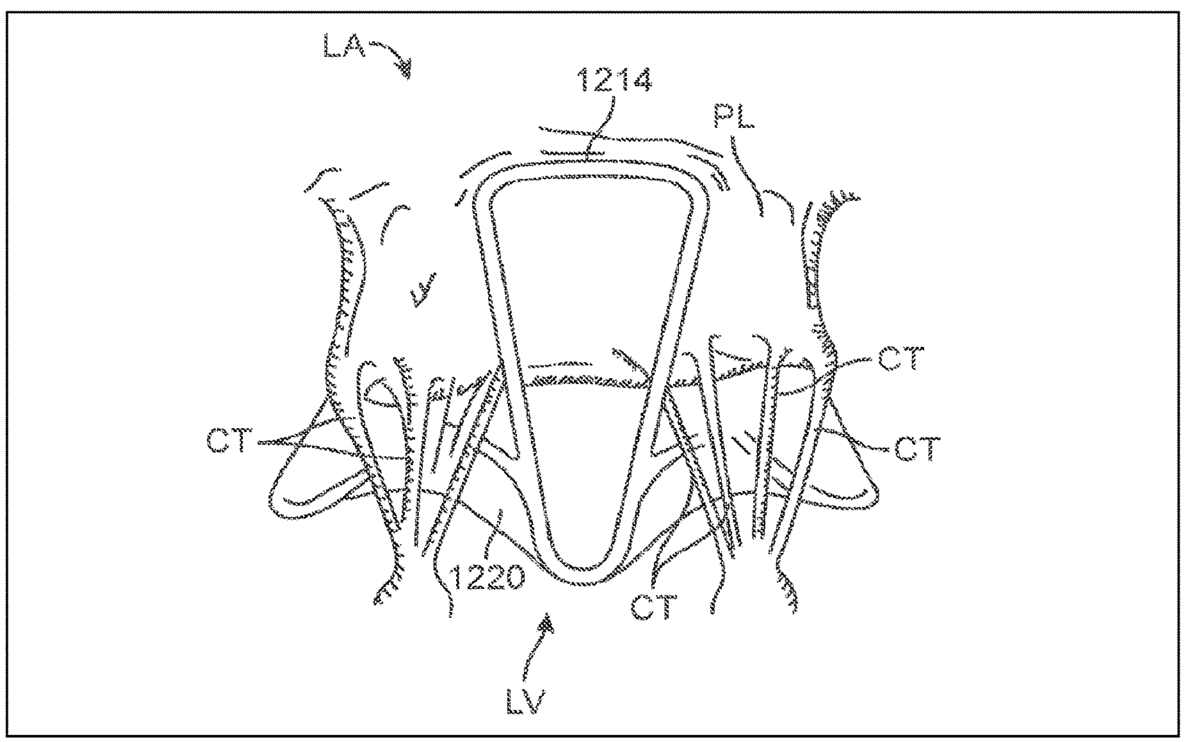

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. In other words, the anterior tabs 1212 advance under (toward the ventricle) and behind the anterior leaflet AL and adjacent chordae tendineae, before the ventricular skirt 1220 expands and pushes out to capture the anterior leaflet AL and adjacent chordae tendinae between the ventricular skirt 1220 and the anterior tabs 1212. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is similarly captured between an inner surface of the posterior tab and an outer surface of the ventricular skirt 1220. Additionally, adjacent chordae tendineae are also captured between the posterior tab and ventricular skirt. In other words, the posterior tab 1214 advance under (toward the ventricle) and behind the posterior leaflet PL and adjacent chordae tendineae, before the ventricular skirt 1220 expands and pushes out to capture the posterior leaflet PL and adjacent chordae tendinae between the ventricular skirt 1220 and the posterior tab 1214.

FIGS. 13A-13L illustrate another example of a delivery method. This example is similar to that previously described, with the major difference being the order in which the prosthetic cardiac valve self-expands into engagement with the mitral valve. Any delivery device or any prosthetic cardiac valve disclosed herein may be used, however in the aforementioned examples, FIG. 7 is used. Varying the order may allow better positioning of the implant, easier capturing of the valve leaflets, and better anchoring of the implant. This method also preferably uses a transapical route, although transseptal may also be used.

Figure 13A:
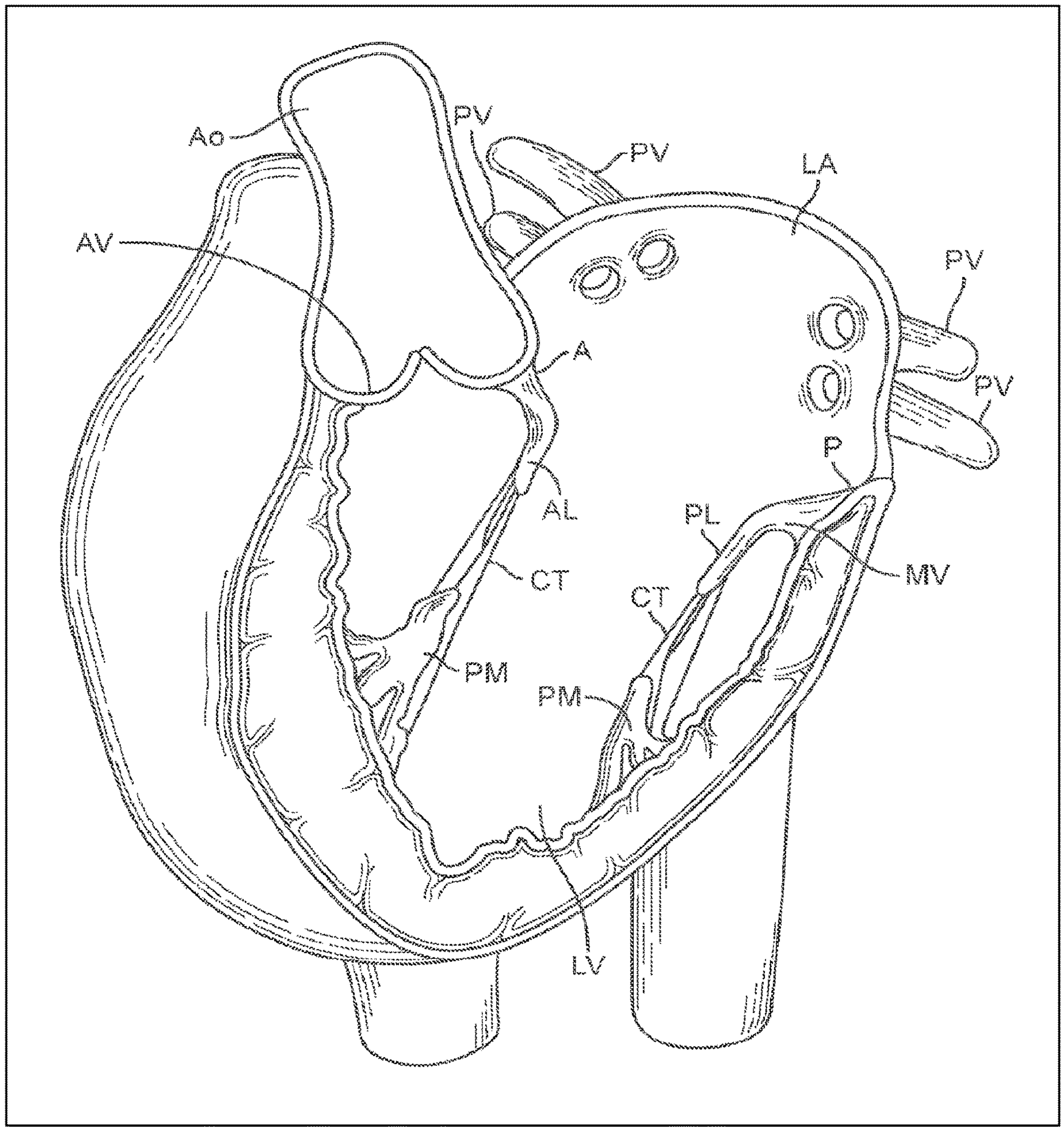
FIGS. 13A-13L illustrates another method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation.

Figure 13B:
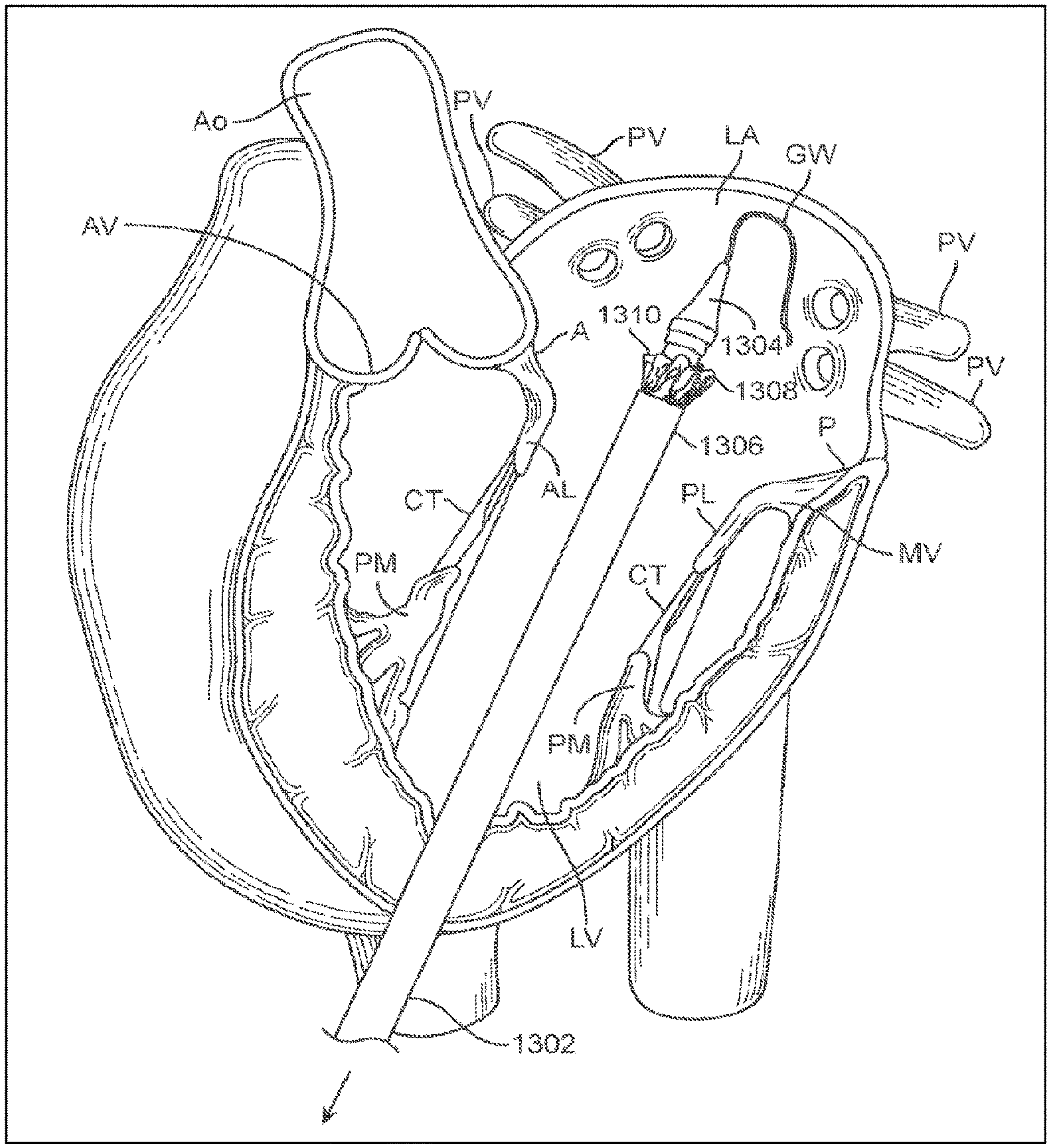
Figure 13C:
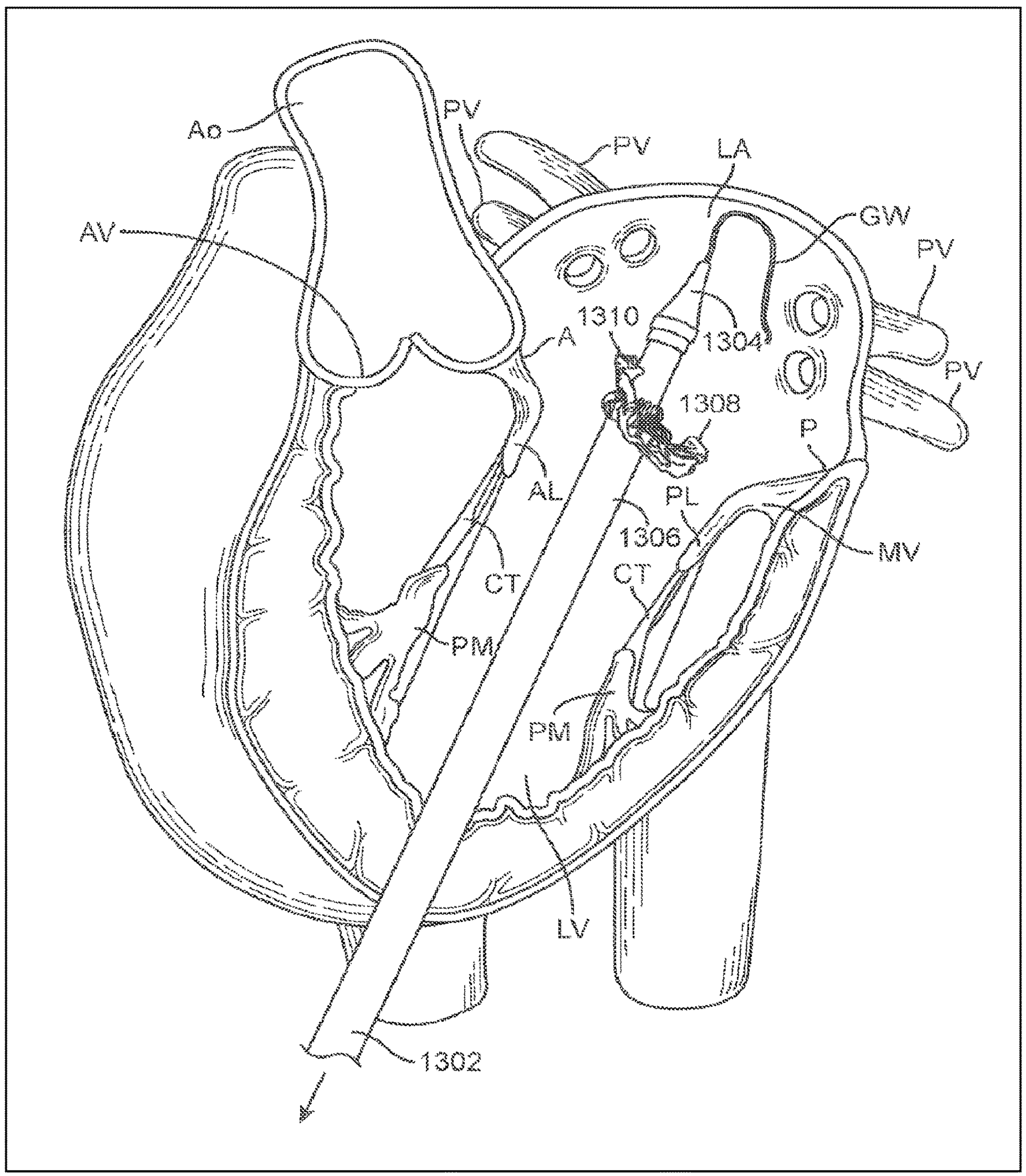
Figure 13D:
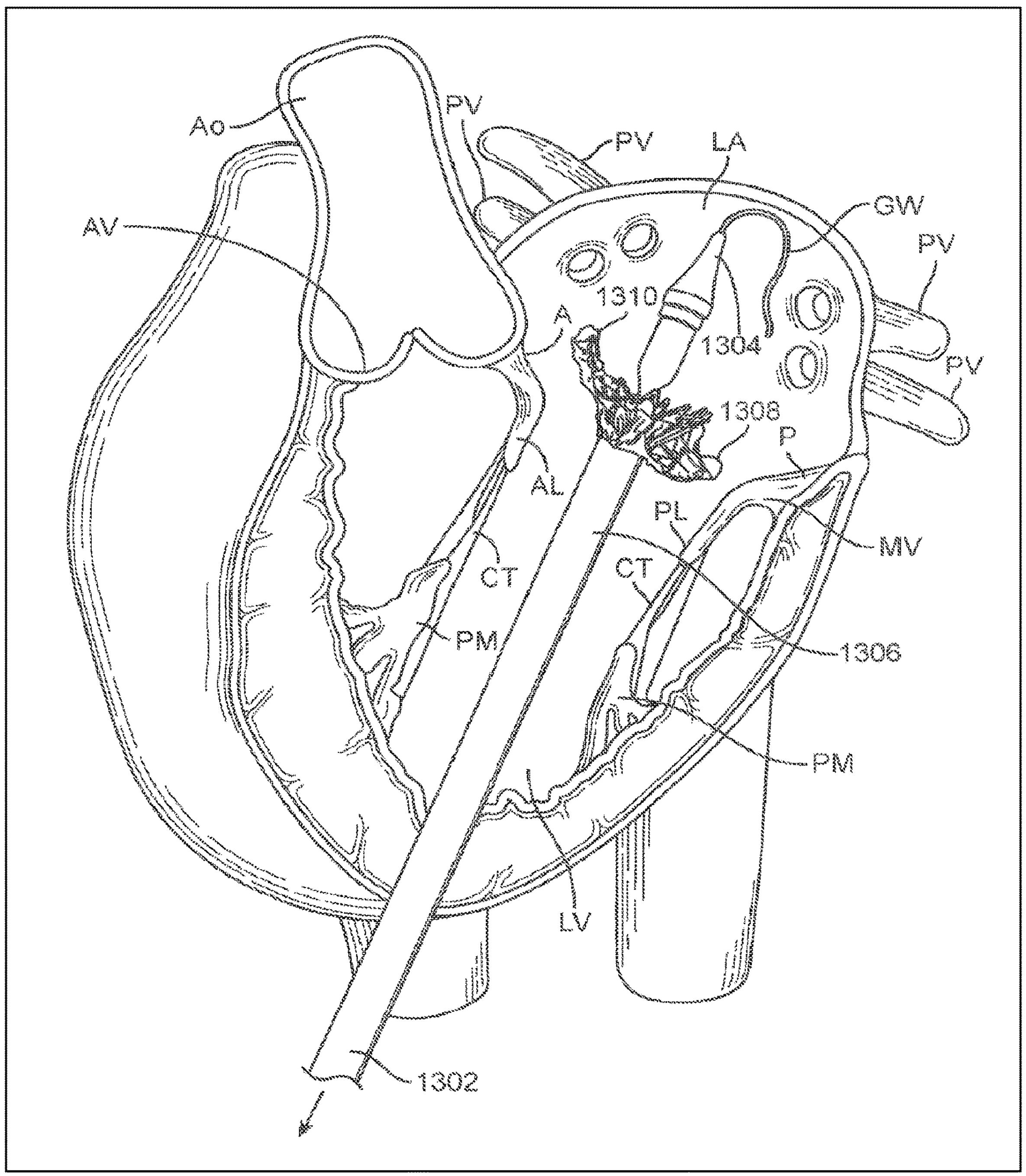

FIG. 13B illustrates transapical delivery of a delivery system 1302 through the apex of the heart into the left atrium LA via the left ventricle LV. The delivery system 1302 may be advanced over a guidewire GW into the left atrium, and a tissue penetrating tip 1304 helps the delivery system pass through the apex of the heart by dilating the tissue and showing a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. The atrial skirt has a flange that rests against a superior surface of the mitral valve and this anchors the prosthetic valve and prevents it from unwanted movement downstream into the left ventricle.

Figure 13E:
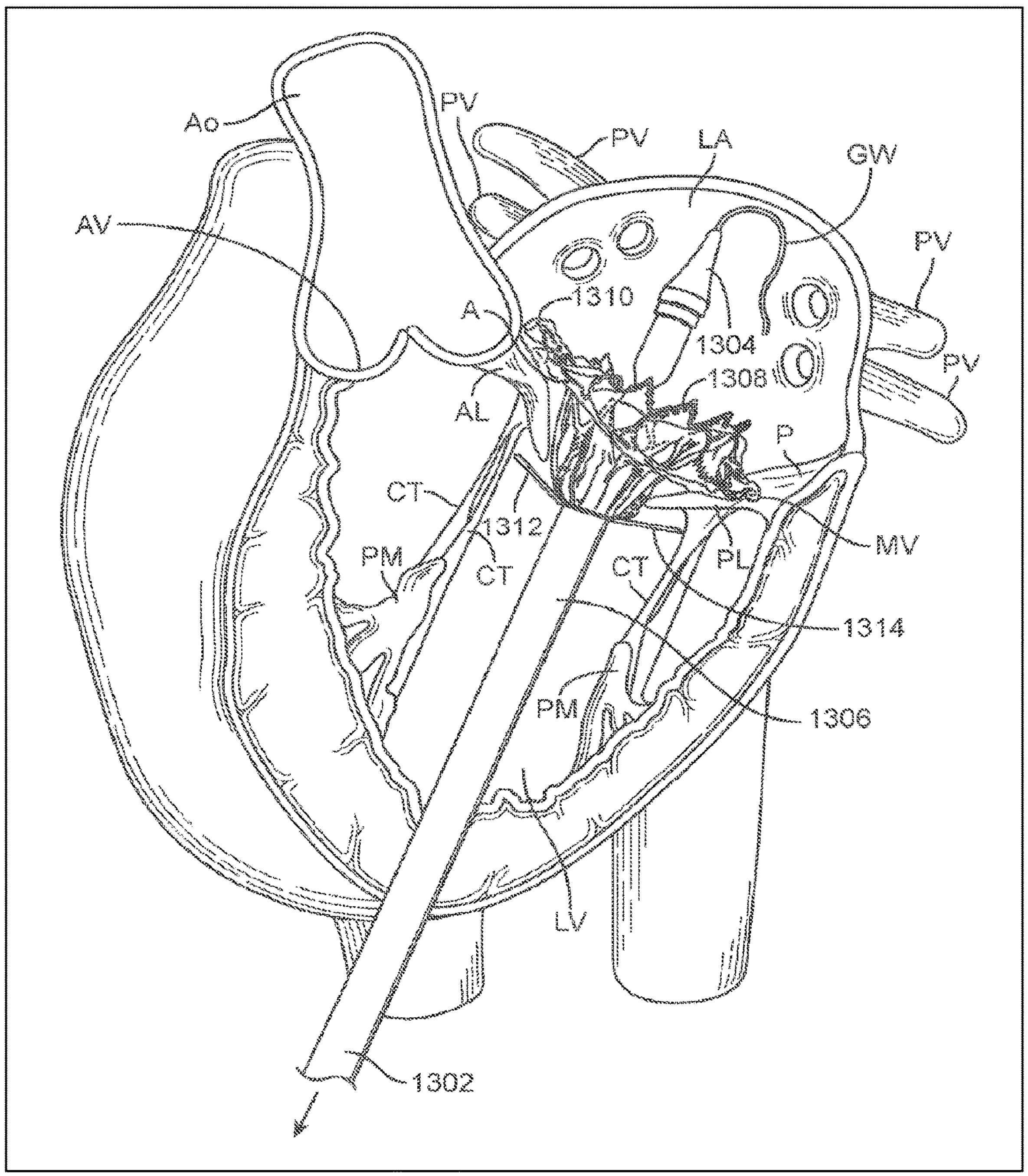
Figure 13F:
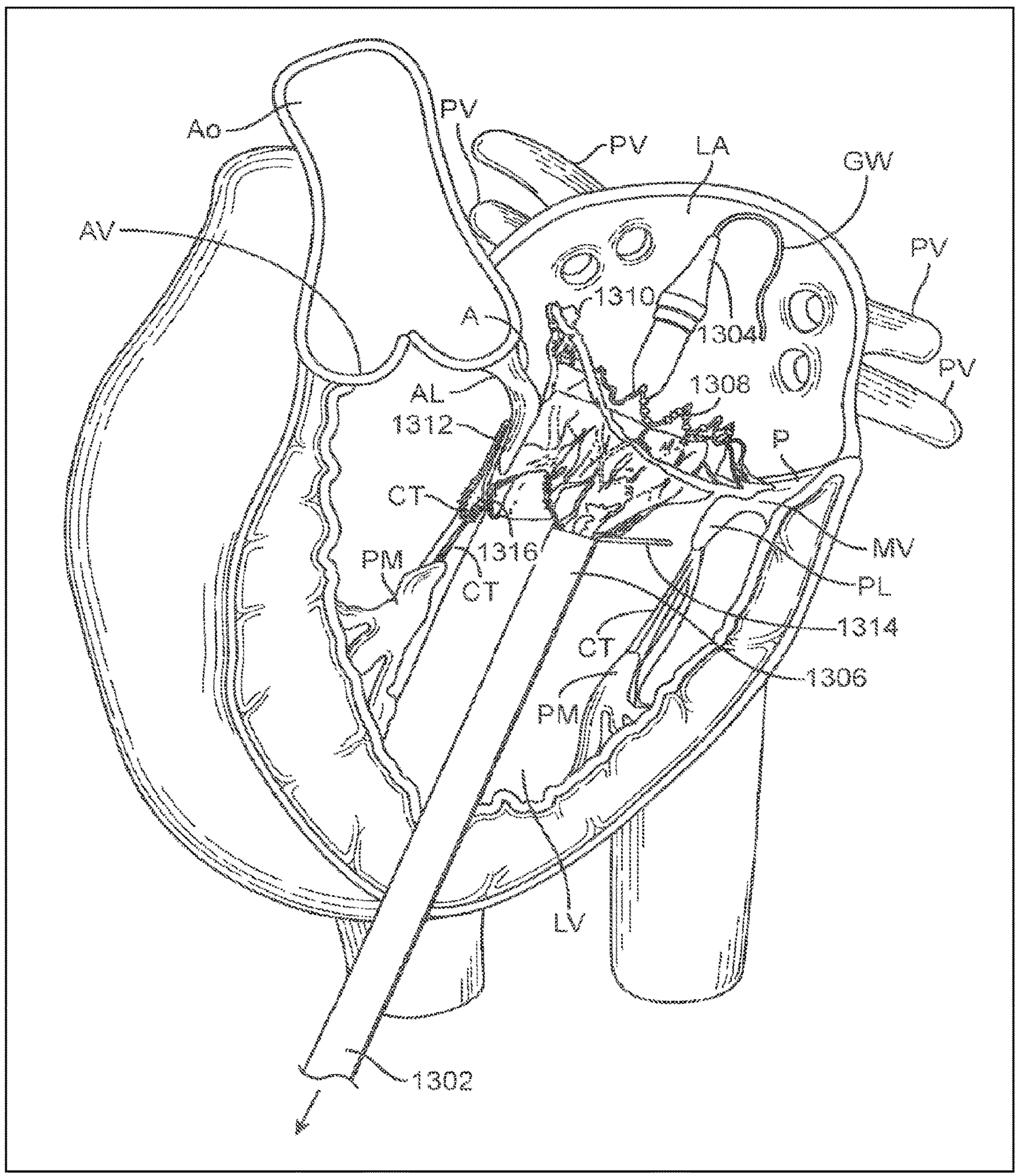

As the outer sheath 1306 continues to be proximally retracted, the annular region of the prosthetic cardiac valve self-expands within the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this example, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
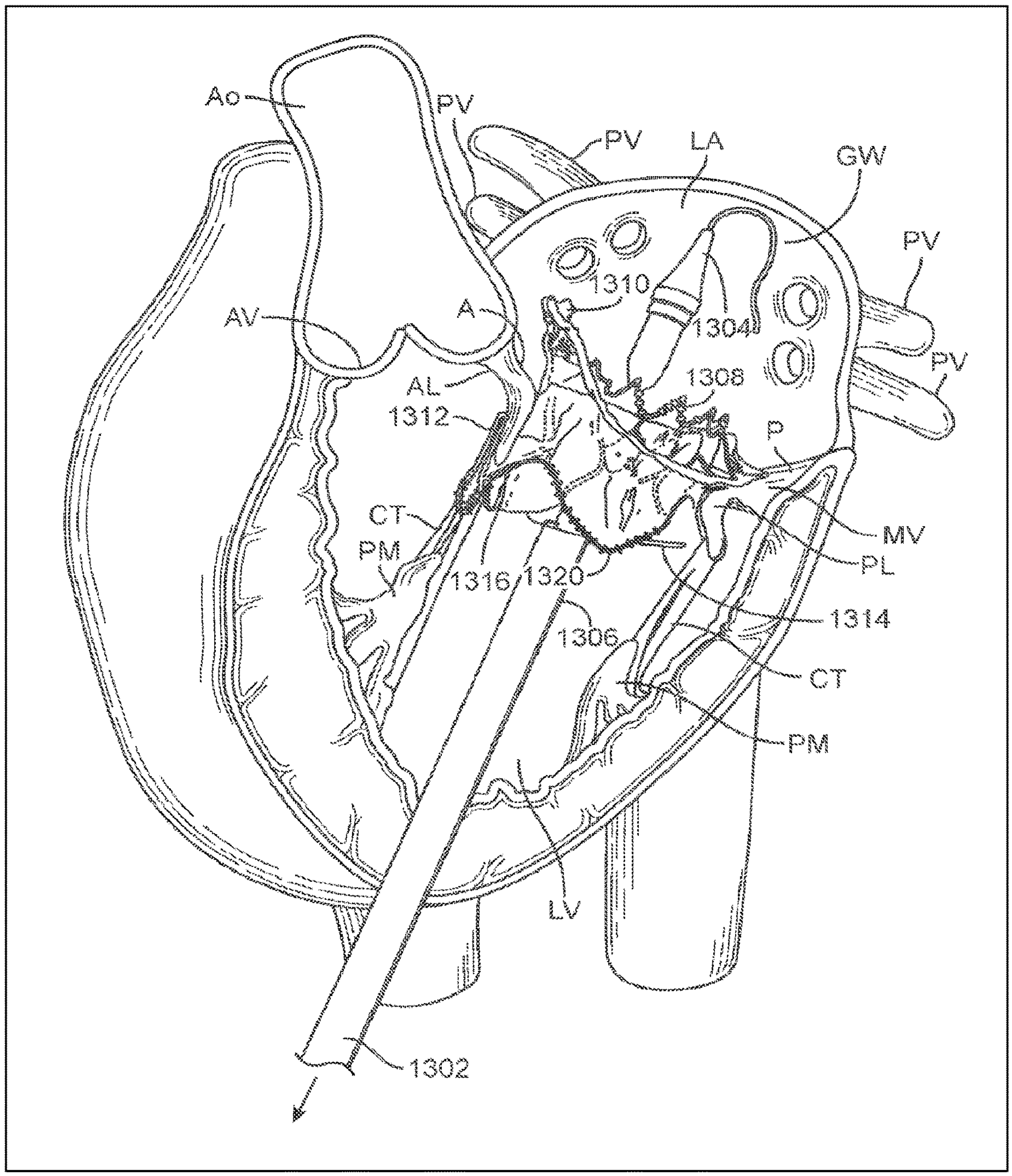
Figure 13H:
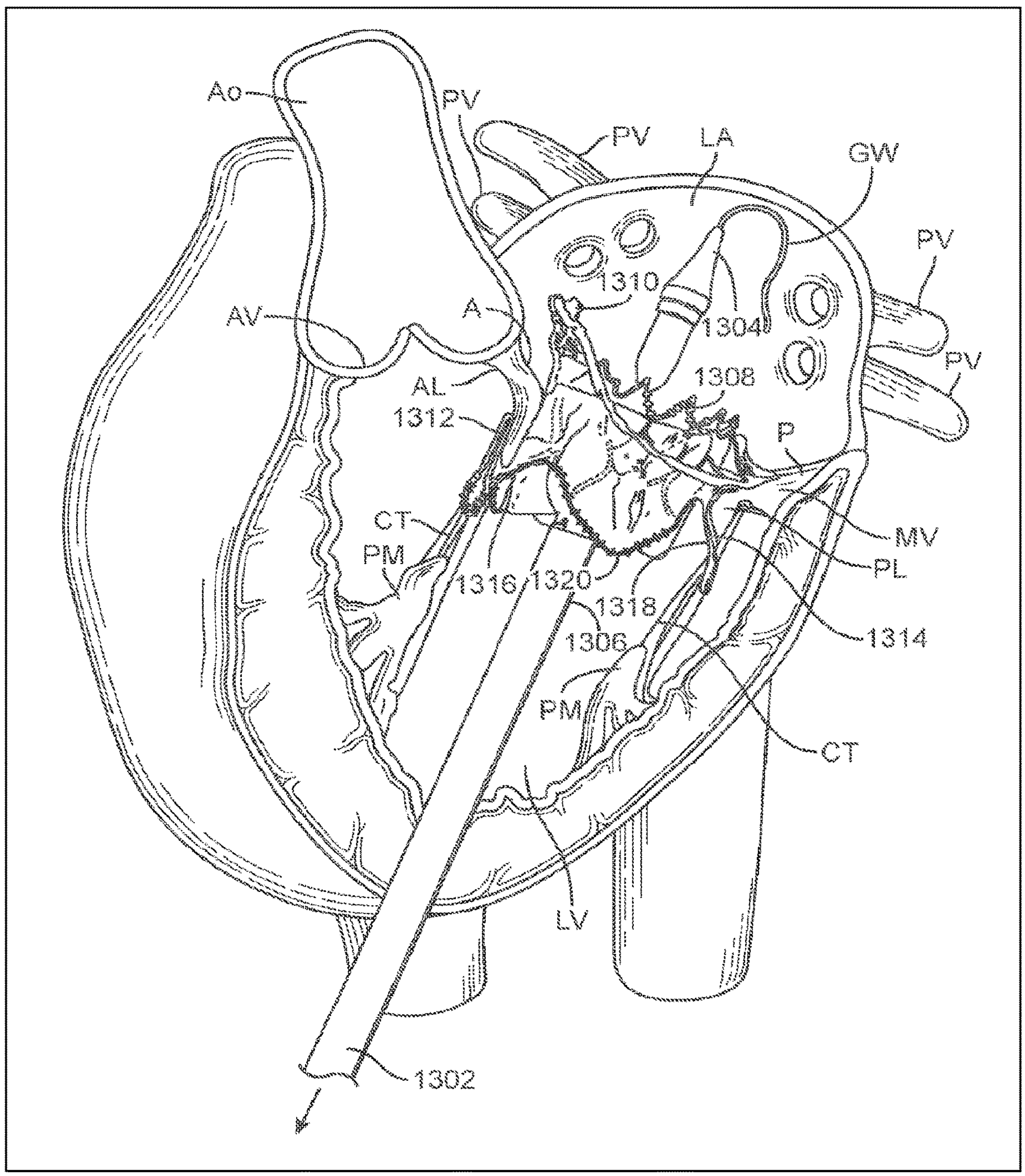

In FIG. 13G, further retraction of the outer sheath 1306 then releases the constraint from the ventricular skirt 1320 allowing the ventricular skirt to radially expand. This then further captures the anterior leaflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
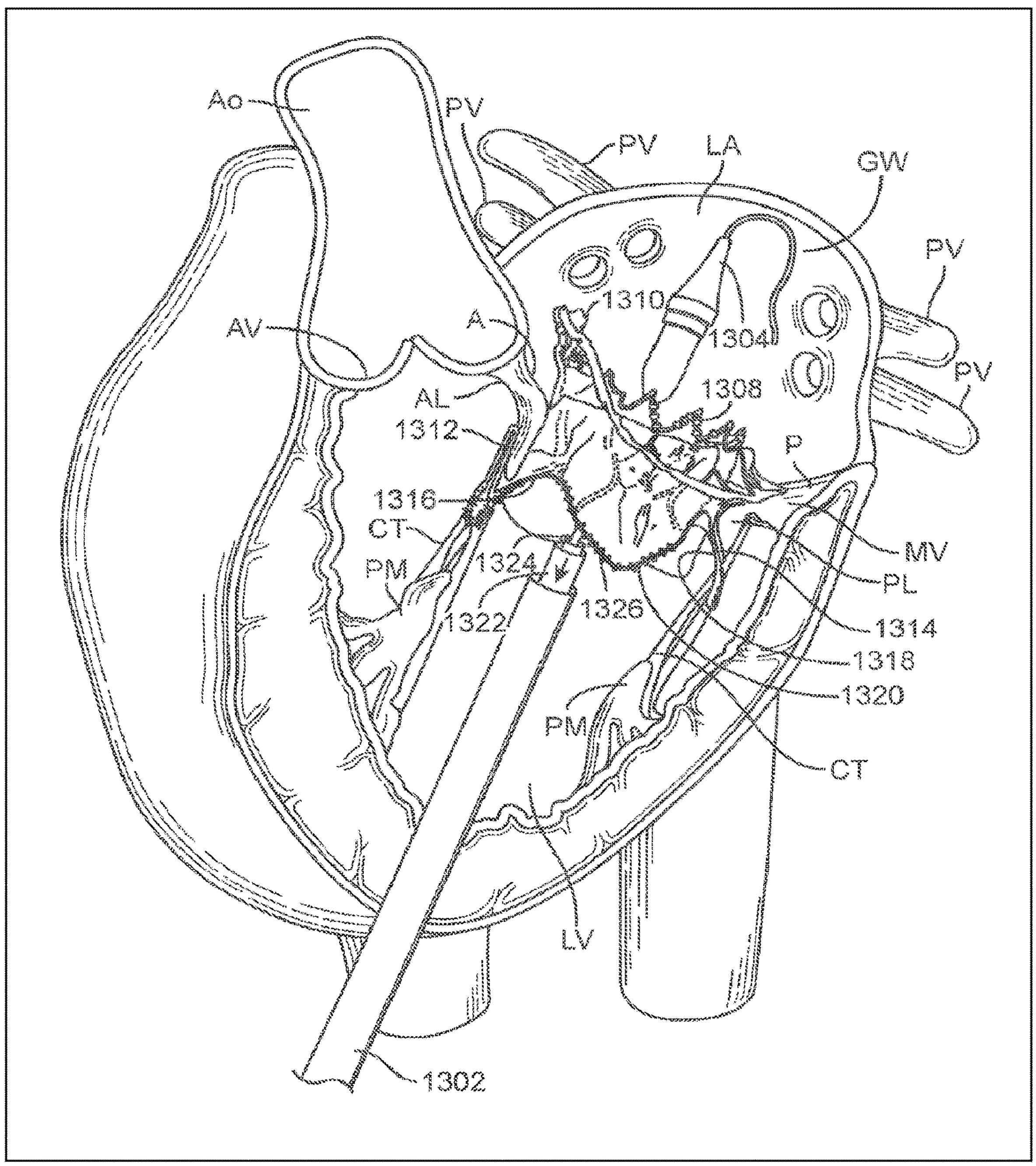
Figure 13J:
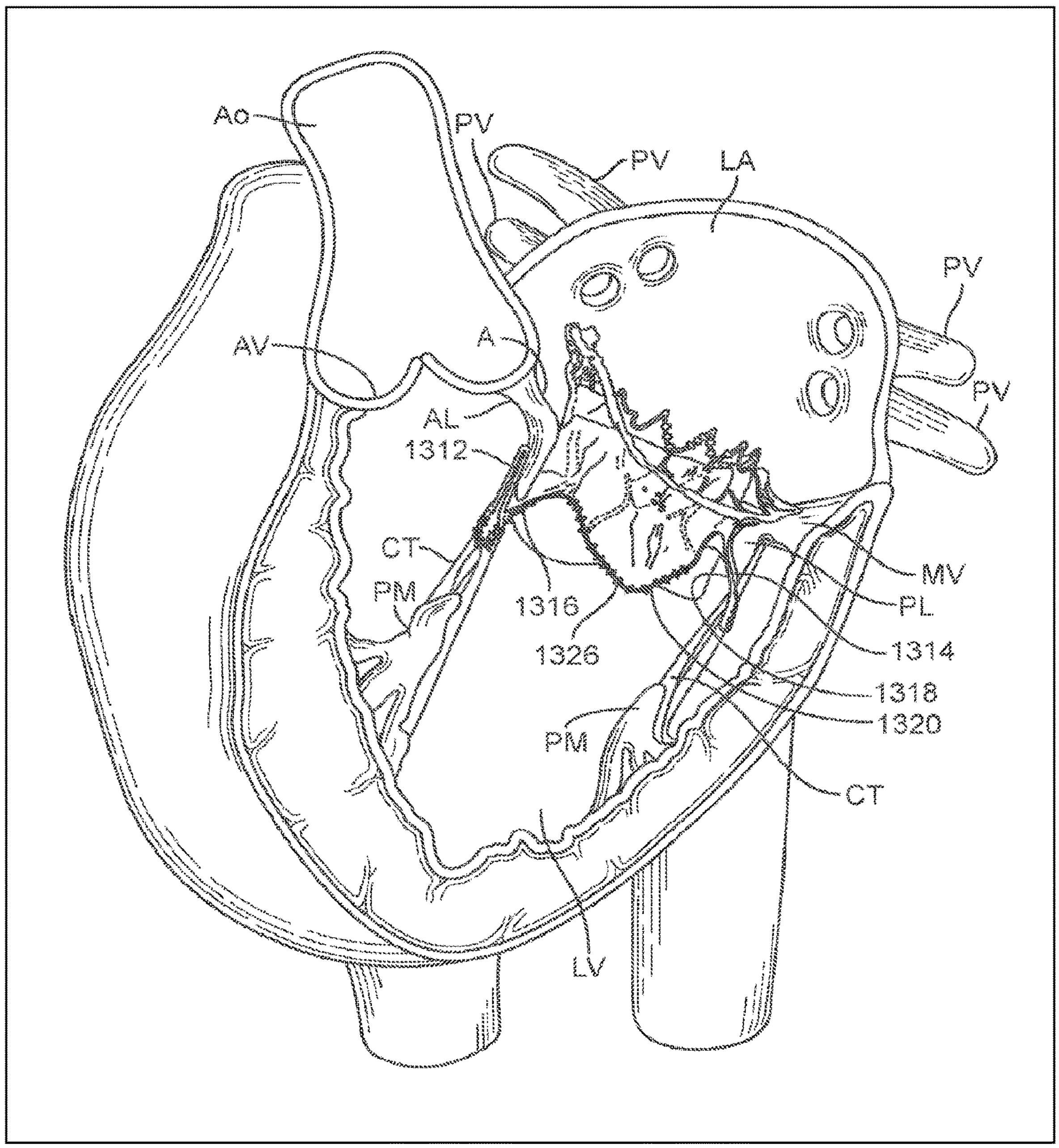

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
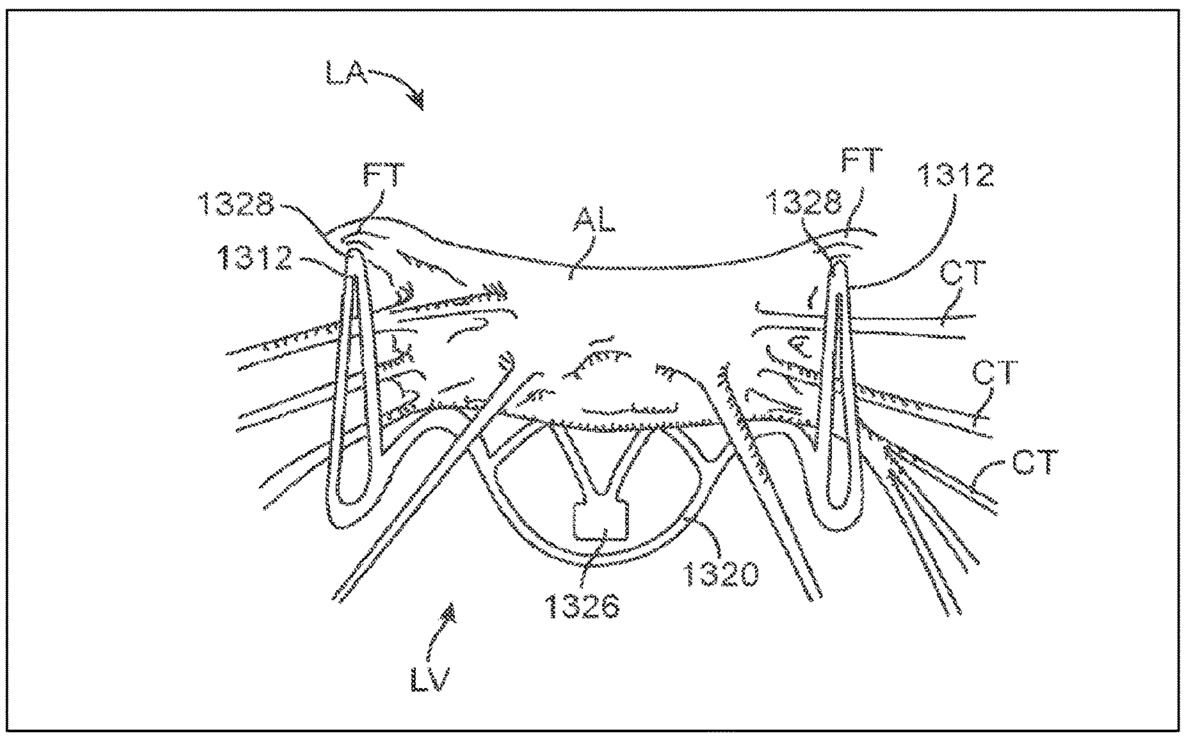
Figure 13L:
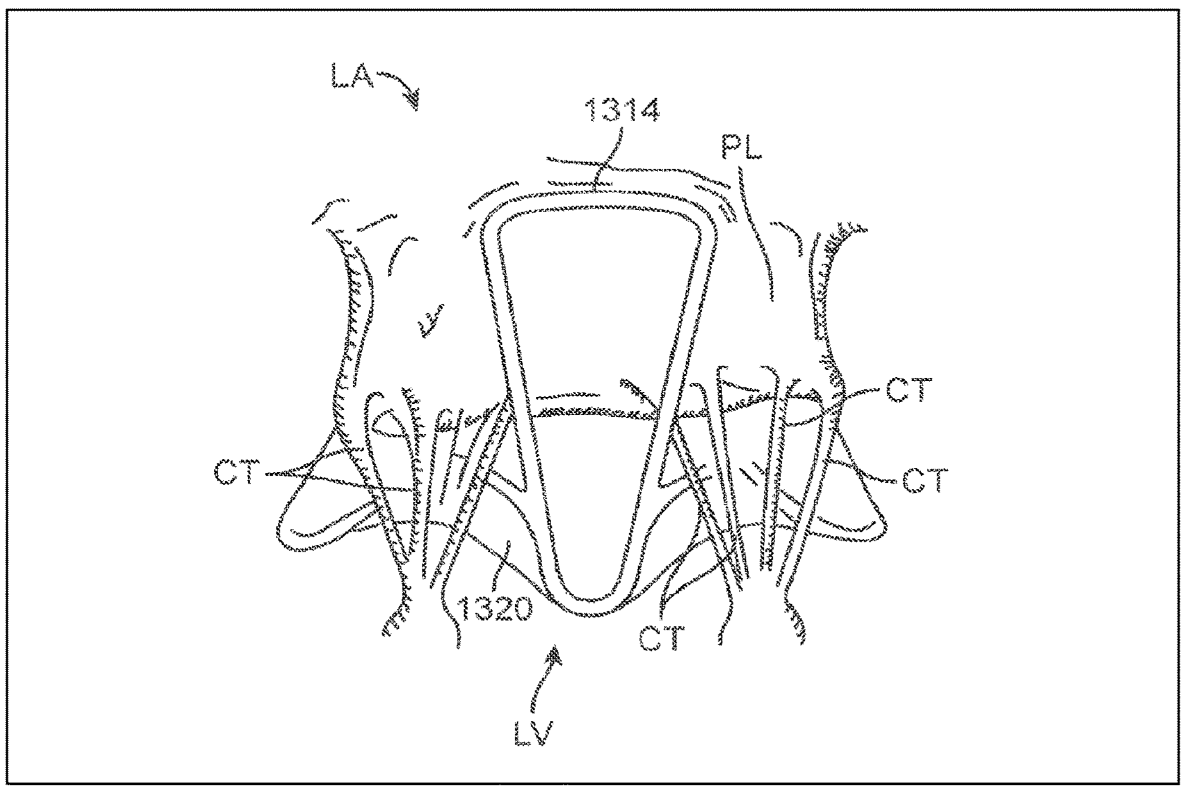

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve (similarly to anterior tabs 1212 described above). The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320 (similarly to posterior tab 1214 described above). Additionally, adjacent chordae tendineae are also captured between the posterior tab and ventricular skirt.

Tab Covering.

In the examples described above, the tabs (anterior trigonal tabs and posterior ventricular tab) are generally narrow and somewhat pointy. The feature previously described with respect to FIG. 8 includes a horizontal strut on the posterior tab that helps distribute force across a greater area and thereby reduces trauma to the tissue. FIGS. 14A-14D illustrate another example that is preferably used with the anterior trigonal tabs to help reduce trauma. It may also be used with the posterior tab if desired.

Figure 14A:
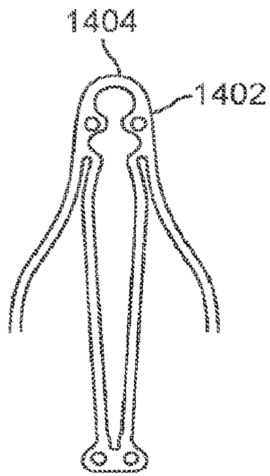
FIGS. 14A-14D illustrate a tab covering.
Figure 14B:
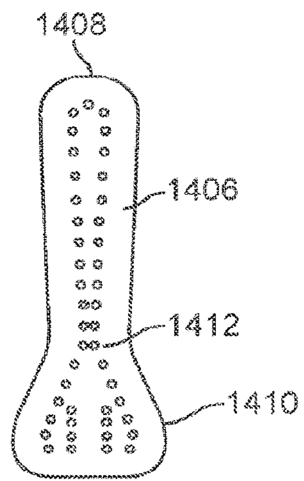
Figure 14C:
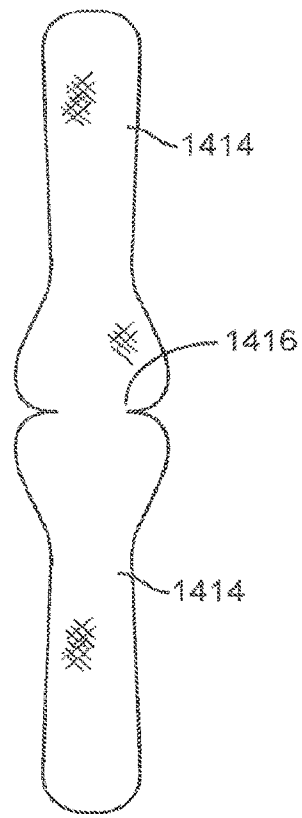
Figure 14D:
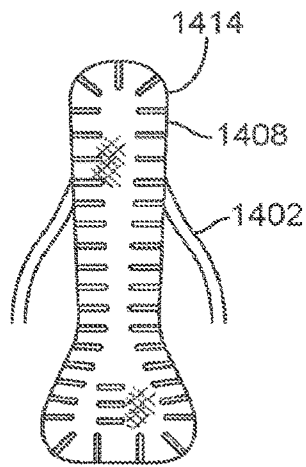

FIG. 14A illustrates an anterior trigonal tab 1402 having a tip 1404. This tip can be narrow and pointy and thereby induce tissue trauma when deployed into the tissue. Therefore, in some examples, it may be desirable to place a cover over the tip to help reduce tissue trauma. FIG. 14B illustrates a polymer tab 1406 that may be attached to the trigonal tab 1402. In other examples, the tab may be examples from other materials such as fabric, metals, or other materials known in the art. The polymer tab may be laser cut from a sheet of polymer and includes a long axial portion 1408 and an enlarged head region 1410. A plurality of suture holes 1412 may be pre-cut into the polymer tab 1406 and the holes are sized to receive suture material. Precut holes on the polymer tab may be aligned with pre-cut holes on the trigonal tab and then the polymer tab may be secured to the trigonal tab with sutures, adhesives, or other coupling techniques known in the art. A fabric cover 1414 having two symmetric halves separated by a hinged area 1416 is then wrapped around the polymer tab and attached to the polymer tab by sutures, thereby showing a shroud around the trigonal tab. The fabric may be Dacron, ePTFE, or any other biocompatible material known in the art. Thus, the cover increases the surface area of contact between the trigonal tabs and the tissue thereby reducing potential trauma and likelihood of piercing the heart wall. Additionally, the material may allow tissue ingrowth which further helps to anchor the prosthesis. Materials and dimensions are also selected in order to maintain the low profile of the device during delivery in the collapsed configuration.

Sequential Deployment.

As discussed above and herein, the deployment of the tabs, particularly the sequence of deployment (and thereby capture and/or engagement of the anterior leaflet AL, the posterior leaflet PL, and the adjacent chordae tendinae), may be controlled by controlling strut length and/or axial position of the anterior and/or posterior tabs. For instance, the axial position of the atrial end of the tabs may be varied to vary when the tabs begin deployment as the constraining sheath is retracted, and the axial position of the ventricular end of the tabs may be varied to vary when the tabs are fully deployed as the constraining sheath is retracted. Particular sequences of deployment may be more optimal to certain anatomies and may allow the prosthetic valve to be more accurately delivered and more securely anchored into position. For example, either the anterior tab(s) or the posterior tab(s) may be more easily visualized than the other in at least some cases, and the more easily visualized tab may be configured to deploy first as a guide to orient the frame during implantation. In at least some cases, the Inventors have found that the posterior tab is easier to visualize using ultrasound and/or fluoroscopy. The sequence of tab deployment may be customized to the individual patient and their anatomy in some cases and the customization may be based on pre-screen imaging data for the individual patient. The tabs that are projected to be more easily visualized, such as by using ultrasound and/or fluoroscopy, may be configured to deploy first. The initially deployed tabs can allow for intermediate movement of the imaging source, e.g., the C-arm controlling the ultrasound or X-ray device for fluoroscopy, so as to provide verification of the initial tab placements. If needed, the prosthetic valve may be repositioned and/or reoriented with the initial tab(s) partially and/or fully deployed (and the remaining tab(s) yet to be partially and/or fully deployed) based on the imaging or visualization. To further improve the visibility of the tabs, the length and/or curvature of one or more of the tabs may be customized for the individual patient and their anatomy. The length and/or curvature of the one or more tabs may be customized to provide an optimum fit for the individual patient's anatomy, such as the deployment area behind the valve leaflet(s) and/or the chordae tendinae.

In some examples, the first and second anterior tabs may be deployed concurrently. FIGS. 15A-15E schematically illustrate the deployment of a prosthetic cardiac valve 1500*a* whereby its first anterior tab A1 and its second anterior tab A2 are concurrently deployed. FIG. 15A shows a constraining sheath 1550 fully constraining the prosthetic cardiac valve 1500*a*. The prosthetic cardiac valve 1500*a* may be deployed as the constraining sheath 1550 is retracted from the atrial (ATR) side of the prosthetic cardiac valve 1500*a* to the ventricular (VEN) side. As shown in FIG. 15B, the retraction of the constraining sheath 1550 may first allow the atrial skirt 1506 of the prosthetic cardiac valve 1500 to begin to self-expand radially outward. As shown in FIG. 15C, the constraining sheath 1550 may be retracted further to concurrently release the first anterior tab A1 and the second anterior tab A2 from constraint, exposing the tabs. As shown in FIG. 15D, further retraction of the constraining sheath 1500*a* allows the first anterior tab A1 and the second anterior tab A2 to partially spring radially outward to be in orientations that are transverse to the longitudinal axes of the constraining sheath 1550 and prosthetic cardiac valve 1500*a* as described above. The first and second anterior tabs A1, A2 may have the same length and/or may be positioned on the prosthetic cardiac valve so that their atrial ends are positioned in the same axial position; hence, the retraction of the constraining sheath 1550 may expose the anterior tabs A1, A2 and/or allow the anterior tabs A1, A2 to partially deploy concurrently. As shown in FIG. 15E, the constraining sheath 1550 may be fully retracted to fully release the prosthetic cardiac valve 1500*a*, allowing the anterior tabs A1, A2 to fully deploy to capture the adjacent chordae tendineae and also to allow the ventricular skirt 1516 to self-expand radially outward. The posterior tab PTB of the prosthetic cardiac valve 1500, while not shown in FIGS. 15A-15E, may be configured to deploy before, concurrently with, or after the anterior tabs A1, A2.

Figure 15I:
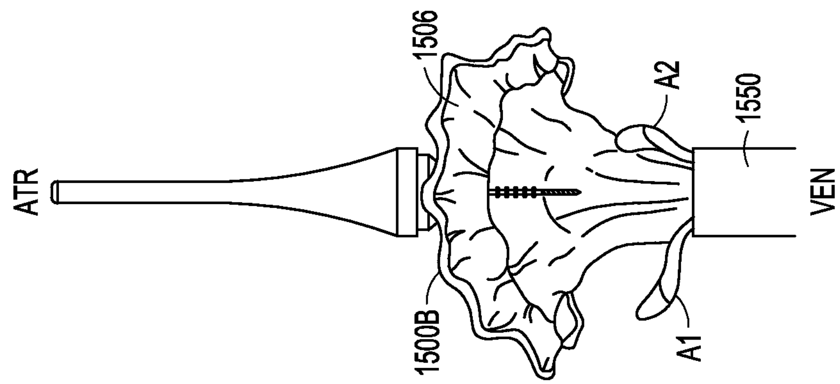
FIGS. 15F-15L schematically illustrate a method of deploying a prosthetic cardiac valve whereby the first anterior tab is deployed before the second anterior tab, according to many examples.
Figure 15H:
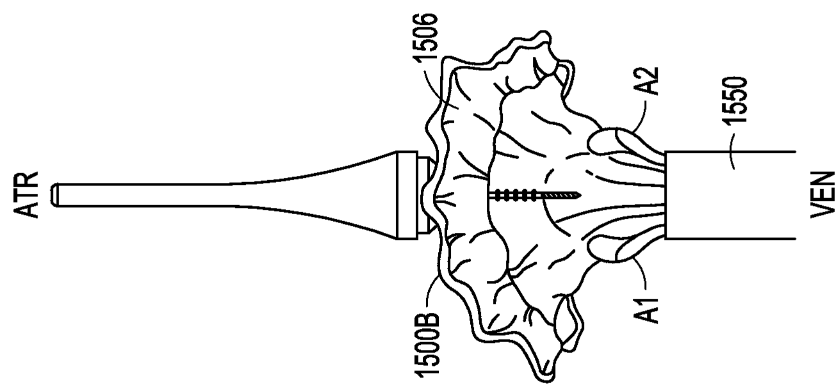
Figure 15G:
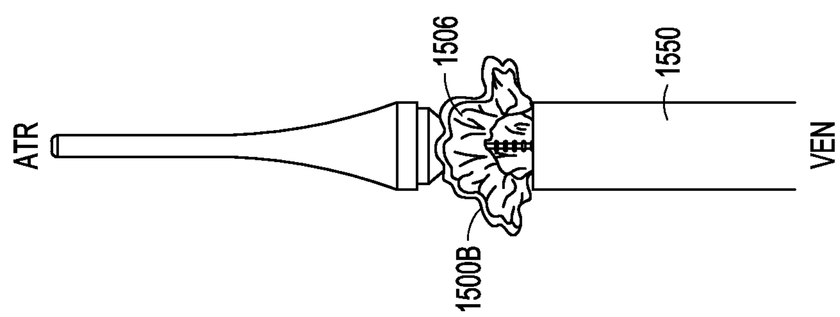
Figure 15F:
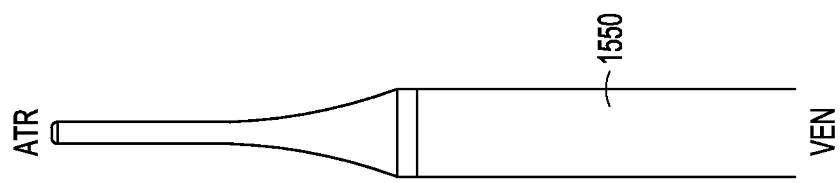
Figure 15L:
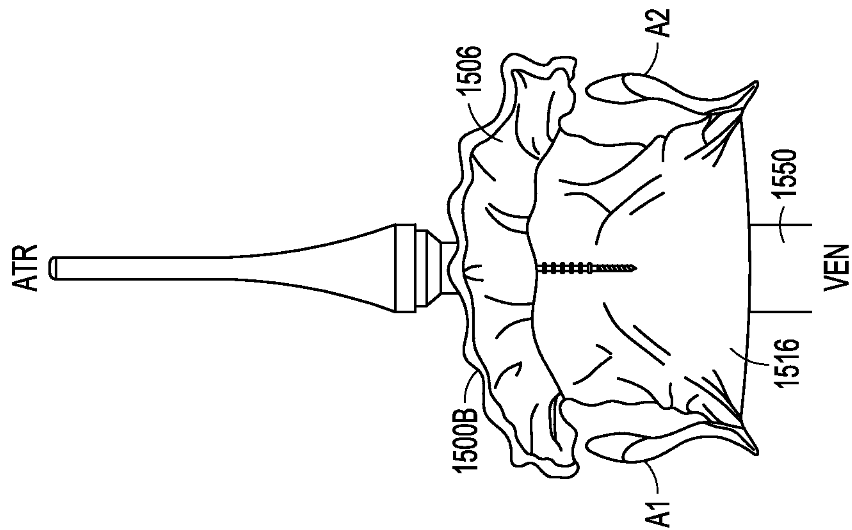
Figure 15K:
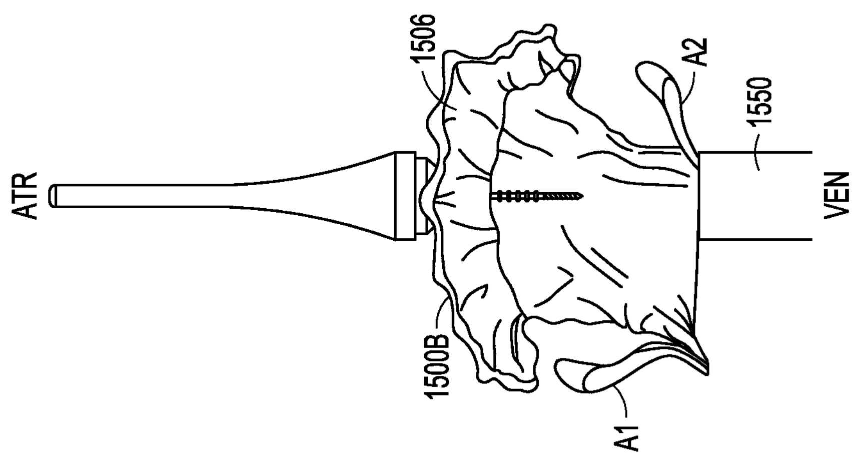
Figure 15J:
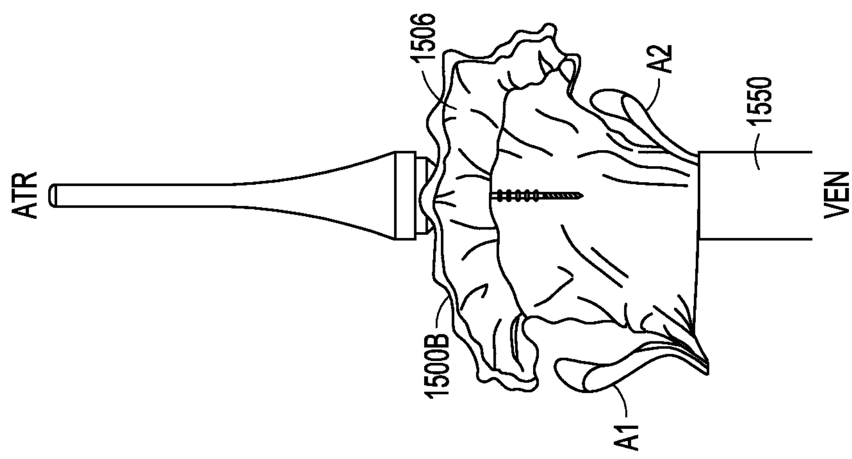

In some examples, the first and second anterior tabs may be deployed sequentially. FIGS. 15F-15L schematically illustrate the deployment of a prosthetic cardiac valve 1500*b* whereby its first anterior tab A1 and its second anterior tab A2 are sequentially deployed. FIG. 15F shows a constraining sheath 1550 fully constraining the prosthetic cardiac valve 1500*b*. The prosthetic cardiac valve 1500*b* may be deployed as the constraining sheath 1550 is retracted from the atrial (ATR) side of the prosthetic cardiac valve 1500 to the ventricular (VEN) side. As shown in FIG. 15G, the retraction of the constraining sheath 1550 may first allow the atrial skirt 1506 of the prosthetic cardiac valve 1500*b* to begin to self-expand radially outward. As shown in FIG. 15H, the constraining sheath 1550 may be retracted further to concurrently release the first anterior tab A1 and the second anterior tab A2 from constraint, exposing the tabs. As shown in FIG. 15I, further retraction of the constraining sheath 1550 allows the first anterior tab A1 to partially spring radially outward to be in orientations that are transverse to the longitudinal axes of the constraining sheath 1550 and prosthetic cardiac valve 1500*b* as described above, while the second anterior tab A2 remains in an undeployed configuration. As shown in FIG. 15J, even further retraction of the constraining sheath 1550 fully frees the first anterior tab A1 from constraint, allowing the first anterior tab A1 to fully deploy to capture adjacent chordae tendineae. As shown in FIG. 15K, subsequent retraction of the constraining sheath 1550 allows the second anterior tab A1 to partially spring radially outward to be in orientations that are transverse to the longitudinal axes of the constraining sheath 1550 and prosthetic cardiac valve 1500*b* as described above. As shown in FIG. 15L, even further retraction of the constraining sheath 1550 fully frees the second anterior tab A2 from constraint, allowing the second anterior tab A2 to fully deploy to capture adjacent chordae tendineae as well the ventricular skirt 1516 to self-expand radially outward. The posterior tab PTB of the prosthetic cardiac valve 1500*b*, while not shown in FIGS. 15F-15L, may be configured to deploy before one or both of the anterior tabs A1, A2, concurrently with one of the anterior tabs A1, A2, or after one or both of the anterior tabs A1, A2.

While FIGS. 15A-15E and FIGS. 15F-15L show particular sequences of fully deploying the first and second anterior tabs A1, A2 and the posterior tab PTB, the first and second tabs A1, A2 and the posterior tab PTB may be configured to fully deploy in any order.

Figure 16A:
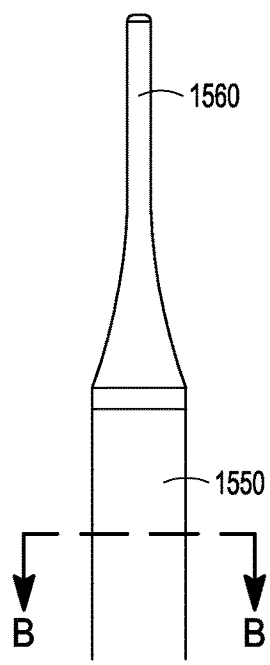
FIG. 16A shows a prosthetic cardiac valve held within a constraining sheath, according to many examples.
Figure 16B:
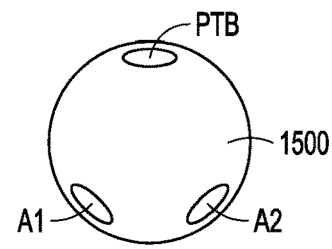
FIG. 16B schematically illustrates a cross-section of the prosthetic cardiac valve of FIG. 16A taken along line B-B of FIG. 16B.

FIG. 16A shows the prosthetic cardiac valve 1500 held within the constraining sheath 1550 while FIG. 16B schematically illustrates a cross-section of the prosthetic cardiac calve 1500 taken along line B-B of FIG. 16B and showing the relative positions of the first and second tabs A1, A2 and the posterior tab PTB. For the ease of illustration in FIGS. 17A-17M, the first and second anterior tabs A1, A2 (particularly their ventricular ends), the posterior tab PTB (particularly its ventricular end), and the edges V1, V2, and V3 of the ventricular skirt are shown in a rolled out configuration relative to a retracting constraining sheath 1550 to show various orders of full deployment of the first and second anterior tabs A1, A2 and the posterior tab PTB.

In some examples, the lengths of the tabs and/or the axial positions of the free ends 1701, 1702, 1703 of the tabs may be varied such that two or more of the two anterior tabs A1, A2 and the posterior tab PTB are fully deployed concurrently.

Figure 17A:
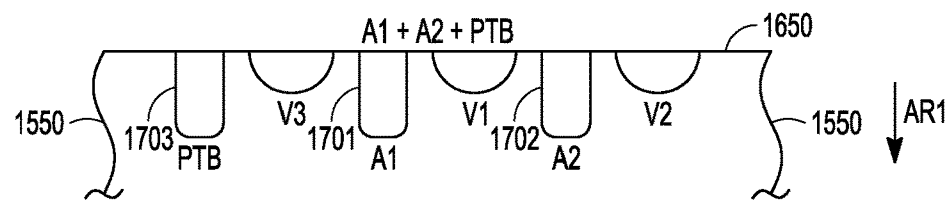
FIGS. 17A-17M schematically illustrate variations of different sequences for fully deploying a first anterior tab, a second anterior tab, and a posterior tab of a prosthetic cardiac valve, according to many examples.

As shown in FIG. 17A, a distal edge 1650 of the constraining sheath 1550 is arranged to retract proximally in the direction of arrow AR1 parallel to the longitudinal axis of the valve during tab deployment. In FIG. 17A, the first and second anterior tabs A1, A2 and the posterior tab PTB may all have the same length and/or have their free ends 1701, 1702, 1703 in the same axial positions. Therefore, the three tabs A1, A2, PTB are be fully deployed concurrently with one another as the distal edge 1650 of the constraining sheath 1550 retracts proximally in the direction of arrow A1 parallel to the longitudinal axis of the valve. The edges V1, V2, V3 of the ventricular skirt are closer to the annular region than the free ends 1701, 1702 1703 of the three tabs A1, A2, PTB such that, as the sheath 1550 is retracted, the ventricular skirt is configured to deploy before the tabs A1, A2, PTB finish expanding.

Figure 17B:
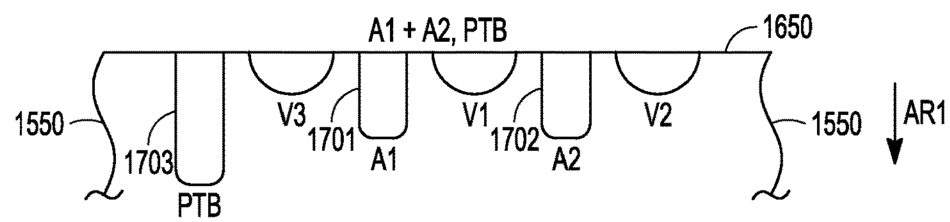

As shown in FIG. 17B, the distal edge 1650 of the constraining sheath 1550 is arranged to retract proximally in the direction of arrow AR1 parallel to the longitudinal axis of the valve during tab deployment. In FIG. 17B, the first and second anterior tabs A1, A2 may have the same length as each other, and the posterior tab PTB may have a greater length than the first and second anterior tabs A1, A2, and/or the free end 1703 of the posterior tab PTB may be further from the annular region than the free ends 1701, 1702 of the first and second anterior tabs A1, A2. Therefore, as the distal edge 1650 of the constraining sheath 1550 retracts proximally in the direction of arrow AR1 parallel to the longitudinal axis of the valve, the first and second anterior tabs A1, A2 are concurrently fully deployed before the posterior tab PTB is fully deployed. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

Figure 17C:
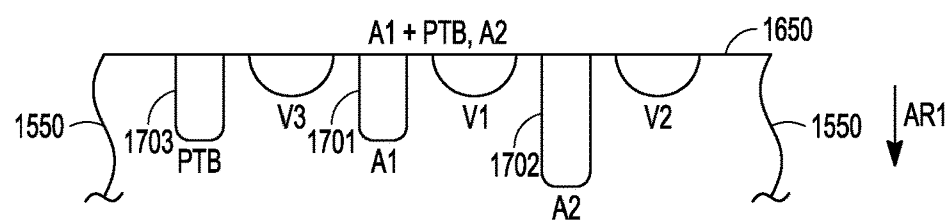
Figure 17D:
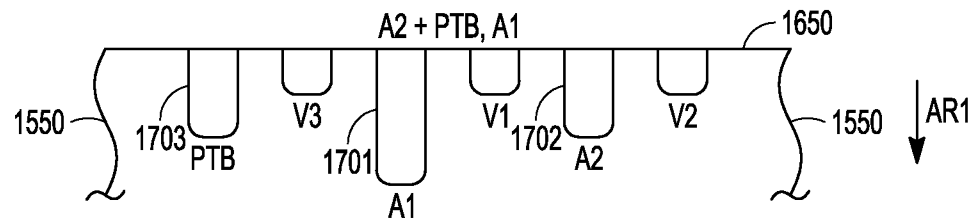
Figure 17E:
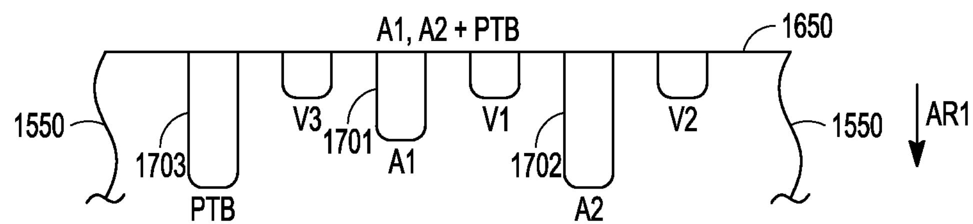
Figure 17F:
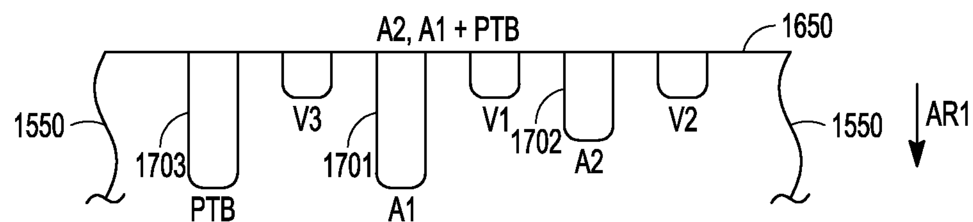
Figure 17G:
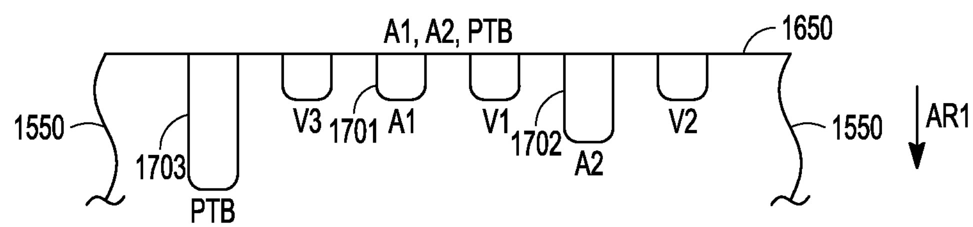
Figure 17H:
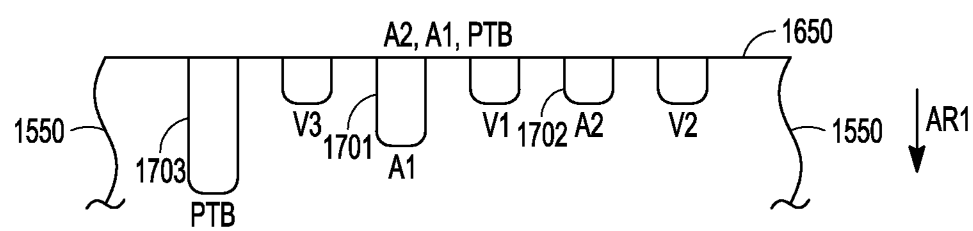
Figure 17I:
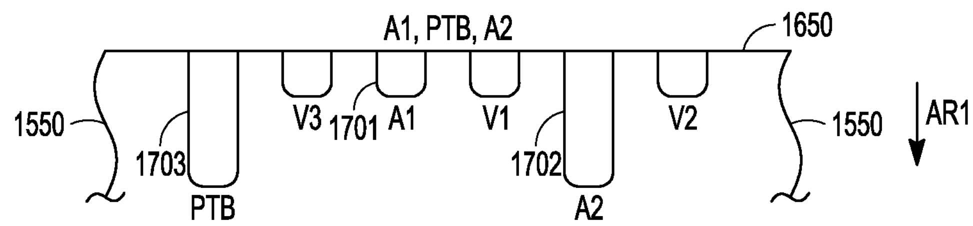
Figure 17J:
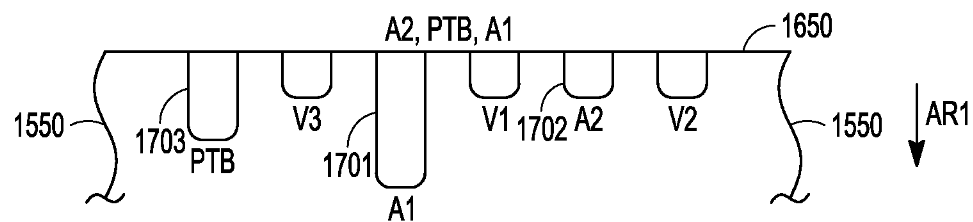
Figure 17K:
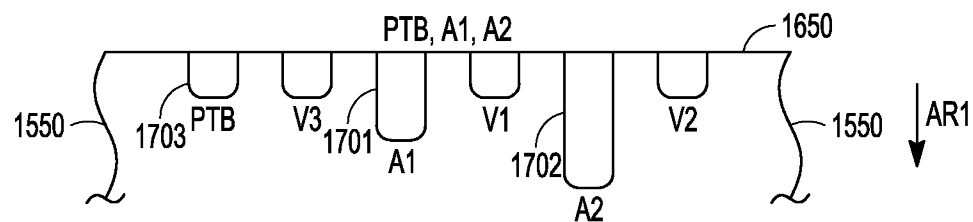
Figure 17L:
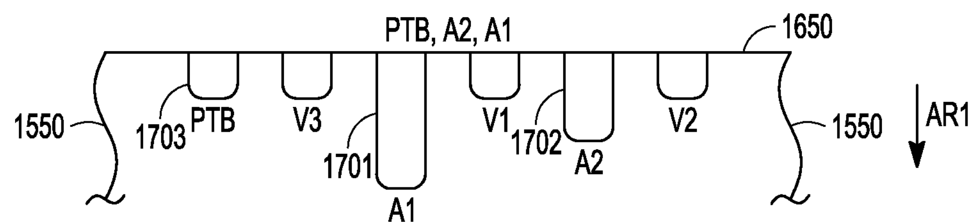
Figure 17M:
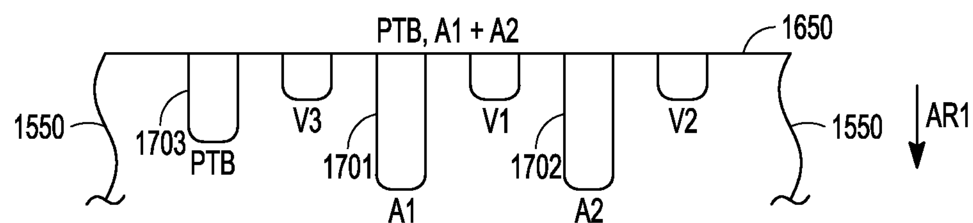

As shown in FIG. 17M (described further below), the distal edge 1650 of the constraining sheath 1550 is arranged to retract proximally in the direction of arrow AR1 parallel to the longitudinal axis of the valve during tab deployment. In FIG. 17M, the first and second anterior tabs A1, A2 may have the same length as each other, and the posterior tab PTB may have a shorter length than the first and second anterior tabs A1, A2, and/or the free end 1703 of the posterior tab PTB may be closer to the annular region than the free ends 1701, 1702 of the first and second anterior tabs A1, A2. Therefore, as the distal edge 1650 of the constraining sheath 1550 retracts proximally in the direction of arrow AR1 parallel to the longitudinal axis of the valve, the first and second anterior tabs A1, A2 are concurrently fully deployed after the posterior tab PTB is fully deployed. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

In some examples, the lengths of the tabs and/or the axial positions of the ventricular ends of the tabs may be varied such that one of the two anterior tabs A1, A2 may have the same length as the posterior tab PTB and/or their free ends may be in the same axial position. In this case, one of the two anterior tabs A1, A2 is fully deployed concurrently with the posterior tab PTB. The lengths of the tabs and/or the axial positions of the free ends of the tabs may be varied such that the second of the anterior tabs A1, A2 may be allowed to fully deploy before or after the concurrent full deployment of the first of the anterior tabs A1, A2 and the posterior tab PTB.

As shown in FIG. 17C, the distal edge 1650 of the constraining sheath 1550 is arranged to retract proximally in the direction of arrow AR1 parallel to the longitudinal axis of the valve during tab deployment. In FIG. 17C, the first anterior tab A1 may have the same length as the posterior tab PTB and/or their free ends 1701, 1703 may be in the same axial position. The second anterior tab A2 may have a greater length than the first anterior tab A1 and the posterior tab PTB and/o its free end 1702 may be further from the annular region than the free ends 1701, 1703 of the first anterior tab A1 and the posterior tab PTB. In this case, as the distal edge 1650 of the constraining sheath 1550 is retracted proximally in the direction of arrow AR1 parallel to the longitudinal axis of the valve, the first anterior tab A1 fully deploys concurrently with the posterior tab PTB, and the second anterior tab A2 fully deploys after them. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17D, the distal edge 1650 of the constraining sheath 1550 is arranged to retract proximally in the direction of arrow AR1 parallel to the longitudinal axis of the valve during tab deployment. In FIG. 17D, the second anterior tab A2 and the posterior tab PTB may have the same length as each other, as the first anterior tab A1 may have a longer length than the second anterior tab A2 and the posterior tab PTB, and/or the free ends 1702, 1703 of the second anterior tab A2 and the posterior tab PTB may be closer to the annular region than the free end 1701 of the first anterior tab A1. Therefore, as the distal edge 1650 of the constraining sheath retracts proximally in the direction of arrow AR1 parallel to the longitudinal axis of the valve, the second anterior tab A2 fully deploys concurrently with the posterior tab PTB, and the first anterior tab A1 fully deploys after. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17E, the distal edge 1650 of the constraining sheath 1550 is arranged to retract proximally in the direction of arrow AR1 parallel to the longitudinal axis of the valve during tab deployment. In FIG. 17E, the second anterior tab A2 and the posterior tab PTB may have the same length as each other and the first anterior tab A1 may have a shorter length than the second anterior tab A2 and the posterior tab PTB, and/or the free ends 1702, 1703 of the second anterior tab A2 and the posterior tab PTB may be further from the annular region than the free end 1701 of the first anterior tab A1. Therefore, as the distal edge 1650 of the constraining sheath retracts proximally in the direction of arrow AR1 parallel to the longitudinal axis of the valve, the first anterior tab A1 fully deploy first, followed by the second anterior tab A2 and the posterior tab PTB concurrently. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17F, the distal edge 1650 of the constraining sheath 1550 is arranged to retract proximally in the direction of arrow AR1 parallel to the longitudinal axis of the valve during tab deployment. In FIG. 17F, the first anterior tab A1 and the posterior tab PTB may have the same length as each other and the second anterior tab A1 may have a shorter length than the first anterior tab A1 and the posterior tab PTB, and/or the free ends 1701, 1703 of the first anterior tab A1 and the posterior tab PTB may be further from the annular region than the free end 1702 of the second anterior tab A2. Therefore, as the distal edge 1650 of the constraining sheath retracts proximally in the direction of arrow AR1 parallel to the longitudinal axis of the valve, the second anterior tab A2 fully deploy first, followed by the first anterior tab A1 and the posterior tab PTB concurrently. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

In some examples, the lengths of the tabs and/or the axial positions of the ventricular ends of the tabs may be varied such that one of the two anterior tabs A1, A2 is fully deployed before the posterior tab PTB. The lengths of the tabs and/or the axial positions of the ventricular ends of the tabs may be varied such that the second of the anterior tabs A1, A2 may be allowed to fully deploy before or after the full deployment of the posterior tab PTB.

As shown in FIG. 17G, the distal edge 1650 of the constraining sheath 1550 is arranged to retract proximally in the direction of arrow AR1 parallel to the longitudinal axis of the valve during tab deployment. In FIG. 17G, the posterior tab PTB may be longer than the second anterior tab A2 which may be longer than the first anterior tab A1, and/or the free end 1703 of the posterior tab PTB may be further from the annular region than the free end 1702 of the second anterior tab A2 which may be further from the annular region than the free end 1701 of the first anterior tab A1. In this case, as the distal edge 1650 of the constraining sheath 1550 is retracted proximally in the direction of arrow AR1 parallel to the longitudinal axis of the valve, the first anterior tab A1 fully deploys first with the edges of V1, V2, V3 of the ventricular skirt, followed by the second anterior tab A2, and then followed by the posterior tab PTB. The edges V1, V2, V3 of the ventricular skirt are closer to the annular region than the free ends 1702, 1703 of the second anterior tab, A2, and the posterior tab PTB such that, as the sheath 1550 is retracted, the ventricular skirt is configured to deploy concurrently with A1 and before the tabs A2, PTB finish expanding.

As shown in FIG. 17H, the distal edge 1650 of the constraining sheath 1550 is arranged to retract proximally in the direction of arrow AR1 parallel to the longitudinal axis of the valve during tab deployment. In FIG. 17H, the posterior tab PTB may be longer than the first anterior tab A1 which may be longer than the second anterior tab A2, and/or the free end 1703 of the posterior tab PTB may be further from the annular region than the free end 1701 of the first anterior tab A1 which may be further from the annular region than the free end 1702 of the second anterior tab A2. In this case, as the distal edge 1650 of the constraining sheath 1550 is retracted proximally in the direction of arrow AR1 parallel to the longitudinal axis of the valve, the second anterior tab A2 fully deploy first with the edges of V1, V2, V3 of the ventricular skirt, followed by the first anterior tab A1, and then followed by the posterior tab PTB. The edges V1, V2, V3 of the ventricular skirt are closer to the annular region than the free ends 1701, 1703 of the first anterior tab A1, and the posterior tab PTB such that, as the sheath 1550 is retracted, the ventricular skirt is configured to deploy concurrently with A2 and before the tabs A1, PTB finish expanding.

As shown in FIG. 17I, the distal edge 1650 of the constraining sheath 1550 is arranged to retract proximally in the direction of arrow AR1 parallel to the longitudinal axis of the valve during tab deployment. In FIG. 17I, the second anterior tab A2 may be longer than the posterior tab PTB which may be longer than the first anterior tab A1, and/or the free end 1702 of the second anterior tab A2 may be further from the annular region than the free end 1703 of the posterior tab PTB which may be further from the annular region than the free end 1701 of the first anterior tab. In this case, as the distal edge 1650 of the constraining sheath 1550 is retracted proximally in the direction of arrow AR1 parallel to the longitudinal axis of the valve, the first anterior tab A1 fully deploys first with the edges of V1, V2, V3 of the ventricular skirt, followed by the posterior tab PTB, and the second anterior tab A2. The edges V1, V2, V3 of the ventricular skirt are closer to the annular region than the free ends 1702, 1703 of the second anterior tab A2 and posterior tab PTB such that, as the sheath 1550 is retracted, the ventricular skirt is configured to deploy concurrently with A1 and before the tabs A2 and PTB finish expanding.

As shown in FIG. 17J, the distal edge 1650 of the constraining sheath 1550 is arranged to retract proximally in the direction of arrow AR1 parallel to the longitudinal axis of the valve during tab deployment. In FIG. 17J, the first anterior tab A1 may be longer than the posterior tab PTB which may be longer than the second anterior tab A2, and/or the free end 1701 of the first anterior tab A1 may be further from the annular region than the free end 1703 of the posterior tab PTB which may be further from the annular region than the free end 1702 of the second anterior tab A2. In this case, as the distal edge 1650 of the constraining sheath 1550 is retracted proximally in the direction of arrow AR1 parallel to the longitudinal axis of the valve, the second anterior tab A2 fully deploys first with the edges of V1, V2, V3 of the ventricular skirt, followed by the posterior tab PTB, and then followed by the first anterior tab A1. The edges V1, V2, V3 of the ventricular skirt are closer to the annular region than the free ends 1701, 1703 of the first anterior tab A1, and posterior tab PTB such that, as the sheath 1550 is retracted, the ventricular skirt is configured to deploy concurrently with A2 and before the tabs A1, PTB finish expanding.

In some examples, the lengths of the tabs and/or the axial positions of the ventricular ends of the tabs may be varied such that the posterior tab PTB is fully deployed first. The lengths of the tabs and/or the axial positions of the ventricular ends of the tabs may be varied such that the anterior tabs A1, A2 fully deploy either sequentially or concurrently after the full deployment of the posterior tab PTB.

As shown in FIG. 17K, the distal edge 1650 of the constraining sheath 1550 is arranged to retract proximally in the direction of arrow AR1 parallel to the longitudinal axis of the valve during tab deployment. In FIG. 17K, the second anterior tab A2 may be longer than the first anterior tab A1 which may be longer than the posterior tab PTB, and/or the free end 1702 of the second anterior tab A2 may be further from the annular region than the free end 1701 of the first anterior tab A1 which may be further from the annular region than the free end 1703 of the posterior tab PTB. In this case, as the distal edge 1650 of the constraining sheath 1550 is retracted proximally in the direction of arrow AR1 parallel to the longitudinal axis of the valve, the posterior tab PTB fully deploys first with the edges of V1, V2, V3 of the ventricular skirt, followed by the first anterior tab A1 and then the second anterior tab A2. The edges V1, V2, V3 of the ventricular skirt are closer to the annular region than the free ends 1701, 1702, of the first and second anterior tabs A1, A2 such that, as the sheath 1550 is retracted, the ventricular skirt is configured to deploy concurrently with PTB and before the tabs A1 and A2 finish expanding.

As shown in FIG. 17L, the distal edge 1650 of the constraining sheath 1550 is arranged to retract proximally in the direction of arrow AR1 parallel to the longitudinal axis of the valve during tab deployment. In FIG. 17L, the first anterior tab A1 may be longer than the second anterior tab A2 which may be longer than the posterior tab PTB, and/or the free end 1701 of the first anterior tab A1 may be further from the annular region than the free end 1702 of the second anterior tab A2 which may be further from the annular region than the free end 1703 of the posterior tab PTB. In this case, as the distal edge 1650 of the constraining sheath 1550 is retracted proximally in the direction of arrow AR1 parallel to the longitudinal axis of the valve, the posterior tab PTB fully deploys first with the edges of V1, V2, V3 of the ventricular skirt, followed by the second anterior tab A2 and then the first anterior tab A1. The edges V1, V2, V3 of the ventricular skirt are closer to the annular region than the free ends 1701, 1702 of the first and second anterior tabs A1, A2 such that, as the sheath 1550 is retracted, the ventricular skirt is configured to deploy concurrently with PTB and before the tabs A1 and A2 finish expanding.

As shown in FIG. 17M, the distal edge 1650 of the constraining sheath 1550 is arranged to retract proximally in the direction of arrow AR1 parallel to the longitudinal axis of the valve during tab deployment. In FIG. 17M, the first anterior tab A1 and the second anterior tab A2 may have the same length and both may be longer than the posterior tab PTB, and/or the free end 1701 of the first anterior tab A1 and the free end 1702 of the second anterior tab A2 may be the same distance from the annular region and both may be further from the annular region than the free end 1703 of the posterior tab. In this case, the posterior tab PTB fully deploys first with the edges of V1, V2, V3 of the ventricular skirt, followed by the first anterior tab A1 and the second anterior tab A2 concurrently. The edges V1, V2, V3 of the ventricular skirt are closer to the annular region than the free ends 1701, 1702 of the first and second anterior tabs A1, A2 such that, as the sheath 1550 is retracted, the ventricular skirt is configured to deploy concurrently with PTB and before the tabs A1 and A2 finish expanding.

While FIGS. 17A-17M show the ventricular skirt (and its edges V1, V2, V3) deploying concurrently with the first deployed tab or before any of the tabs, the ventricular skirt may be configured to deploy in any order, for example, before any combination of the tabs, after any combination of the tabs, and/or concurrently with any of the tabs. One or more of the sides V1, V2, and V3 may deploy before the remaining sides.

As described above and herein, the anterior and posterior tabs may partially deploy upon retraction of the constraining sheath 1550, such as to deploy to an orientation transverse to the longitudinal axes of the prosthetic cardiac valve and the constraining sheath. This partially deployed position of the tabs may position the tabs relative to one or more of the anterior leaflet AL, the posterior leaflet PL, or the adjacent chordae tendinae for subsequent engagement and capture by the tabs upon full deployment. One or more of the partially deployed anterior or posterior tabs may be visualized to confirm proper positioning and/or orientation of the prosthetic cardiac valve and its tabs. If needed, the prosthetic valve may be repositioned and/or reoriented with the initial tab(s) deployed (and the remaining tab(s) yet to be deployed) based on the imaging or visualization. In response to the visualization, the prosthetic cardiac valve may be repositioned and/or reoriented. The anterior and posterior tabs may partially deploy in any order and in any combination with any order of the full deployment of the tabs as described above with respect to FIGS. 17A-17B. For the ease of illustration in the following described FIGS. 18A-18M, the first and second anterior tabs A1, A2 (particularly their atrial ends 1801, 1802) and the posterior tab PTB (particularly its atrial end 1803) are shown in a rolled out configuration relative to a retracting constraining sheath 1550 to show various orders of partial deployment of the first and second anterior tabs A1, A2 and the posterior tab PTB.

In some examples, the lengths of the tabs and/or the axial positions of the atrial ends of the tabs may be varied such that two or more of the two anterior tabs A1, A2 and the posterior tab PTB are partially deployed concurrently.

Figure 18A:
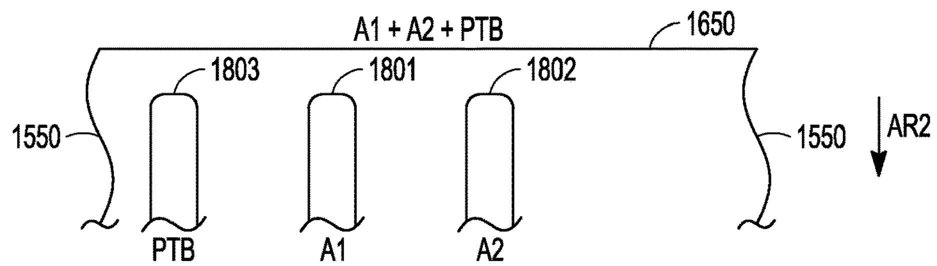
FIGS. 18A-18M schematically illustrate variations of different sequences for partially deploying a first anterior tab, a second anterior tab, and a posterior tab of a prosthetic cardiac valve, according to many examples.

As shown in FIG. 18A, the distal edge 1650 of the constraining sheath 1550 is arranged to retract proximally in the direction of arrow AR2 parallel to the longitudinal axis of the valve during tab deployment. In FIG. 18A, the first and second anterior tabs A1, A2 and the posterior tab PTB may have the same lengths, and/or their atrial ends 1801, 1802, 1803 may be in the same axial position away from the annular region. The first and second anterior tabs A1, A2 and the posterior tab PTB will partially deploy concurrently with one another as the constraining sheath 1550 is retracted.

Figure 18B:
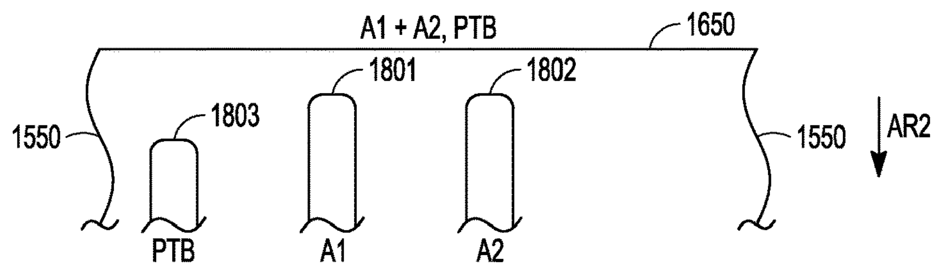

As shown in FIG. 18B, the distal edge 1650 of the constraining sheath 1550 is arranged to retract proximally in the direction of arrow AR2 parallel to the longitudinal axis of the valve during tab deployment. In FIG. 18B, the first and second anterior tabs A1, A2 may have the same lengths and both may be longer than the posterior tab PTB, and/or the atrial ends 1801, 1802 of both the first and second anterior tabs A1, A2 may be in the same axial position away from the annular region and both may be further from the annular region than the atrial end 1803 of the posterior tab PTB. The first and second anterior tabs A1, A2 will concurrently partially deploy before the posterior tab PTB is partially deployed as the constraining sheath 1550 is retracted.

Figure 18C:
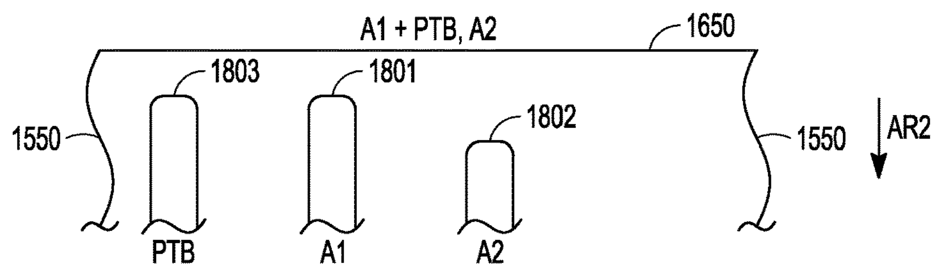
Figure 18D:
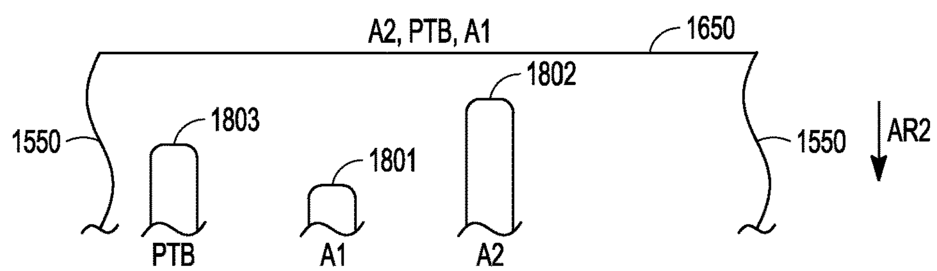
Figure 18E:
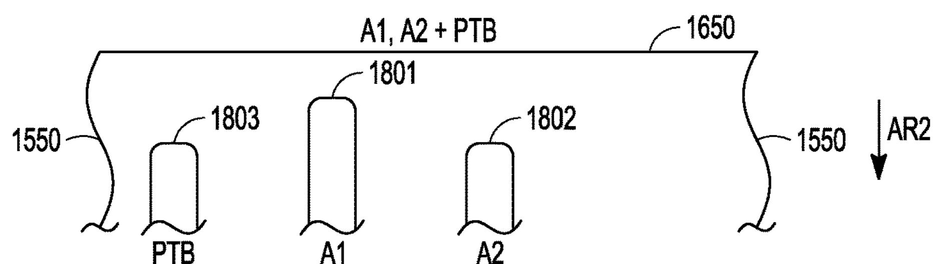
Figure 18F:
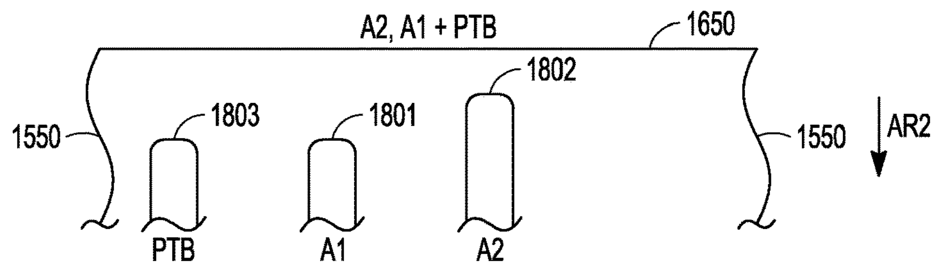
Figure 18G:
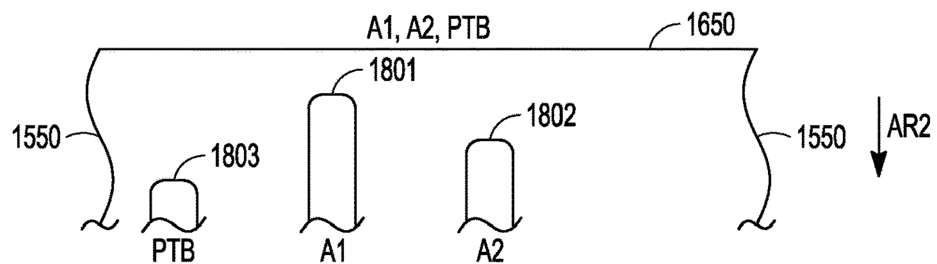
Figure 18H:
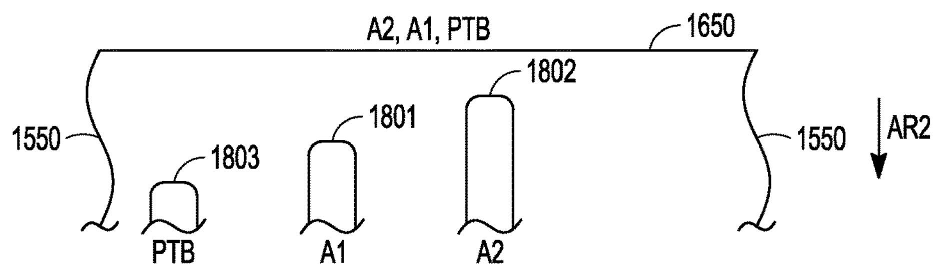
Figure 18I:
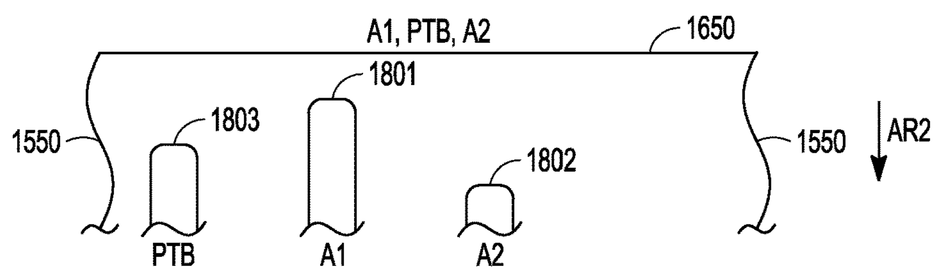
Figure 18J:
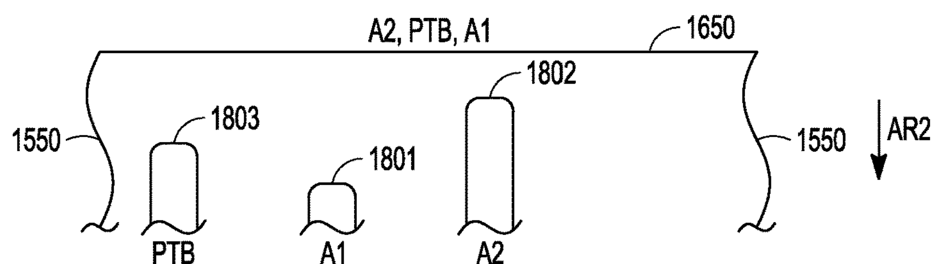
Figure 18K:
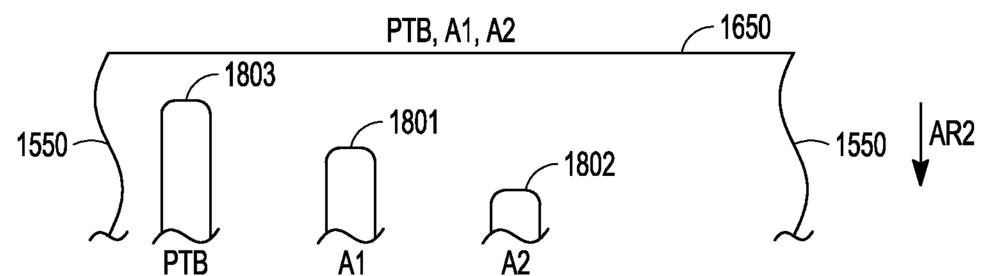
Figure 18L:
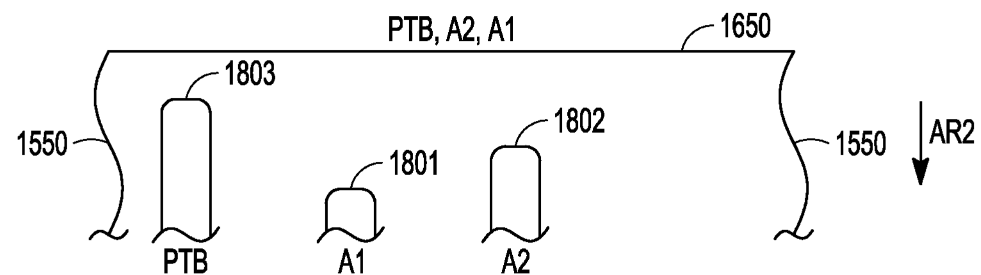
Figure 18M:
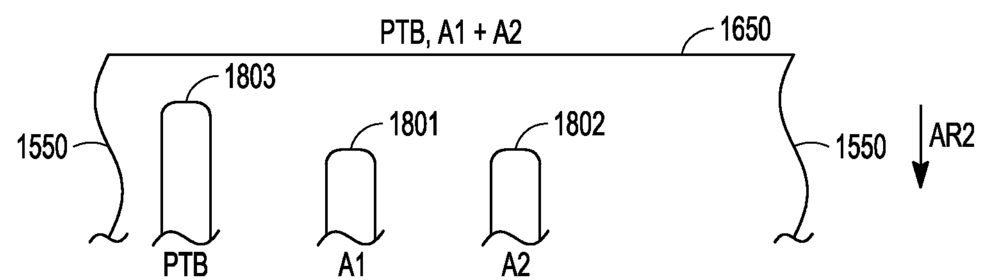

As shown in FIG. 18M (described further below), the distal edge 1650 of the constraining sheath 1550 is arranged to retract proximally in the direction of arrow AR2 parallel to the longitudinal axis of the valve during tab deployment. In FIG. 18M, the first and second anterior tabs A1, A2 may have the same lengths and both may be shorter than the posterior tab PTB, and/or the atrial ends 1801, 1802 of both the first and second anterior tabs A1, A2 may be in the same axial position away from the annular region and both may be closer to the annular region than the atrial end 1803 of the posterior tab PTB. The first and second anterior tabs A1, A2 will concurrently partially deploy after the posterior tab PTB is partially deployed as the constraining sheath 1550 is retracted.

In some examples, the lengths of the tabs and/or the axial positions of the atrial ends of the tabs may be varied such that one of the two anterior tabs A1, A2 is partially deployed concurrently with the posterior tab PTB. The lengths of the tabs and/or the axial positions of the atrial ends of the tabs may be varied such that the second of the anterior tabs A1, A2 may be allowed to partially deploy before or after the concurrent partial deployment of the first of the anterior tabs A1, A2 and the posterior tab PTB.

As shown in FIG. 18C, the distal edge 1650 of the constraining sheath 1550 is arranged to retract proximally in the direction of arrow AR2 parallel to the longitudinal axis of the valve during tab deployment. In FIG. 18C, the first anterior tab A1 and the posterior tab PTB may have the same lengths and both may be longer than the second anterior tab A2, and/or the atrial ends 1801, 1803 of both the first anterior tab A1 and posterior tab PTB may be in the same axial position away from the annular region and both may be further from the annular region than the atrial end 1802 of the second anterior tab A2. The first anterior tab A1 will partially deploy concurrently with the posterior tab PTB and the second anterior tab A2 will partially deploys after as the constraining sheath 1550 is retracted.

As shown in FIG. 18D, the distal edge 1650 of the constraining sheath 1550 is arranged to retract proximally in the direction of arrow AR2 parallel to the longitudinal axis of the valve during tab deployment. In FIG. 18D, the second anterior tab A2 may be the same length as the posterior tab PTB, both of which may be longer than the first anterior tab A1, and/or the atrial end 1802 of the second anterior tab A2 may be in an axial position relative to the annular region that is the same as the axial position of the atrial end 1803 of the posterior tab PTB, both of which may be in an axial position further from the annular region than the atrial end 1801 of the first anterior tab A1. The second anterior tab A2 will partially deploy concurrently with the posterior tab PTB and the first anterior tab A1 will partially deploy after as the constraining sheath 1550 is retracted.

As shown in FIG. 18E, the distal edge 1650 of the constraining sheath 1550 is arranged to retract proximally in the direction of arrow AR2 parallel to the longitudinal axis of the valve during tab deployment. In FIG. 18E, the second anterior tab A2 and the posterior tab PTB may have the same length and both may be shorter than the first anterior tab A1, and/or the atrial ends 1802, 1803 of the second anterior tab A2 and the posterior tab PTB may be in the same axial positions away from the annular region which are closer to the annular region than the atrial end 1801 of the first anterior tab A1. The first anterior tab A1 will partially deploy first, followed by the second anterior tab A2 and the posterior tab PTB concurrently, as the constraining sheath 1550 is retracted.

As shown in FIG. 18F, the distal edge 1650 of the constraining sheath 1550 is arranged to retract proximally in the direction of arrow AR2 parallel to the longitudinal axis of the valve during tab deployment. In FIG. 18F, the first anterior tab A1 and the posterior tab PTB may have the same length and both may be shorter than the second anterior tab A2, and/or the atrial ends 1801, 1803 of the first anterior tab A1 and the posterior tab PTB may be in the same axial positions away from the annular region which are closer to the annular region than the atrial end 1802 of the second anterior tab A2. The second anterior tab A2 will partially deploy first, followed by the first anterior tab A1 and the posterior tab PTB concurrently, as the constraining sheath 1550 is retracted.

In some examples, the lengths of the tabs and/or the axial positions of the atrial ends of the tabs may be varied such that one of the two anterior tabs A1, A2 is partially deployed before the posterior tab PTB. The lengths of the tabs and/or the axial positions of the atrial ends of the tabs may be varied such that the second of the anterior tabs A1, A2 may be allowed to partially deploy before or after the full deployment of the posterior tab PTB.

As shown in FIG. 18G, the distal edge 1650 of the constraining sheath 1550 is arranged to retract proximally in the direction of arrow AR2 parallel to the longitudinal axis of the valve during tab deployment. In FIG. 18G, the first anterior tab A1 may be longer than the second anterior tab A2 which may be longer than the posterior tab PTB, and/or the atrial end 1801 of the first anterior tab A1 may be in an axial position away from the annular region further than the atrial end 1802 of the second anterior tab A2 which may be in an axial position further from the annular region than the atrial end 1803 of the posterior tab PTB. The first anterior tab A1 will partially deploy first, followed by the second anterior tab A2, and then followed by the posterior tab PTB, as the constraining sheath 1550 is retracted.

As shown in FIG. 18H, the distal edge 1650 of the constraining sheath 1550 is arranged to retract proximally in the direction of arrow AR2 parallel to the longitudinal axis of the valve during tab deployment. In FIG. 18H, the second anterior tab A2 may be longer than the first anterior tab A1 which may be longer than the posterior tab PTB, and/or the atrial end 1802 of the second anterior tab A2 may be in an axial position away from the annular region further than the atrial end 1801 of the first anterior tab A1 which may be in an axial position further from the annular region than the atrial end 1803 of the posterior tab PTB. The second anterior tab A2 will partially deploy first, followed by the first anterior tab A1, and then followed by the posterior tab PTB, as the constraining sheath 1550 is retracted.

As shown in FIG. 18I, the distal edge 1650 of the constraining sheath 1550 is arranged to retract proximally in the direction of arrow AR2 parallel to the longitudinal axis of the valve during tab deployment. In FIG. 18I, the first anterior tab A1 may be longer than the posterior tab PTB which may be longer than the second anterior tab A2, and/or the atrial end 1801 of the first anterior tab A1 may be in an axial position away from the annular region further than the atrial end 1803 of the posterior tab PTB which may be in an axial position further from the annular region than the atrial end 1802 of the second anterior tab A2. The first anterior tab A1 will partially deploy first, followed by the posterior tab PTB, and then followed by the second anterior tab A2, as the constraining sheath 1550 is retracted.

As shown in FIG. 18J, the distal edge 1650 of the constraining sheath 1550 is arranged to retract proximally in the direction of arrow AR2 parallel to the longitudinal axis of the valve during tab deployment. In FIG. 18J, the second anterior tab A2 may be longer than the posterior tab PTB which may be longer than the first anterior tab A1, and/or the atrial end 1802 of the second anterior tab A2 may be in an axial position away from the annular region further than the atrial end 1803 of the posterior tab PTB which may be in an axial position further from the annular region than the atrial end 1801 of the first anterior tab A1. The second anterior tab A2 will partially deploy first, followed by the posterior tab PTB, and then followed by the first anterior tab A1, as the constraining sheath 1550 is retracted.

In some examples, the lengths of the tabs and/or the axial positions of the atrial ends of the tabs may be varied such that the posterior tab PTB is partially deployed first. The lengths of the tabs and/or the axial positions of the atrial ends of the tabs may be varied such that the anterior tabs A1, A2 partially deploy either sequentially or concurrently after the partial deployment of the posterior tab PTB.

As shown in FIG. 18K, the distal edge 1650 of the constraining sheath 1550 is arranged to retract proximally in the direction of arrow AR2 parallel to the longitudinal axis of the valve during tab deployment. In FIG. 18K, the posterior tab PTB may be longer than the first anterior tab A1 which may be longer than the second anterior tab A2, and/or the atrial end 1803 of the posterior tab PTB may be in an axial position away from the annular region further than the atrial end 1801 of the first anterior tab A1 which may be in an axial position further from the annular region than the atrial end 1802 of the second anterior tab A2. The posterior tab PTB will partially deploy first, followed by the first anterior tab A1 and then the second anterior tab A2, as the constraining sheath 1550 is retracted.

As shown in FIG. 18L, the distal edge 1650 of the constraining sheath 1550 is arranged to retract proximally in the direction of arrow AR2 parallel to the longitudinal axis of the valve during tab deployment. In FIG. 18L, the posterior tab PTB may be longer than the second anterior tab A2 which may be longer than the first anterior tab A1, and/or the atrial end 1803 of the posterior tab PTB may be in an axial position away from the annular region further than the atrial end 1802 of the second anterior tab A2 which may be in an axial position further from the annular region than the atrial end 1801 of the first anterior tab A1. The posterior tab PTB will partially deploy first, followed by the second anterior tab A1 and then the first anterior tab A1, as the constraining sheath 1550 is retracted.

As shown in FIG. 18M, the distal edge 1650 of the constraining sheath 1550 is arranged to retract proximally in the direction of arrow AR2 parallel to the longitudinal axis of the valve during tab deployment. In FIG. 18M, the posterior tab PTB may be longer than the second anterior tab A2 which may the same length as the first anterior tab A1, and/or the atrial end 1803 of the posterior tab PTB may be in an axial position away from the annular region further than the atrial ends 1801, 1802 of the first anterior tab A1 and second anterior tab A2 which may be in the same axial positions from the annular region. The posterior tab PTB will partially deploy first, followed by the first anterior tab A1 and the second anterior tab A2 concurrently, as the constraining sheath 1550 is retracted.

The first and second anterior tabs A1, A2 and the posterior tab PTB may all partially deploy before any of the same tabs concurrently deploy. Alternatively, one or more of the first and second anterior tabs A1, A2 and the posterior tab PTB may partially deploy before one or more of the first and second anterior tabs A1, A2 and the posterior tab PTB fully deploys.

Ventricular Deployment.

In previous examples, the atrial portions of the prosthesis radially expand prior to the ventricular portions. Atrial deployment may be beneficial in certain situations. For example, atrial deployment allows the steadying of the heart while seating the prosthetic valve and can be easier to rotationally align the device with the native valve anatomy. Atrial deployment may also more evenly distribute force along the larger area of the atrial skirt instead of just along the three points of the anchor tabs. Nevertheless, in certain situations, it may be beneficial to deploy the ventricular portions before the atrial portions. The following examples illustrate potential ventricular sequences of ventricular deployment of a prosthetic valve which may be any of the prosthetic valves disclosed herein. The prosthetic valve may be a prosthetic mitral valve or any of the other prosthetic valves disclosed herein.

One advantage of deploying the ventricular portion first in any of the prosthetic valves disclosed herein is that this allows recapture and redeployment of any of the anchor tabs in the situation where they are incorrectly deployed. For example, the anchor tabs may become entangled with chordae or the tip of the anchor tab may land on the inside of the valve annulus instead of behind the native valve leaflet. In still other situations the anchor tabs may not be correctly rotationally oriented with the native anatomy (e.g. the anterior portion of the prosthetic valve may not be rotationally aligned with the anterior of the native valve). And thus, it would be beneficial to be able to recapture and redeploy any or all anchor tabs so ensure that they are properly deployed.

Other possible advantages of deploying the ventricular portions first including the potential to capture the native valve leaflets more easily. In examples where a backwards transapical delivery system is used, ventricular height is not generally a concern. Ventricular deployment also may require less occlusion time and may permit deployment without the use of rapid pacing. Ventricular deployment also may provide more opportunities to choose where the anchor tabs protrude past the chordae. Moreover, ventricular deployment may allow a reduction in the number of catheter shafts in the delivery system thereby decreasing overall profile of the catheter system (e.g. reduce French size).

Figure 19A:
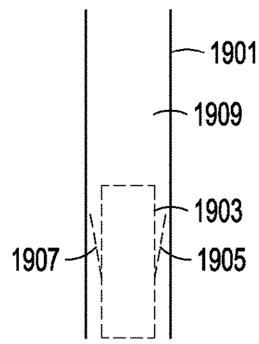
FIGS. 19A-19D illustrate a sequence of deployment of a prosthetic valve.

FIGS. 19A-19D illustrate a deployment sequence of a prosthetic valve. In FIG. 19A, the prosthetic valve 1903 is disposed in a lumen 1901 of a sheath 1901. The sheath constrains the prosthetic valve 1903 which also constrains a first anchor tab 1907 and a second anchor tab 1905 coupled to the prosthetic valve frame adjacent a ventricular region of the frame. The first anchor tab 1907 is an anterior anchor tab configured to extend through the chordae tendinae and behind the anterior native valve leaflet such that the tip of the anchor tab engages and anchors the prosthetic valve to the fibrous trigone. Optionally a second anterior tab may also be included (not shown) and it also may be configured to extend through the chordae tendinae and behind the anterior native valve leaflet such that the tip of the second anterior anchor tab engages and anchors the prosthetic valve to a second fibrous trigone opposite the other fibrous trigone. The other anchor tab 1905 is preferably a posterior anchor tab that is configured to extend through any chordae tendinae and behind the posterior native valve leaflet such that the tip of the posterior anchor tab engages and anchors the prosthetic valve to a posterior portion of the native valve annulus, such as the posterior shelf. The anterior and posterior anchor tabs generally take the same form as those previously described above. The anterior or posterior native valve leaflets may be disposed at least partially between the respective anchor tab and an outer surface of the prosthetic valve. The anchor tabs may take the same form as any of the other anchor tabs disclosed herein.

Figure 19B:
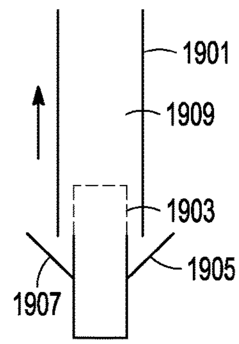

FIG. 19B illustrates proximal retraction of the sheath 1901 away from the prosthetic valve 1903 thereby removing the constraint from the two anchor tabs 1905, 1907 thereby allowing them to self-expand first.

Figures 19C, 19D:
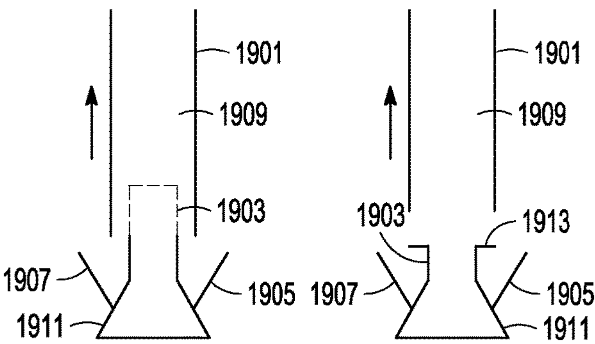

In FIG. 19C further proximal retraction of the sheath 1901 exposes an additional distal portion of the prosthesis 1903 thereby removing a constraint from the ventricular portion of the prosthesis such that the ventricular skirt 1911 may self-expand. The ventricular skirt 1911 is substantially the same as other ventricular skirts described in this specification.

Referring now to FIG. 19D, further proximal retraction of the sheath 1901 exposes the entire prosthesis 1903 and removes the constraint provided by the sheath 1901 thereby allowing the annular region and the atrial flange 1913 to self-expand. The annular region and the atrial flange substantially takes the same form as any of the atrial flanges and annular regions previously described.

Thus, the anchor tabs self-expand and deploy first followed by the ventricular skirt thereby helping to anchor the prosthesis to the native heart valve, here a native mitral valve from the ventricular side first followed by the atrial side. One of skill in the art will also appreciate that instead of a self-expanding prosthesis, the prosthesis may also be balloon expandable or expandable by other means known in the art.

In FIGS. 19A-19E, both anchor tabs open up concurrently. However, in some situations it may be preferable to deploy one tab before the other tab. FIGS. 20A-20E illustrate an example of this.

Figures 20A, 20B, 20C, 20D, 20E:
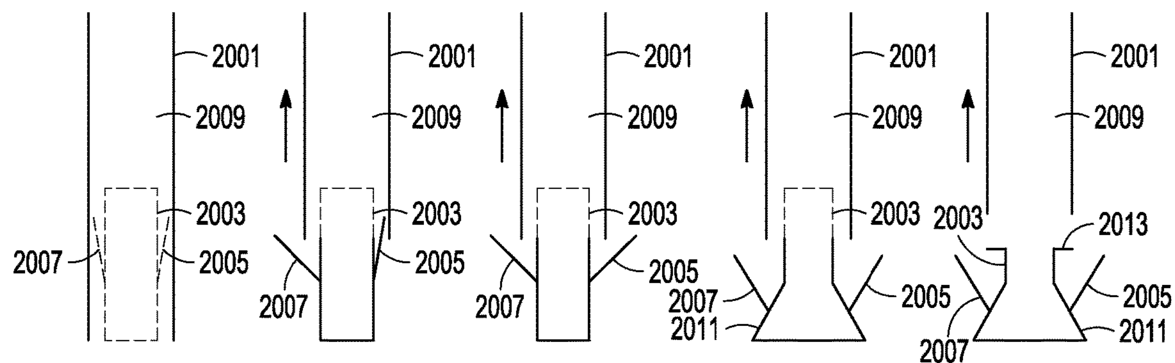
FIGS. 20A-20E illustrate another sequence of deployment of a prosthetic valve.

In FIG. 20A the prosthetic valve 2003 is disposed in a lumen 2009 of sheath 2001. The sheath constrains the prosthesis and prevents it from self-expanding as well as protects it during delivery. The prosthesis also includes a first anchor tab 2007 and a second anchor tab 2005. Both anchor tabs are also constrained by the sheath 2001 which prevents them from expanding and provides protection during delivery.

In FIG. 20B, proximal retraction of sheath 2001 exposes the first anchor tab 2007 allowing it to self-expand while maintaining adequate constraint of the ventricular skirt and the second anchor tab 2005 to prevent expansion thereof. The first anchor tab is preferably an anterior anchor tab that is configured to engage and anchor on the fibrous trigone of a native mitral valve, substantially the same as described previously. It may expand into a substantially horizontal position first and then spring further outward into a generally vertical position as shown. Optionally, the prosthetic valve may also have a second anterior tab as described above.

Further retraction as shown in FIG. 20C exposes the second anchor tab 2005 and allows it to self-expand while maintaining adequate constraint over the ventricular skirt to prevent it from expanding. As discussed above, preferably the second anchor tab 2005 may initial expand into a substantially horizontal position and then expand into a substantially vertical position as shown. Additionally, the second anchor tab is preferably a posterior anchor tab configured to engage and anchor on the posterior annulus of a native mitral valve as described previously.

For both the first and second anchor tabs, tab axial position, length, cross-section, heat treatment, etc. can be programmed into the prosthesis to control the expansion sequence.

Further retraction of sheath 2001 shown in FIG. 20D removes the constraint from the ventricular skirt 2011 thereby allowing it to self-expand while the atrial portion of the prosthesis remains constrained. Other aspects of the ventricular skirt are generally the same as previously described in this specification.

In FIG. 20E further retraction of sheath 2001 removes the constraint from the remainder of the prosthetic valve 2003 thereby allowing the annular region and the atrial flange 2013 to self-expand. The annular region and the atrial flange generally take the same form as previously described in this specification.

Thus, the anchor tabs self-expand serially followed by the ventricular skirt thereby helping to anchor the prosthesis to the native heart valve, here a native mitral valve is deployed from the ventricular side first followed by the atrial side. One of skill in the art will also appreciate that instead of a self-expanding prosthesis, the prosthesis may also be balloon expandable or expandable by other means known in the art.

FIGS. 21A-21E illustration a variation in FIGS. 20A-20E where the second anchor tab deploys before the first anchor tab.

Figures 21A, 21B, 21C, 21D, 21E:
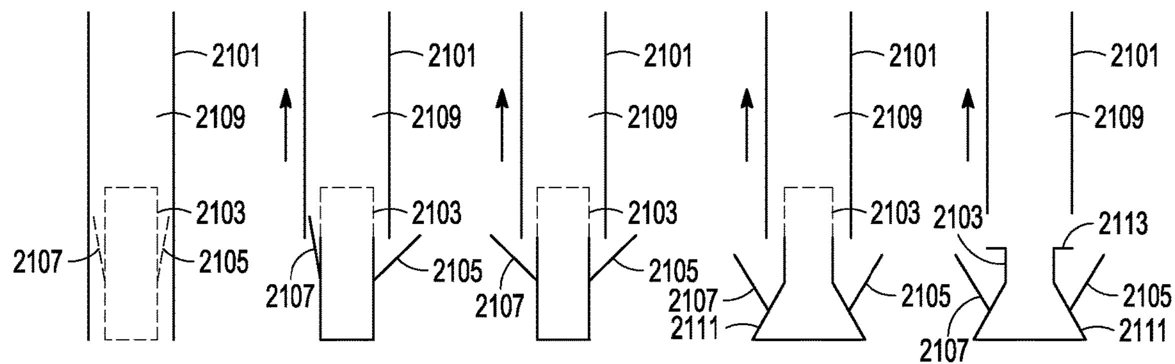
FIGS. 21A-21E illustrate still another sequence of deployment of a prosthetic valve.

In FIG. 21A a prosthetic valve 2103 is disposed in a lumen 2109 of a sheath 2101 thereby constraining the prosthetic valve 2102. The first anchor tab 2107 and the second anchor tab 2105 are also constrained by the sheath 2101 and prevented from expanding.

In FIG. 21B proximal retraction of the sheath 2101 removes the constraint from the second anchor tab 2105 allowing it to self-expand. It may initially extend horizontally outward and then self-expand into a substantially vertical position as shown. The first anchor tab 2017 remains constrained and does not self-expand.

FIG. 21C shows that further proximal retraction of the sheath 2101 removes the constraint from the first anchor tab and allows it to self-expand. Similar to the second anchor tab, the first anchor tab may initially self-expand into a substantially horizontal position and then fully expand into a substantially vertical position as shown.

Further proximal retraction of the sheath 2101 removes the constraint from the ventricular skirt 2111 allowing it to self-expand as shown in FIG. 21D FIG. 21E shows that further retraction of sheath 2101 removes the constraint from the remainder of the prosthesis 2103 allowing the annular region and the atrial flange 2113 to self-expand.

As discussed above, preferably the first anchor tab is an anterior anchor tab and preferably the second anchor tab is a posterior anchor tab, both tabs generally take the same form as discussed previously in this specification. Additionally, and optionally, the prosthesis may also have a second anterior anchor tab as also discussed above. Moreover, anchor tab length, axial position, cross-section, etc. affect the sequence of deployment and these can be selected during manufacturing in order to provide the desired deployment sequence.

Furthermore, as discussed above, the examples discussed herein are preferably self-expanding but one of skill in the art will appreciate that they also may be balloon expandable or expanded by other means known in the art.

Figures 22A, 22B:
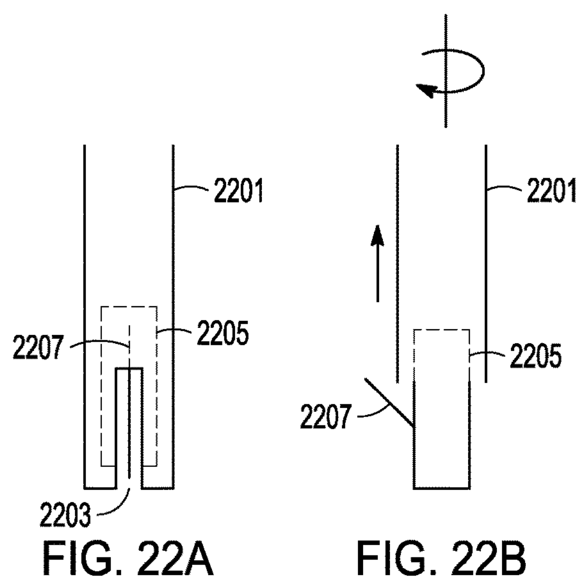
FIGS. 22A-22B illustrate an example of tab deployment.

In addition to the valve frame design, the delivery system may be engineered to preferentially allow selected regions of the prosthesis to expand in an order as illustrated in FIGS. 22A-22B.

In FIG. 22A a prosthesis which may be any of those disclosed herein is disposed in a sheath 2201. The sheath constrains the tip of the anchor tab 2207 but also has a slotted region 2203 extending parallel to the longitudinal axis of the sheath. Thus, proximal retraction of the sheath as seen in FIG. 22B allows the constraint to be removed from the anchor tab 2207 first thereby allowing the anchor tab to self-expand before other portions of the prosthesis. FIG. 22B is the same form as in FIG. 22A except that it has been rotated 90 degrees to show a side view of the anchor tab deployed. The slotted regions may be located at any position on the sheath to control the constraint and expansion of any portion of the prosthesis such as the anchor tabs or other regions.

Figures 23A, 23B, 23C:
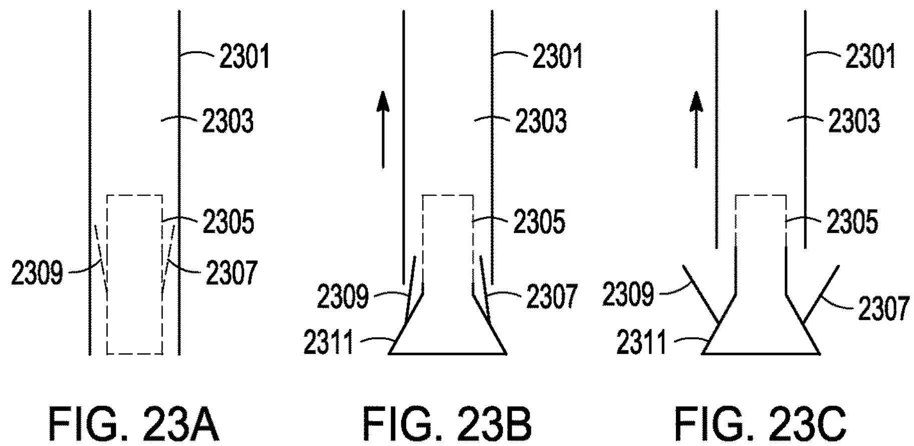
FIGS. 23A-23C illustrate yet another example of deployment of a prosthetic valve.

In the previous examples, the anchor tabs expand before the ventricular skirt. However, in certain circumstances it may be desired to have the ventricular skirt expand first. FIGS. 23A-23C illustrate an example of ventricular skirt deployment.

In FIG. 23A a prosthetic valve 2305 is disposed in a lumen 2303 of a sheath 2301. The sheath 2301 constrains the prosthetic valve 2305 and prevents expansion of the prosthesis including the first anchor tab 2309 and the second anchor tab 2307. As before, preferably the prosthesis is any of the mitral valve prostheses described in this specification. And preferably the first anchor tab 2309 is an anterior anchor tab and the second anchor tab 2307 is a posterior anchor tab such as those described in this specification. Optionally the prosthesis may also have a second anterior anchor tab that is not illustrated because it is not seen in this view.

Anchor tab axial position, length, cross-section, etc. affect the sequence of deployment. In this example, the anchors are positioned such that proximal retraction of sheath 2301 removes the constraint from the ventricular skirt allowing ventricular skirt 2311 to self-expand first as shown in FIG. 23B.

Further retraction of sheath 2301 as seen in FIG. 23C removes the remainder of the constraint thereby allowing both the first anchor tab 2309 and the second anchor tab 2311 to radially expand. In this example the two anchor tabs 2309, 2311 radially expand concurrently, however any sequence may be used such as either one first followed by the other. Additionally, the prosthesis may have another anchor tab (not illustrated) in the case where two anterior anchor tabs is desired, and any deployment sequence disclosed herein may be utilized. Further retraction of the sheath will remove the constraint from the rest of the prosthesis allowing the annular regions and atrial flange to expand afterwards (not illustrated).

Any number of delivery systems may be used to help control deployment of the prosthesis. For example, a hollow capsule may be used to carry the prosthesis to the treatment site and then the capsule may be opened to allow deployment in a desired sequence. Capsule delivery systems are disclosed in US Patent Publication No. 2017/0165064, the entire contents of which are incorporated herein by reference. While the capsules disclosed in US Patent Publication No. 2017/0165064 generally provide for atrial deployment of a prosthesis first, one of skill in the art will appreciate that they can be modified to provide for ventricular deployment of a prosthesis first.

Figures 24A, 24B, 24C:
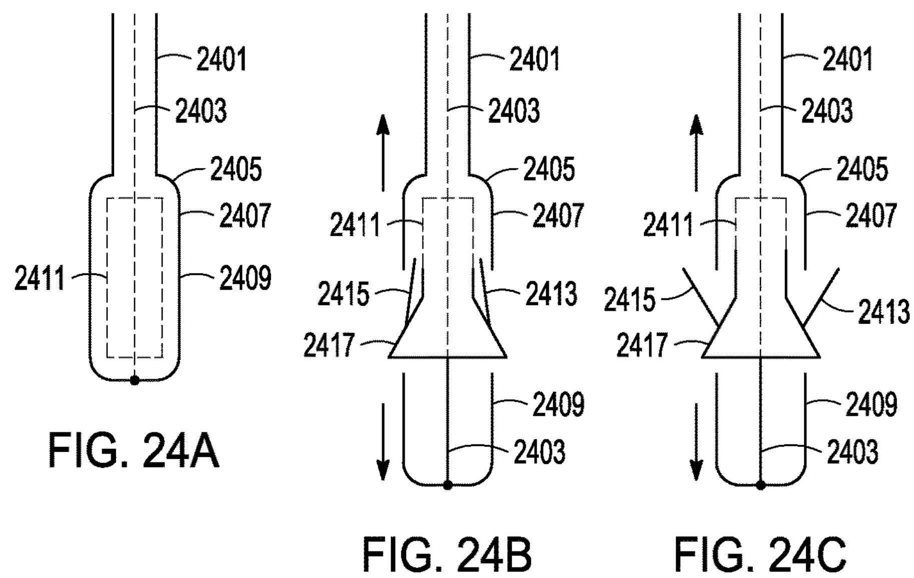
FIGS. 24A-24C illustrate a delivery system for a prosthetic valve.

FIGS. 24A-24C illustrate an example of a capsule delivery system used to deliver a prosthetic valve with ventricular deployment first.

FIG. 24A illustrates a prosthetic valve 2411 disposed in a hollow capsule 2405. The capsule carries the prosthesis to the target treatment area and protects it during delivery as well as providing a constraint to keep the prosthesis in a collapsed configuration and prevent self-expansion. The prosthesis is preferably a prosthetic mitral valve and may be any of the examples disclosed herein. The hollow capsule 2405 includes a proximal portion 2407 and a distal portion 2409. An inner shaft 2403 is coupled with the distal capsule portion 2409 and an outer shaft 2401 is coupled to the proximal capsule portion 2405. The inner and outer shafts slide relative to one another. The proximal and distal portions of the capsule are separable from one another as will be discussed below.

In FIG. 24B the distal capsule portion 2409 is moved distally relative to the proximal capsule portion 2405 (and/or the proximal capsule portion 2407 is moved proximally relative to the distal capsule portion) to separate the two halves and remove the constraint from the ventricular region of the prosthetic valve 2411 thereby allowing the ventricular skirt 2417 to self-expand while the first and second anchor tabs 2415, 2417 remain constrained and do not self-expand as well as the atrial and annular portions. The capsule halves may be moved by relative movement of the inner shaft 2403 or outer shaft 2401.

In FIG. 24C further separation of the proximal and distal capsule portions further removes the constraint from the prosthetic valve allowing the first and second anchor tabs 2415, 2417 to self-expand. Further separation of the capsule halves will then allow the annular region and the atrial flange to self-expand (not shown). As discussed previously, preferably the first anchor tab is an anterior anchor tab and the second anchor tab is preferably a posterior anchor tab. Optionally the prosthetic valve also includes a second anterior anchor tab. The anchor tabs generally take the same form as discussed above. Moreover, any deployment sequence of the anchor tabs may be used in this example including those described previously.

Figure 25A:
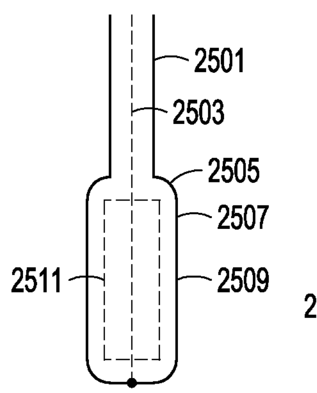
FIGS. 25A-25C illustrate another delivery system for a prosthetic valve.
Figure 25B:
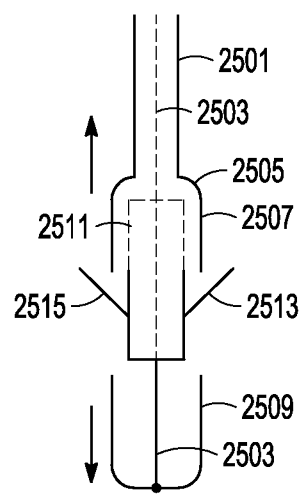
Figure 25C:
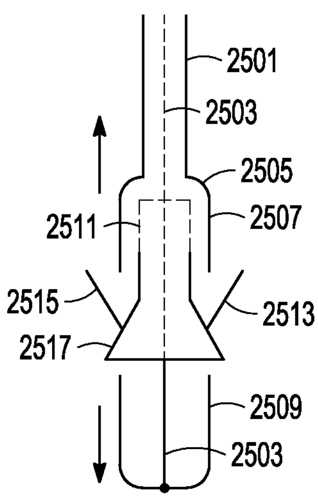

In certain situations, it may be beneficial to allow deployment of the anchor tabs before deployment of the ventricular skirt, as seen in FIGS. 25A-25C.

FIG. 25A shows a delivery system having a capsule 2505 for carrying a prosthetic valve 2511. The capsule includes a proximal capsule portion 2507 and a distal capsule portion 2509 that are separable from one another. An inner shaft 2503 is coupled to the distal capsule portion 2509 and an outer shaft 2501 is coupled with the proximal capsule portion 2505. The inner and outer shafts 2501, 2503 slide relative to one another.

In FIG. 25B, the distal capsule portion is separated from the proximal capsule portion 2507 to remove the constraint from a portion of the prosthetic valve 2511 thereby allowing the anchor tabs 2515, 2513 to self-expand while the ventricular skirt 2517 remains constrained. As discussed above, preferably the first anchor tab 2515 is an anterior anchor tab and preferably the second anchor tab 2513 is a posterior anchor tab. Optionally the prosthetic valve may include a second anterior anchor tab (not shown). The first and second anchor tabs may take the form of any anchor tabs previously described above.

Further separation of the proximal and distal capsules 2507, 2509 allows the ventricular skirt 2517 to become unconstrained and to self-expand next as seen in FIG. 25C. The remainder of the prosthetic valve expands with further separation of the capsule halves including the annular region and the atrial flange last (not illustrated).

FIG. 25D1 shows a delivery system having a distal capsule portion 2601 and proximal capsule portion 2505 for carrying a prosthetic valve 1506 and constraining the atrial portion of the prosthetic valve from deploying first while allowing the ventricular portion to deploy first. An inner shaft 2518 is coupled to the distal capsule portion 2601. The distal capsule portion 2601 contains a proximal edge with a straight proximal edge 2325. FIG. 25D2 shows the three-dimensional sketch and the two-dimensional sketch of the straight proximal edge 2325. This straight edge 2325 allows for controlled deployment of the first anterior anchor tab A1, the second anterior anchor tab A2, and the proximal anchor tab (not illustrated, if present). The ventricular anchors include tabs 2324 which engage with a slotted disc to constrain ventricular deployment. In this example, the proximal and distal capsule portions may be separated so that the first anterior anchor tab A1 deploys before the second anterior anchor tab A2 and the posterior anchor tab (not illustrated). In another example, the second anterior anchor tab A2 may be deployed before the first anterior anchor tab A1 and the posterior anchor tab (not illustrated). In yet another example, the posterior anchor tab (not illustrated) may deploy before the first anterior anchor tab A1 and second anterior anchor tab A2. In a further example, the first anterior anchor tab A1 and the second anterior anchor tab A2 deploy simultaneously before the posterior anchor tab (not illustrated). In yet another example, the first anterior anchor tab A1, the second anterior anchor tab A2, and the posterior anchor tab (not illustrated) deploy simultaneously. Other aspects of this example generally take the same form as other examples discussed in this specification such as the anchors A1 and A2, and valve 1506, 1500B. The distal capsule portion 2601 is actuated by pushing the inner shaft 2518 coupled to the distal capsule portion 2601 distally, thereby separating the distal capsule portion 2601 from the proximal capsule portion 2505. A second inner shaft (not illustrated) may be coupled to the proximal capsule portion 2505 wherein pulling the second inner shaft separates or removes the proximal capsule portion from the distal capsule portion after the ventricular deployment.

In FIG. 25E1, shows another example of a delivery system with a proximal capsule portion 2505 and a distal capsule portion 2602 where the distal capsule portion is partially separated from the prosthetic valve 1506, to remove the constraint from a portion of the prosthetic valve thereby allowing the anterior tabs A1, A2 to expand. The distal capsule portion 2602 has a proximal edge with a slanted edge 2326 relative to the longitudinal axis of the capsule. FIG. 25E2 shows the three-dimensional sketch and the two-dimensional sketch of the slanted proximal edge 2326. The slanted edge 2326 allows for the controlled deployment of the first anterior anchor tab A1, second anterior anchor tab A2, and the posterior anchor tab (not illustrated). In an example, the distal capsule portion 2602 or the proximal capsule portion 2505 may be separated in which the first anterior anchor tab A1 deploys before the second anterior anchor tab A2 and the posterior anchor tab (not illustrated). In another example, the second anterior anchor tab A2 may be deployed before the first anterior anchor tab A1 and the posterior anchor tab (not illustrated). In yet another example, the posterior anchor tab (not illustrated) may deploy before the first anterior anchor tab A1 and second anterior anchor tab A2. In a further example, the first anterior anchor tab A1 and the second anterior anchor tab A2 deploy simultaneously before the posterior anchor tab (not illustrated). In yet another example, the first anterior anchor tab A1, the second anterior anchor tab A2, and the posterior anchor tab (not illustrated) deploy simultaneously. The ventricular anchors include tabs 2324 that engage with the slotted disc to constrain deployment thereof. Other aspects of the prosthetic valve and capsule generally take the same form as previously disclosed herein. The proximal capsule may be retracted proximally away from the atrial portion of the prosthetic valve after ventricular deployment to allow the atrial portion to expand.

FIG. 25F1 shows yet another example of a delivery system with a proximal capsules portion 2505 and a distal capsule portion 2518 wherein removing the distal capsule constraint from a portion of the prosthetic valve allows the anterior tabs A1, A2 to expand while the atrial portion is constrained. The distal capsule portion 2603 has a proximal edge with an undulating or corrugated edge 2327 along the proximal edge of the distal capsule portion. FIG. 25F2 shows the three-dimensional sketch and the two-dimensional sketch of the proximal undulating or corrugated edge 2327. The undulating or corrugated edge 2327 allows for the controlled deployment of the first anterior anchor tab A1, the second anterior anchor tab A2, and the posterior anchor tab. In an example, the capsule may be separated in which the first anterior anchor tab A1 deploys before the second anterior anchor tab A2 and the posterior anchor tab (not illustrated). In another example, the second anterior anchor tab A2 may be deployed before the first anterior anchor tab A1 and the posterior anchor tab (not illustrated). In yet another example, the posterior anchor tab (not illustrated) may deploy before the first anterior anchor tab A1 and second anterior anchor tab A2. In a further example, the first anterior anchor tab A1 and the second anterior anchor tab A2 deploy simultaneously before the posterior anchor tab (not illustrated). In yet another example, the first anterior anchor tab A1, the second anterior anchor tab A2, and the posterior anchor tab (not illustrated) deploy simultaneously. The peaks and valleys of the undulations may be adjusted thereby controlling the constraint provided to the prosthesis and therefore controlling the deployment sequence. The proximal capsule may be retracted proximally to unconstrain the proximal portion of the prosthesis thereby allowing the atrial portion to self-expand after the ventricular portion.

Figure 25H:
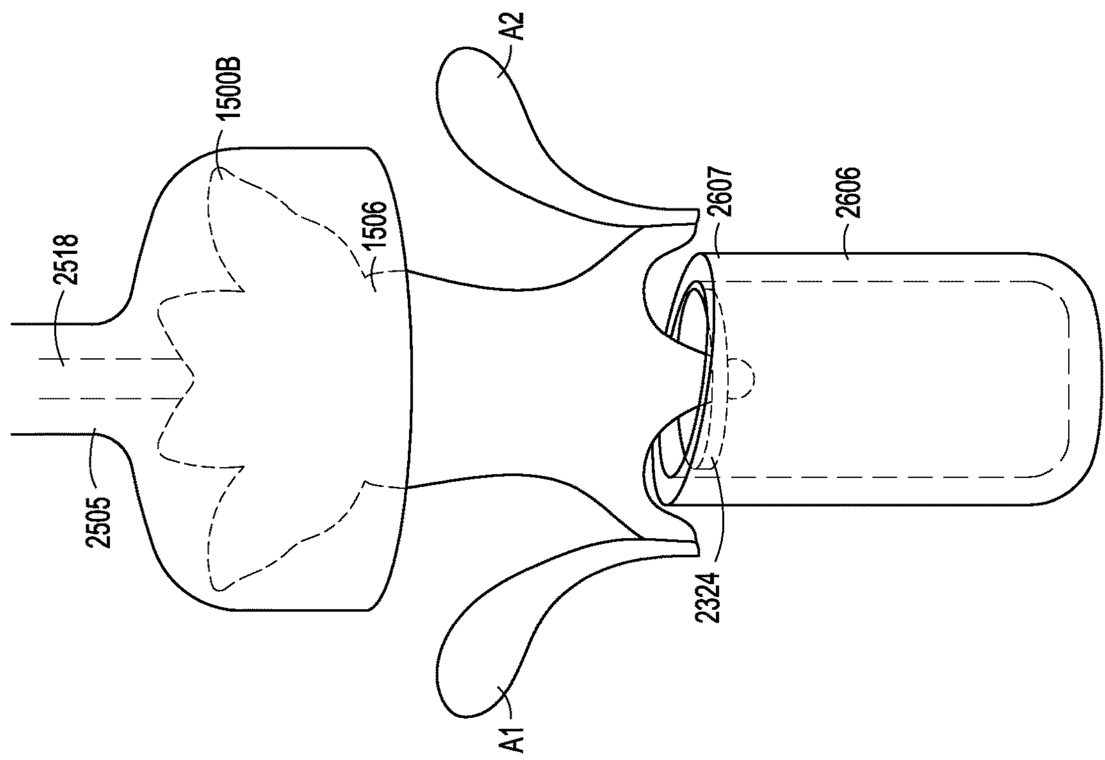
FIGS. 25G-25H show an example of ventricular deployment.
Figure 25G:
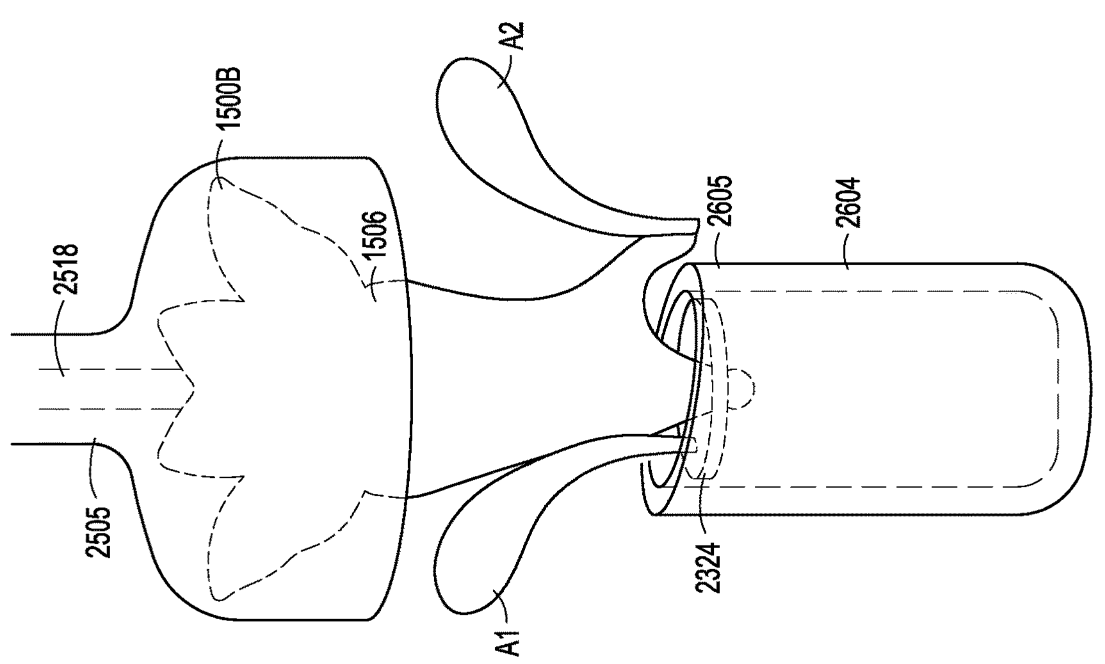

FIG. 25G shows yet another example of a delivery system with a proximal capsule portion 2505 and a distal capsule portion 2604 wherein removing the distal capsule constraint from a portion of the prosthetic valve allows the anterior tabs A1, A2 to expand while the atrial portion is constrained. In an example, the capsule may be separated in which the first anterior anchor tab A1 deploys before the second anterior anchor tab A2 and the posterior anchor tab (not illustrated). In another example, the second anterior anchor tab A2 may be deployed before the first anterior anchor tab A1 and the posterior anchor tab (not illustrated). In yet another example, the posterior anchor tab (not illustrated) may deploy before the first anterior anchor tab A1 and second anterior anchor tab A2.

FIG. 25H shows that further advancement of the distal capsules releases the second anchor tab in FIG. 25G. Here, proximal capsule portion 2505 and a distal capsule portion 2606 are separable and removing the distal capsule constraint from a portion of the prosthetic valve allows the second anterior tab to deploy while the atrial portion is still constrained. In a further example, the first anterior anchor tab A1 and the second anterior anchor tab A2 deploy simultaneously before the posterior anchor tab (not illustrated). In yet another example, the first anterior anchor tab A1, the second anterior anchor tab A2, and the posterior anchor tab (not illustrated) deploy simultaneously.

Figure 25J:
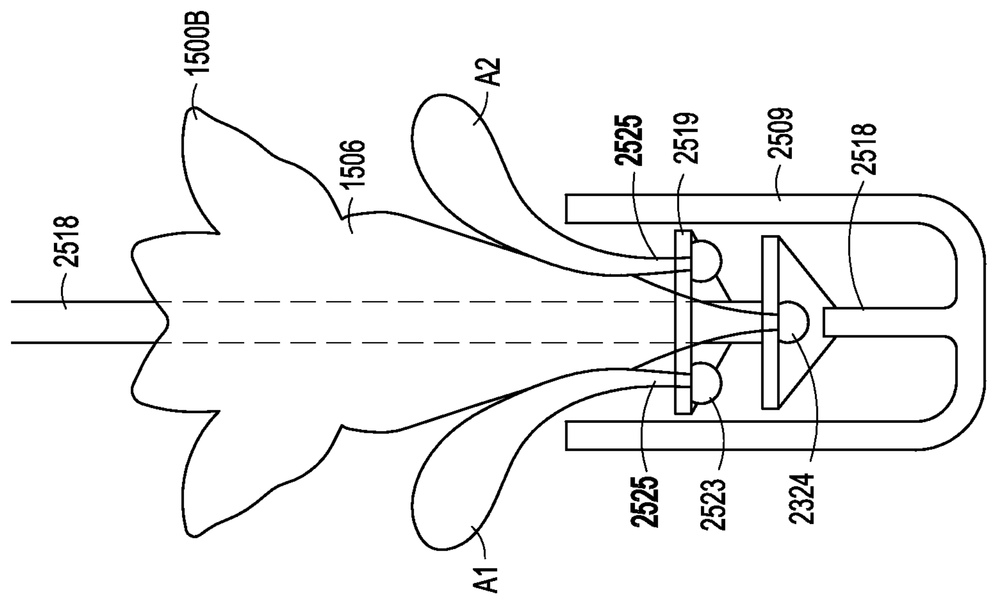
FIG. 25J illustrates an example of controlling deployment.
Figure 25I:
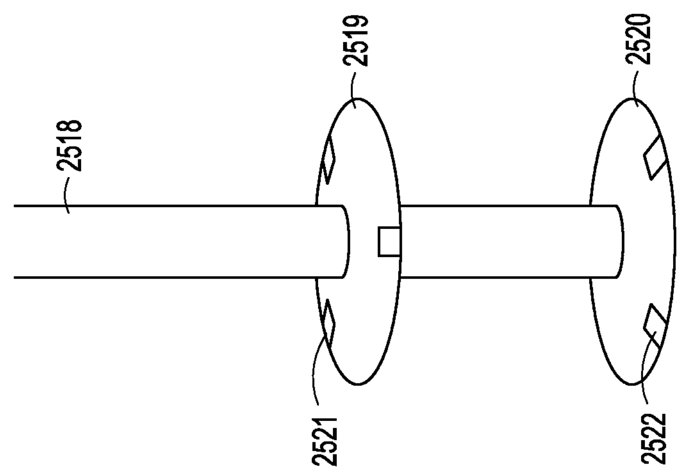
FIG. 25I shows an example of a mechanism for controlling deployment.

FIG. 25I shows part of a delivery system with an elongate shaft 2518 coupled to a disc-like commissure control element 2520 and a disc-like elbow control element 2519 adjacent a distal end thereof. Other aspects of the delivery system may take the same or similar form as other delivery systems disclosed herein. The commissure control element may have one or more commissure control slots 2522 extending radially inward or outward and the elbow control element may have one or more elbow control slots 2521 that extend radially inward or outward. The slots are sized and shaped to receive a portion of the commissure tabs or anchor tab elbows 2525 so they may be constrained in position and held until an outer sheath or capsule is retracted or the elongate shaft 2518 is advanced distally to remove the constraint and allow the commissure tabs and/or the anchor tab elbow 2525 to radially expand. Actuation of the commissure control element or the elbow control element may be controlled in any desired order in order to release the commissure tabs and the anchor tab elbows 2525 in any desired order. Thus, the commissure tabs may be released first then the elbows 2525, or the elbows 2525 first then the commissure tabs, or the commissure tabs and the elbows 2525 may be released concurrently as discussed below.

FIG. 25J further shows the delivery system and its interaction with the prosthetic valve 1506. In this example, the elbow control element 2519 comprises at least two elbow control slots wherein anterior anchor tabs A1 and A2 contain protrusions (also referred to as tabs) 2523 and 2519 respectively. The protrusions 2523 and 2519 are disposed into the slots 2521 and constrained by an outer sheath or a portion of the capsule, wherein upon release A1, or A2, or both expands. A1 may expand first, A2 may expand first, or A1 and A2 may expand simultaneously. The commissure control element 2520 also contains one or more commissure control slots 2522 wherein a commissure control protrusion 2324 may be disposed into the one or more slots. The commissure control element may release the one or more tabs before the elbow control element, or the elbow control element may release the one or more tabs before the commissure control element, or the commissure control element and elbow control element may release simultaneously. In an example, the elbow control element 2519 may be deployed in which the first anterior anchor tab A1 deploys before the second anterior anchor tab A2 and the posterior anchor tab (not illustrated) as well as before the commissure control element releasing the commissure tabs. In another example, the second anterior anchor tab A2 may be deployed before the first anterior anchor tab A1 and the posterior anchor tab (not illustrated). In yet another example, the posterior anchor tab (not illustrated) may deploy before the first anterior anchor tab A1 and second anterior anchor tab A2. In a further example, the first anterior anchor tab A1 and the second anterior anchor tab A2 deploy simultaneously before the posterior anchor tab (not illustrated. In yet another example, the first anterior anchor tab A1, the second anterior anchor tab A2, and the posterior anchor tab (not illustrated) deploy simultaneously. In yet another example, the commissure control element coupled to the inner shaft and connected to the commissure tabs can deploy the commissure tabs (not illustrated) before the first anterior anchor tab A1, second anterior anchor tab A2, and posterior anchor tab (not shown).

Other deployment sequences are also contemplated. Any permutation or combination of the above referenced sequences may be used. For example, the atrial skirt may deploy first, followed by the ventricular skirt, then any or all of the anchor tabs in any sequence. In another example, the ventricular skirt may deploy first, followed by the atrial skirt then the anchor tabs in any sequence. In still another example, the anchor tabs may deploy in any sequence followed by the ventricular skirt then the atrial skirt. In yet another example, the ventricular skirt may be deploy first followed by the anchor tabs in any sequence then followed by the atrial skirt.

Trans-Septal Delivery System

Figure 26:
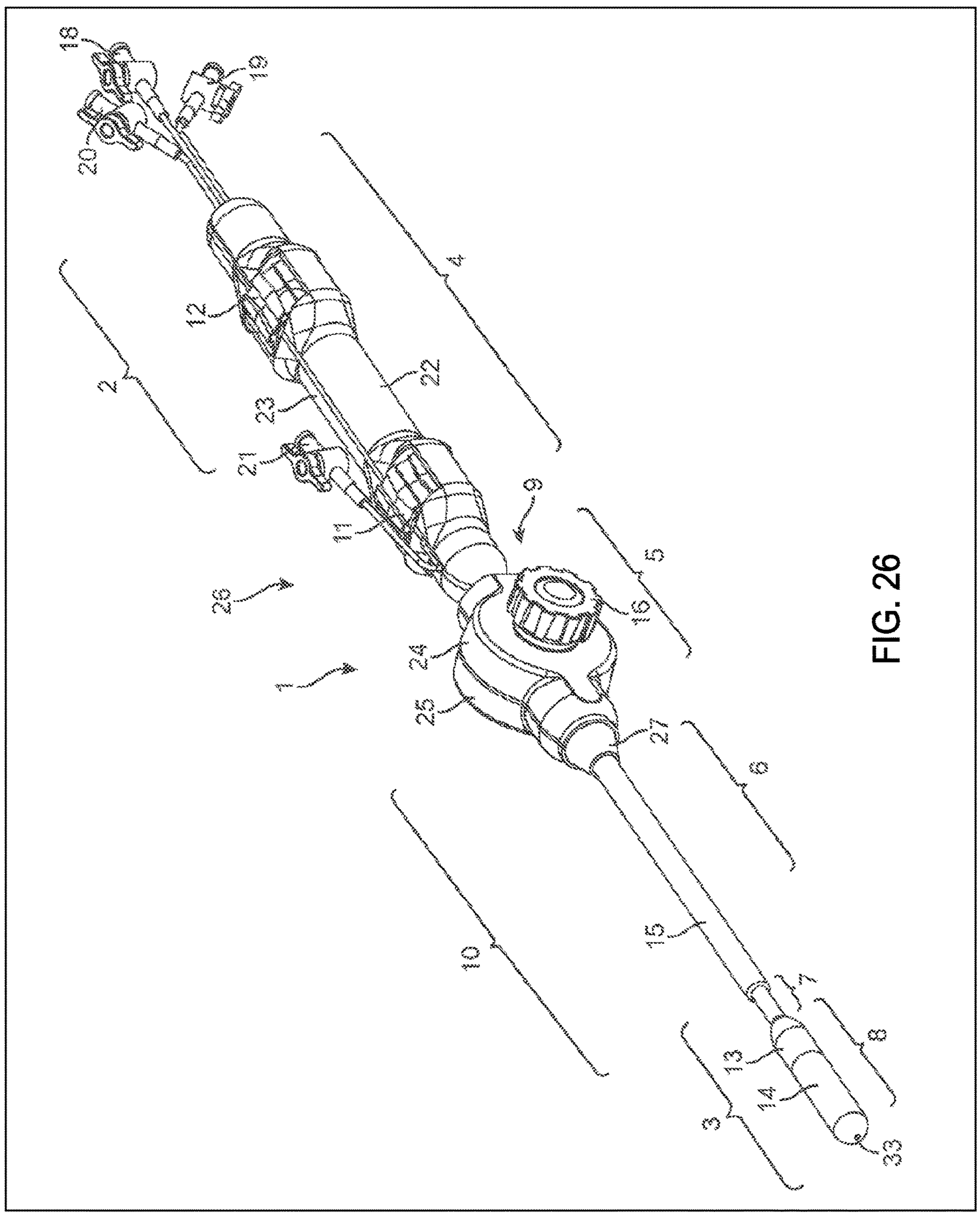
FIG. 26 is a perspective view of a transseptal delivery system for a prosthetic heart valve.

Referring initially to FIG. 26, one example of a trans-septal delivery system for trans-catheter heart valve delivery is depicted generally as 1. In the drawings and in the descriptions which follow, the term "proximal" will refer to the end 2 of the delivery system that is closest to the user, while the term "distal will refer to the end 3 that is farthest from the user. The trans-septal delivery system 1 can comprise a prosthesis such as a prosthesis capsule or valve capsule assembly 8, a delivery catheter assembly 7, a steering guide 10, a delivery handle assembly 4, and an interface 9 between the delivery handle 4 and steering handle 5. The steering guide 10 can be comprised of a steerable catheter assembly 6 and a steering handle 5. The valve capsule assembly 8 can be in operable communication with the delivery handle assembly 4 by way of the delivery catheter assembly 7 which extends therebetween. The translational position and angular attitude of the prosthesis or valve capsule assembly 8 can be operably controlled by the steering handle 5 and in communication by way of the steerable catheter assembly 6 which extends therebetween. The interface 9 can be comprised of a slidable seal, such as an O-ring type seal. The interface 9 can further function to allow the delivery handle or delivery catheter to translate within the steering handle while maintaining some Stiction, thus preventing blood or other fluid from seeping out of the steering handle should such blood or fluid make its way up the steering catheter assembly.

Further details of a trans-catheter mitral valve or any prosthesis that may be used with any of the delivery devices described herein, along with other related delivery catheters are described in U.S. Pat. No. 8,579,964 to Lane et. al.; the entire contents of which are incorporated by reference herein.

Generally, delivery handle assembly 4 includes a distal actuator such as a thumb wheel 11 and a proximal actuator such as a thumb wheel 12, both of which are integrally associated with the delivery handle assembly 4, which is comprised of an A-side delivery handle housing 22 and a B-side delivery handle housing 23. Distal thumbwheel 11 and proximal thumb wheel 12 are also rotatably positionable with respect to the delivery handle assembly 4, serving as actuators by way of internal threads (not shown) and enabling translational control of various catheters within the delivery catheter assembly 7, further evidence of which will be detailed in a later section. The delivery handle assembly 4 is operatively coupled to the valve capsule assembly 8 via the delivery catheter assembly 7, which functions in one aspect as a motion translation agent. In some embodiments, the delivery handle assembly 4, delivery catheter assembly 7 and valve capsule assembly 8 can form a delivery system 26. In some embodiments, the steering handle 5 and steer able catheter assembly 7 can form a steering guide 10, which provides a path through which the delivery system 26 can translate and rotate, and from which it may take its shape in order to traverse tortuous vasculature during implantation. Taken altogether, the delivery system 26 and steering guide 10 can form the trans-septal delivery system 1.

Valve capsule assembly 8 may exhibit various constructions. For example, the distal capsule 14 and proximal capsule 13 may be formed from substantially rigid, stainless steel, polymer, metal or otherwise rigid tubing, from collapsible, flexible tubing, or from shape-settable exotic metal alloys which exhibit shape memory characteristics and are actuated by temperature gradients inherent to the human physiology, such as nitinol. Presently, portions of the valve capsule assembly 8 can be translatably controlled by the turning of either the distal thumbwheel 11, or the proximal thumbwheel 12, located in the delivery handle assembly 4. By rotating the distal thumbwheel 11, the proximal capsule 14 can be translatably positioned along the axis of the capsule assembly 8 in order to reveal certain portions of the prosthesis such as a prosthetic mitral valve for example. By rotating the proximal thumb wheel 12, the proximal capsule 13 can be translatably positioned along the axis of the valve capsule assembly 8, again preferably revealing and releasing certain portions of the prosthetic valve (not shown). Capsule variations will be described in detail in a later section. Any capsule examples may be used with any of the deployment sequences disclosed previously.

Figure 31:
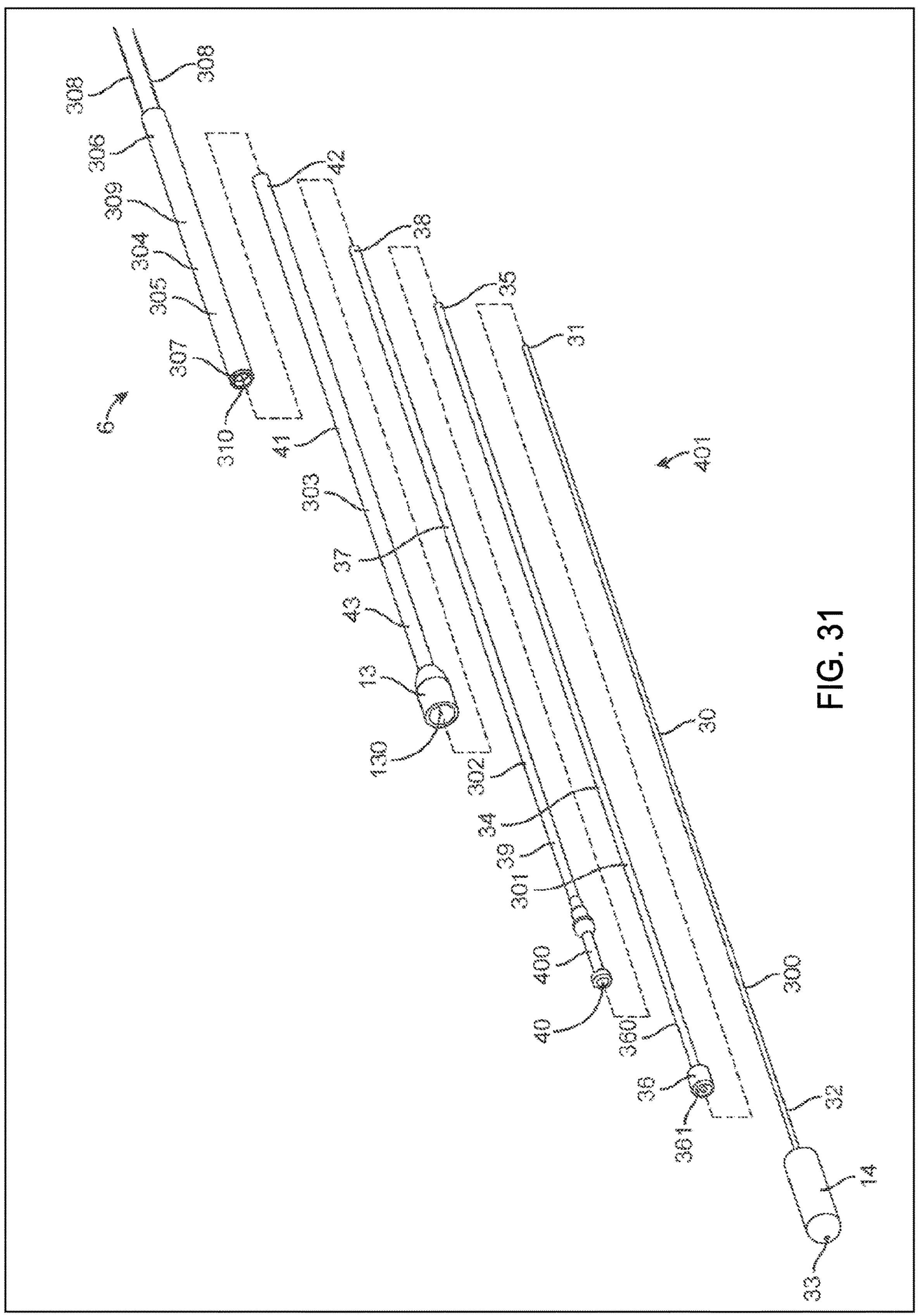
FIG. 31 is an assembly view of the delivery catheter portion of the delivery system seen in FIG. 26.

With reference to FIG. 31, the delivery catheter assembly 7 is generally comprised of a family of nested catheters concentrically and slidably disposed over one another. The innermost catheter in the family of nested catheters is the guidewire catheter 30 which has a distal section 32 that is coupled to the distal capsule 14, and a proximal section 31, with a guidewire lumen 33 that is generally sized to accept a guidewire running therebetween. The guidewire catheter 30 has a constant outer diameter and a constant inner diameter throughout its entire length, as well as a flexible section 300 which allows for articulation. The guidewire catheter 30 is generally configured to be able to fit inside of and translate slidably with respect to the bell catheter 34. The bell catheter 34 has a distal section 360 that is coupled to a bell 36, wherein the bell can be generally cylindrically shaped having a diameter larger than the bell catheter, and a proximal section 35, with an inner lumen 361 that is generally sized to accept the guidewire catheter 30 running therebetween. The bell catheter 34 has a constant outer diameter and a constant inner diameter throughout its entire length, as well as a flexible section 301 which allows for articulation. The bell catheter 34 is generally configured to be able to fit inside of and slidably translate with respect to the anchoring catheter 37. The anchoring catheter 37 has a distal section 39 that is coupled to an anchor 400, wherein the anchor can be generally cylindrically shaped and have a plurality of anchoring slots circumferentially positioned to receive valve commissure anchoring portions (not shown), and a proximal section 38, with an inner lumen 40 that is generally sized to accept the bell catheter 34 running therebetween. The anchoring catheter 37 has a constant outer diameter and a constant inner diameter throughout its entire length, as well as a flexible section 302 which allows for articulation. The anchoring catheter 37 is generally configured to be able to fit inside of and translate with respect to the sheath catheter 41. The sheath catheter 41 has a distal section 43 that is coupled to the proximal capsule 13, wherein the proximal capsule can have a cylindrical portion terminating in a cap portion, and wherein the cap portion can have a rounded dome-like Surface, and a proximal section 42, with an inner lumen 130 that is generally sized to accept the anchoring catheter 37 running therebetween. The sheath catheter 41 has a constant outer diameter and a constant inner diameter throughout its entire length, as well as a flexible section 303 which allows for articulation. The sheath catheter 41 is generally configured to be able to fit inside of and slidably translate with respect to the steering catheter assembly 6. The steering catheter assembly 6 is comprised of a steerable catheter 309, a pull ring 307, wherein the pull ring can have a circular ring-like shape located at the distal section 305 of the catheter, a plurality of pull wires 308 located at the proximal section of the catheter, a flexible section 304 that allows for articulation, and an inner lumen 310 running throughout the entire length. For each pull wire 308 there is a corresponding lumen (not shown) that runs the entirety of the steerable catheter 309.

Generally, the steering guide 10 includes an interface section 9 that is comprised of an O-ring type interface of cylindrical shape similar to a gasket, which is embedded within A and B side steering handle housings 24 and 25 respectively, the A-side steering handle housing 24, the B-side steering handle housing 25, an actuator such as a steering thumbwheel 16, wherein the steering thumb wheel can have a generally cylindrical shape, a catheter strain relief 27, and a steerable catheter assembly 6. The steering thumbwheel can additionally include one or more protrusions separated by one or more recesses or slots to provide a surface to facilitate grasping and turning the wheel. In some examples, the steering thumbwheel can have a textured surface with ribs to facilitate grasping and turning the wheel. The interface section 9 provides a dynamic seal between the steering handle 5 and the delivery catheter assembly 7 thus allowing for slidably sealed catheter translation thereby; the delivery catheter assembly thus may traverse therethrough and exit towards the distal end of the steering guide 10 at the terminal, articulated end 15 of the steerable catheter assembly 6. While the interface section 9 provides a dynamic seal, the delivery catheter assembly 7 may still translate and rotate within the steering guide 10, in order to define accurate positioning within a patient, at the target implant site. Detail regarding the implant procedure and target implant site will be discussed in a later section. In order to actuate the steerable portion of the steering catheter assembly 6, the steering thumbwheel 16 is turned. When the steering thumbwheel 16 is turned, the articulated end 15 of the steerable catheter assembly 6 will bend in the same direction as the direction of thumbwheel turning. This motion translation is achieved through the use of internal pull wires 308, as depicted for example in FIG. 31, that are distally in mated connection (such as a welded connection, or using fasteners, or adhesives, or any suitable method of fastening) with a pull ring 307, and proximally connectably communicate with the internal mechanisms which are inherent to the steering handle 5 and will be described in further detail in a later section.

Figure 27A:
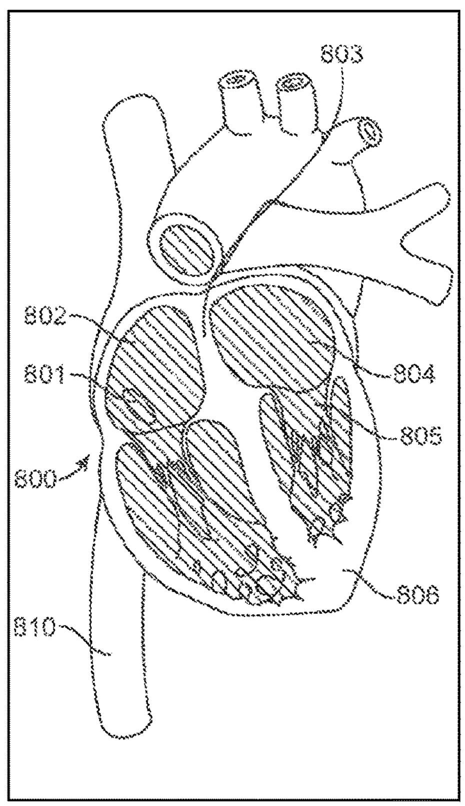
FIGS. 27A-27D illustrate an example of a transseptal method of delivering a prosthetic valve.
Figure 27B:
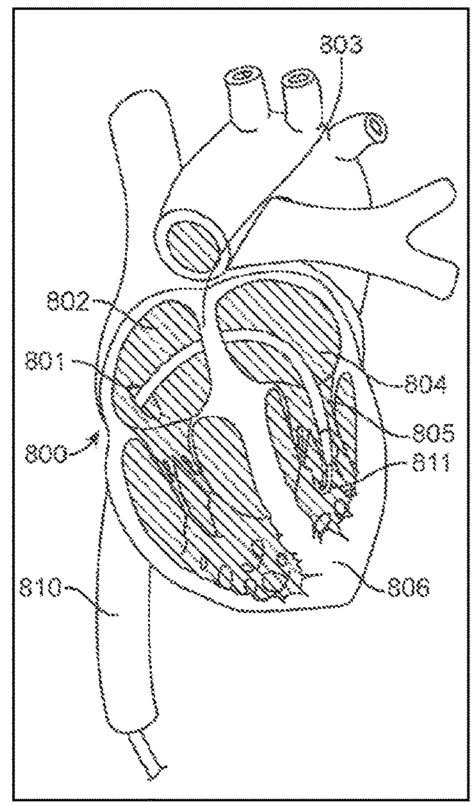
Figure 27C:
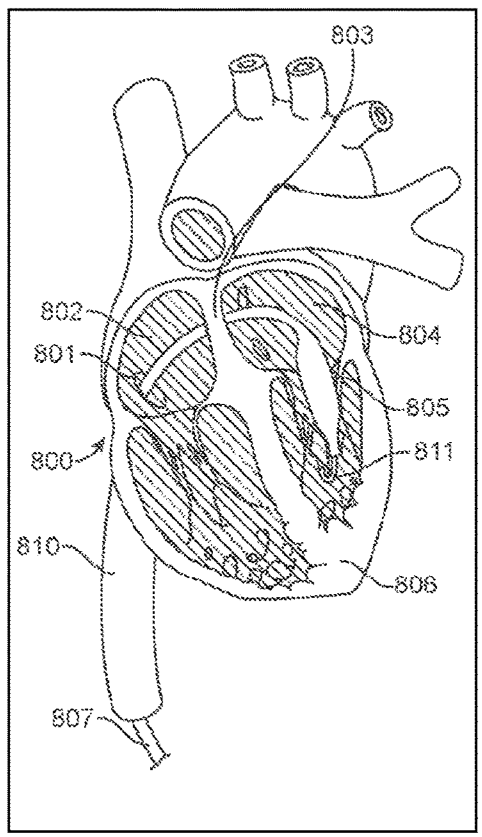
Figure 27D:
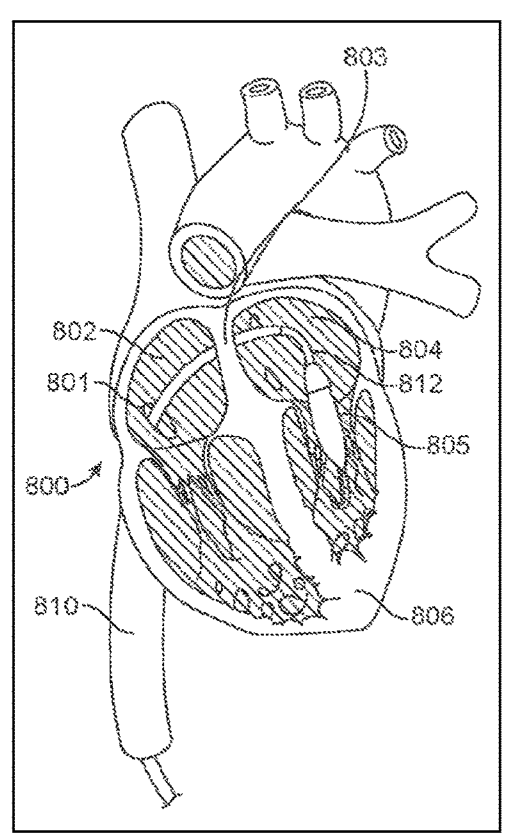

FIG. 27A describes a general depiction of a partial view (with anterior ventricular surface, pulmonary trunk, and aorta removed) of a human heart. The steering guide 7 will follow a guidewire 811 that has previously been placed in order to provide a path that leads to the target implant site. During a typical procedure, the steering guide 7 will enter the inferior vena cava 810 by way of the descending inferior vena cava (not shown) and first an incision at the femoral vein near the groin (not shown). The steering guide 7 will then exit the inferior vena cava 810 through a caval foramen 801 which acts as an inlet to the right atrium 802 (FIG. 27B). Once in the right atrium 802, the steering guide 10 will then penetrate the foramen ovale 803 in the septal wall and gain access to the left atrium 804. At the left atrium 804 (FIG. 27C), the steering guide 10 will be aimed towards the mitral annulus 805 in order to provide a direct channel towards the implant site (mitral annulus 805) for the delivery catheter 812 (FIG. 27D) to operate within.

Figure 28:
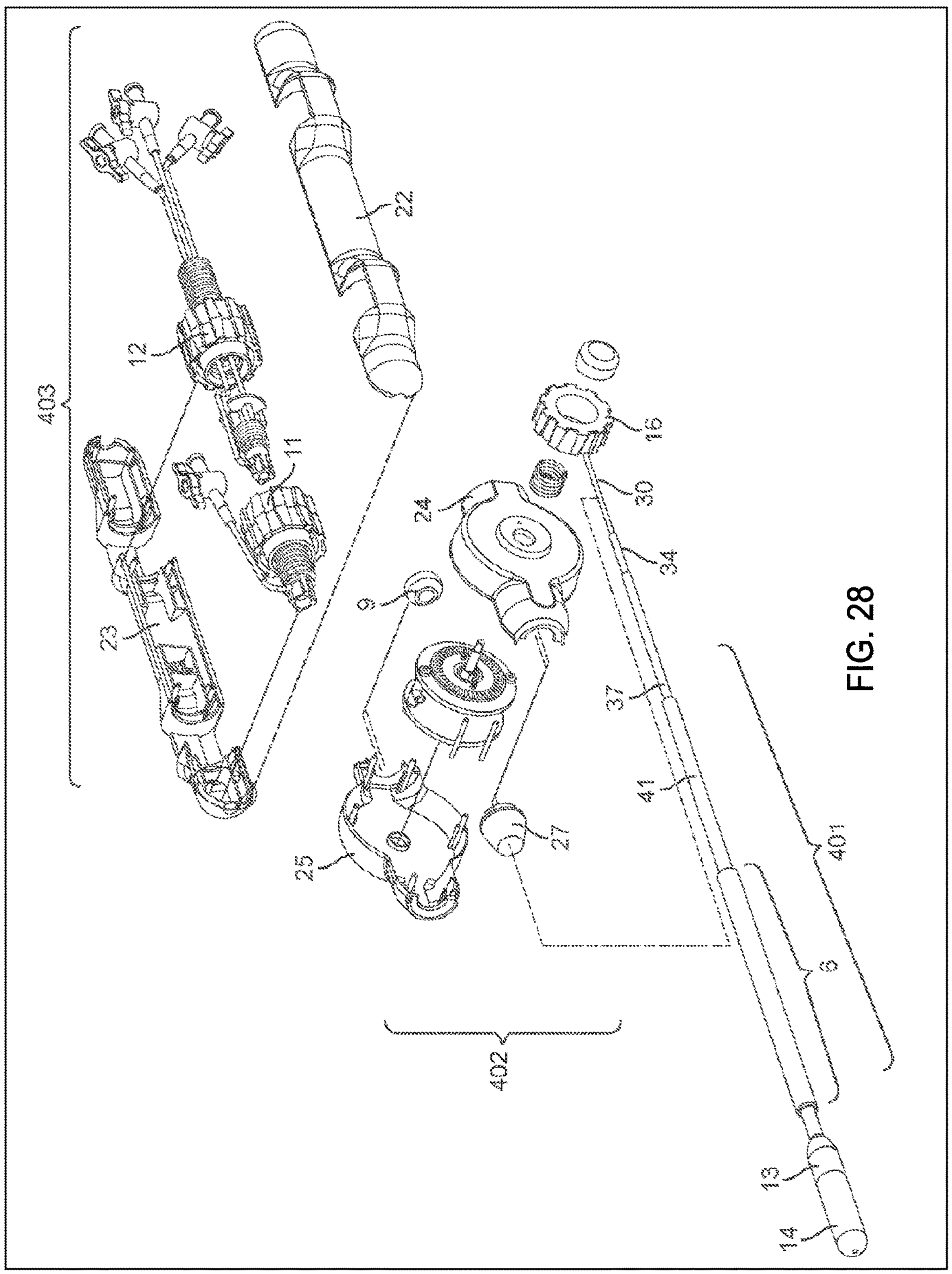
FIG. 28 is an assembly view of the delivery system seen in FIG. 26.

With particular reference to FIGS. 28-31, the internal mechanisms of the trans-septal delivery system 1 that permit functionality will be described. Specifically, FIG. 28 illustrates an example of an assembly of a trans-septal delivery system 1 shown in exploded view. The trans-septal delivery system 1 is displayed in sections in order to make description of the internal parts more easily understood. Delivery handle section 403 will be described in further detail below with reference to FIG. 29. Steering handle section 402 will be described in further detail below with reference to FIG. 30. Finally, delivery catheter section 401 has previously been described above with reference to FIG. 31.

Figure 29:
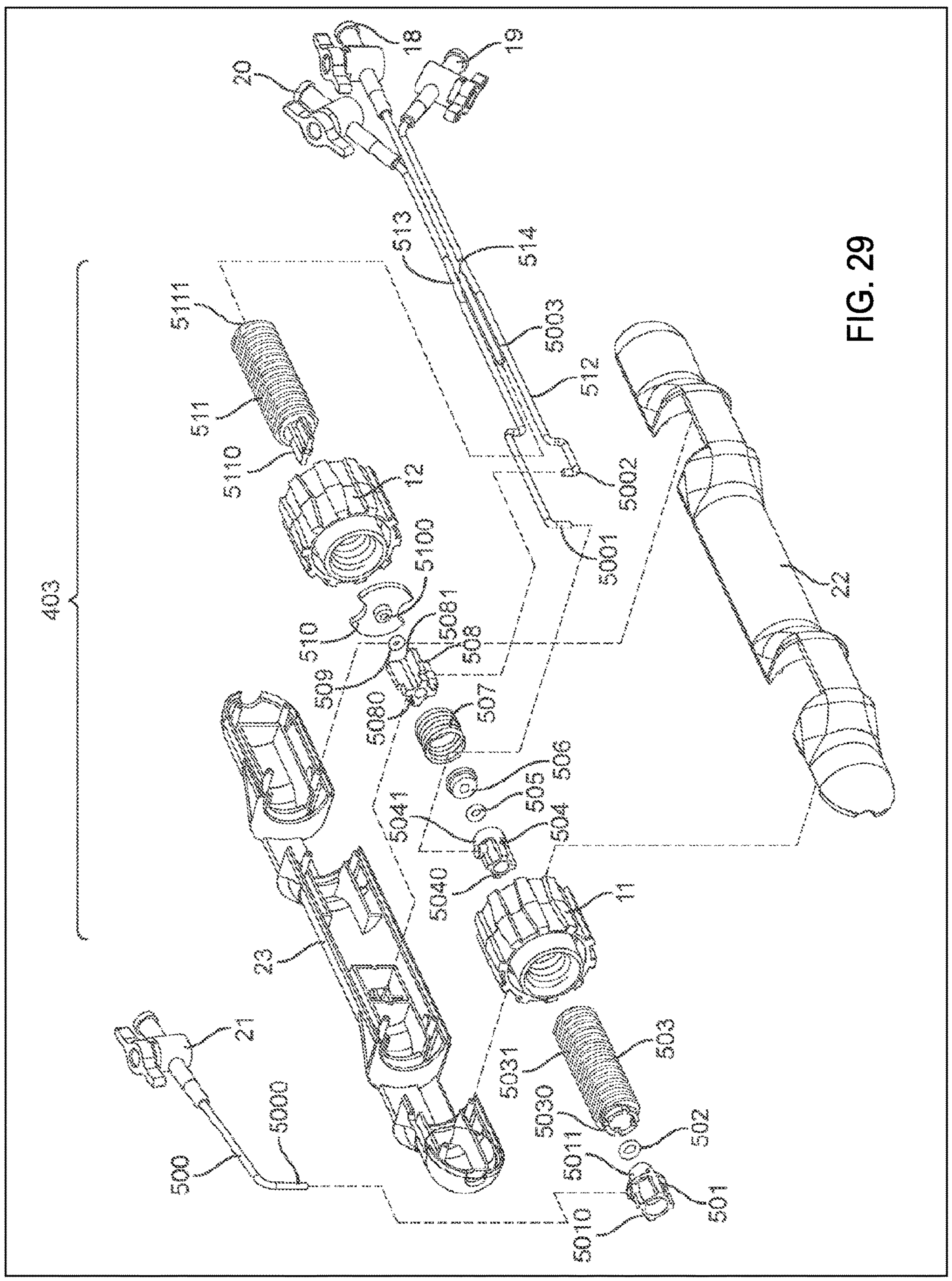
FIG. 29 is an assembly view of the delivery handle portion of the delivery system seen in FIG. 26.

Referring now to FIG. 29, the delivery handle section 403 is generally comprised of an A-side delivery handle housing 22 that is in mating connection with a B-side delivery handle housing 23, actuators such as a plurality of thumbwheels (distal thumb wheel 11 and proximal thumb wheel 12), a plurality of force transferring leadscrews (distal leadscrew 503 and proximal leadscrew 511) that may trans late proximally or distally depending on the rotation of the thumbwheel within said plurality of thumbwheels, a plurality of hemostatic ports and related tubing which provide the ability to remove entrained air boluses from concentrically nested catheters within the system, and various other components and fasteners that shall be described in further detail. Referring specifically to the motion transferring elements of the delivery handle section 403, a distal leadscrew 503 is in threaded connection with a distal thumbwheel 11 and by turning said distal thumbwheel 11, translational motion is imparted upon the distal leadscrew 503. The motion of the distal leadscrew 503 is transferred to the sheath catheter 41 by way of a connection between the proximal end 42 of the sheath catheter 41 and the distal end 5010 of the distal leadscrew cap 501, which itself is mated with adhesive (medical grade UV cure adhesive, or medical grade cyanoacrylate adhesive, or any suitable medical grade adhesive for plastics or polymers, etc.) to the distal lead screw 503. The distal leadscrew cap 501 also permits the ejection of air by way of a sealed interface (distal O-ring 502) between the sheath catheter 41 and the anchoring catheter 37. A stationary screw cap 504 is entrained within the A and B side handle housings 22, 23 respectively, and provides location and retention for the anchoring catheter 37, whereby the proximal end 38 of the anchoring catheter 37 is in mated connection (medical grade UV cure adhesive, or medical grade cyanoacrylate adhesive, or any suitable medical grade adhesive for plastics or polymers, or by way of fastening mechanical threads) with the distal end 5040 of the stationary screw cap 504. The stationary screw cap 504 also permits the ejection of air by way of a sealed interface (medial O-ring 505) between the anchoring catheter 37 and the bell catheter 34. A proximal leadscrew 511 is in threaded connection with a proximal thumb wheel 12 and by turning said proximal thumb wheel 12, translational motion is imparted upon the proximal leadscrew 511. The motion of the proximal leadscrew 511 is transferred to the guidewire catheter 30 by way of a connection between the proximal end 31 of the guidewire catheter 30 and the distal end 5110 of the proximal leadscrew 511. Proximal leadscrew 511 motion is also transferred to the bell catheter 34 by way of a slidable interference between the distal end 5110 of the proximal leadscrew 511 and the proximal leadscrew plate 510, whereby the proximal leadscrew plate 510 is in mated connection with the proximal leadscrew cap 508, and the proximal leadscrew cap 508 houses the proximal end 35 of the bell catheter 34. The proximal leadscrew cap 508 also permits the ejection of air by way of a sealed interface (proximal O-ring 509) between the bell catheter 34 and the guidewire catheter 30. The proximal leadscrew 511 permits the ejection of air by way of an which is in mated connection with the proximal leadscrew 511.

Figure 30:
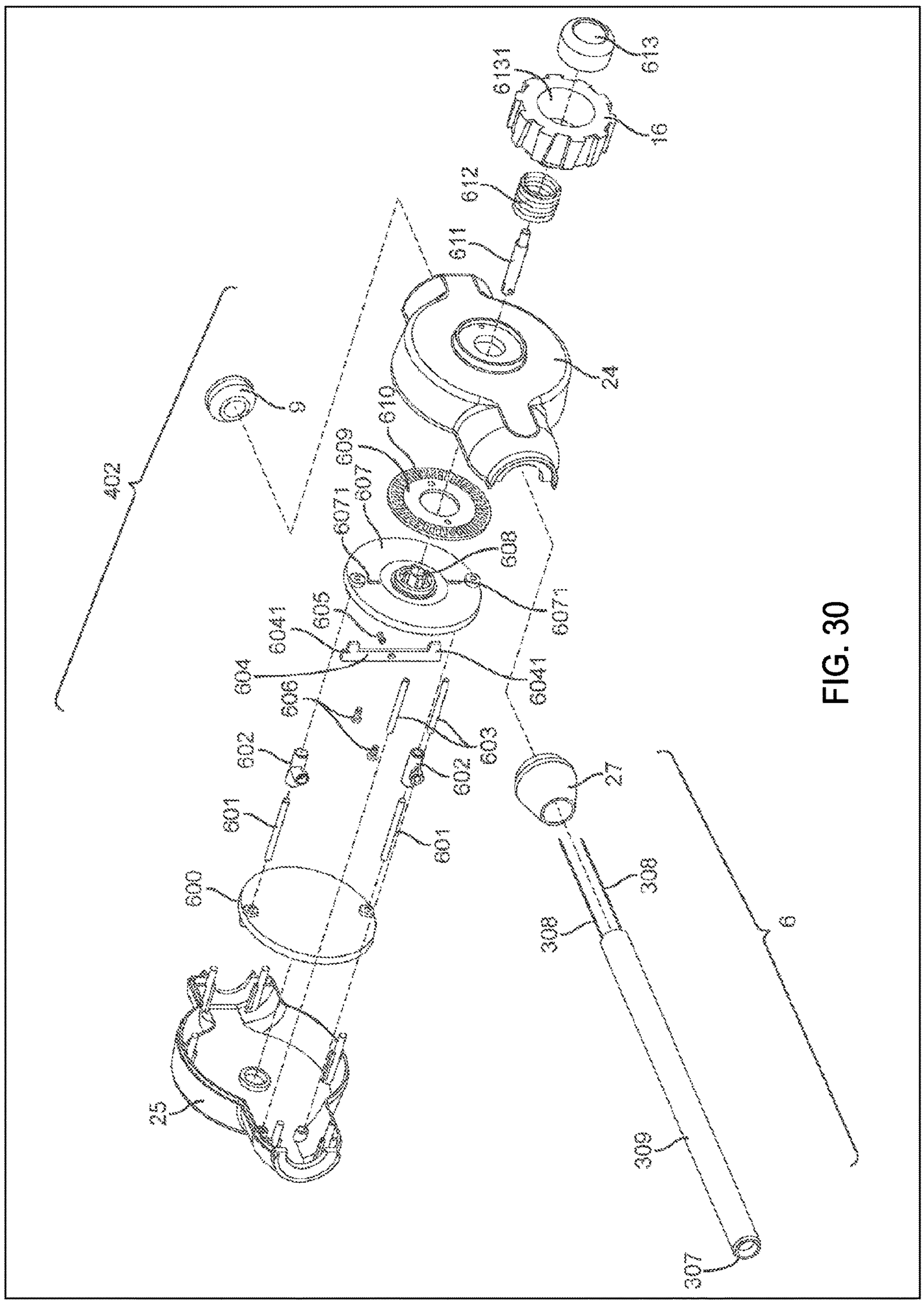
FIG. 30 is an assembly view of the steering guide portion of the delivery system seen in FIG. 26.

Referring now to FIG. 30, the steering handle section 402 is generally comprised of an A-side steering handle housing 24 that is in mating connection with a B-side steering handle housing 25, a steerable catheter assembly 6 that is in mating connection with a catheter strain relief 27, an interface 9, a plurality of rotatable disks (B-side rotatable disk 600 and A-side rotatable disk 607), a steering thumb wheel 16, a push button 613, and various other components and fasteners that shall be described in further detail. Refer ring specifically to the steering elements of the steering handle section 402, a steering thumbwheel 16 is in mating connection with a locking hub 608 that is centered within the A-side rotatable disk 607. The A-side rotatable disk 607 and B-side rotatable disk 600 are coupled together by way of a plurality of carrier rods 601, and work mechanically to spin within the handle housing that is comprised of the A-side steering handle housing 24 and B-side steering handle housing 25. Since the A-side rotatable disk 607 is connected to the steering thumbwheel 16, rotation of the steering thumb wheel 16 causes rotation of the A-side rotatable disk 607. A specific function of the plurality of rotatable disks (B-side rotatable disk 600 and A-side rotatable disk 607) is to actuate the plurality of pull wires 308 by way of tensioning hinges 602 that may spin freely on the carrier rods 601 and that are also connected to the pull wires 308 and also apply tension to them when turned. Referring now specifically to the locking elements of the steering handle section 402, a push button 613 is in threaded connection with a push button pin 611 that acts as a shaft. The push button 613 is located within a cavity 6131 that allows for direct translation when the button is depressed. A push button spring 612 is housed between the inside surface of the push button 613, and the bottom of the cavity 6131 and provides return force for when the depressed push button 613 is released. Motion from the pushbutton 613 is transferred along the pushbutton pin 611 directly to a cross bar 604 that is fastened to the push button pin 611 by way of a setscrew 605. When the push button pin 611 translates as the pushbutton 613 is depressed, the cross bar 604 also translates and a plurality of cross bar pegs 6041 that are located on the ends of the cross bar 604 thus translate as well. When in an un-depressed state, the cross bar pegs 6041 are seated within a plurality of slots 6071 that appear on the periphery of the A-side rotatable disk 607. The cross bar pegs 6041 then also project through the slots 6071 and may rest within any of the circumferential slits 610 that appear in an array about the periphery of a position disk 609 that is mounted to the inside surface of the A-side steering handle housing 24 by threaded fasteners 606. When in a depressed state, the cross bar pegs 6041 are moved away from the circumferential slits 610 until clearance is achieved, and the locking mechanism enables free rotation of the cross bar 604, as well as all aspects that are directly connected to the A-side rotatable disk 607.

While various forms of the present invention have been shown and described herein, it will be obvious to those skilled in the art that such forms are provided by way of tangibility only. Numerous variations, changes, and substitutions will now occur to those skilled in the art without departing from the invention. It should be understood that various alternatives to the examples of the invention described herein may be employed in practicing the invention. It is intended that the following claims define the scope of the invention and that methods and structures within the scope of these claims and their equivalents be covered thereby.

NOTES AND EXAMPLES

The following, non-limiting examples, detail certain aspects of the present subject matter to solve the challenges and provide the benefits discussed herein, among others.

Example 1 is a method of delivering a prosthetic valve to a native mitral valve of patient's heart, the native mitral valve having a native anterior leaflet and a native posterior leaflet, the method comprising: providing a prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange; radially expanding the ventricular portion first; and radially expanding the atrial portion after the ventricular portion.

Example 2 is the method of Example 1, wherein radially expanding the ventricular portion comprises deploying the anterior anchoring tab before deploying the posterior anchoring tab and before the ventricular skirt.

Example 3 is the method of any of Examples 1-2, wherein radially expanding the ventricular portion comprises deploying the posterior anchoring tab before deploying the anterior anchoring tab and before the ventricular skirt.

Example 4 is the method of any of Examples 1-3, wherein radially expanding the ventricular portion comprises deploying the ventricular skirt before deploying the anterior anchoring tab and before the posterior anchoring tab.

Example 5 is a prosthetic valve comprising: a ventricular portion comprising a ventricular skirt, an anterior anchoring tab disposed on the ventricular skirt, and a posterior anchoring tab disposed on the ventricular skirt; and an atrial portion comprising an atrial flange, wherein the ventricular portion is configured to radially expand first, and wherein the atrial portion is configured to radially expand after the ventricular portion.

Example 6 is the prosthetic valve of Example 5, wherein the radial expansion of the ventricular portion deploys the anterior anchoring tab before the posterior anchoring tab and the ventricular skirt.

Example 7 is the prosthetic valve of any of Examples 5-6, wherein the radial expansion of the ventricular portion deploys the posterior anchoring tab before the anterior anchoring tab and the ventricular skirt.

Example 8 is the prosthetic valve of any of Examples 5-7, wherein the radial expansion of the ventricular portion deploys the ventricular skirt before the anterior anchoring tab and the posterior anchoring tab.

Example 9 is a method of delivering a prosthetic valve to a native mitral valve of patient's heart, the native mitral valve having a native anterior leaflet and a native posterior leaflet, the method comprising: providing the prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange; providing a delivery system wherein the prosthetic valve is coupled to a distal portion of the delivery system; actuating the distal portion of the delivery system thereby removing a constraint from the prosthetic valve; radially expanding the ventricular portion first; and radially expanding the atrial portion after the ventricular portion.

Example 10 is the method of Example 9, wherein the distal portion of the delivery system further comprises a capsule comprising a distal capsule portion and a proximal capsule portion, and wherein actuating the distal portion of the delivery system comprises moving the proximal capsule portion away from the distal capsule portion.

Example 11 is the method of any of Examples 9-10, wherein the delivery system further comprises an elongate shaft coupled to the distal capsule, and wherein moving the elongate shaft distally moves the distal capsule portion thereby unconstraining the ventricular portion.

Example 12 is the method of any of Examples 9-11, wherein the distal capsule portion further comprises a straight edge along a proximal edge of the distal capsule portion, and wherein moving the distal portion of the capsule deploys the anterior anchoring tab and posterior anchoring tab simultaneously.

Example 13 is the method of any of Examples 9-12, wherein the distal capsule portion further comprises an elongate shaft, wherein the elongate shaft has a longitudinal axis, and wherein a proximal edge of the distal capsule portion is transverse to the longitudinal axis, wherein moving the distal portion of the capsule deploys the anterior anchoring tab before the posterior anchoring tab, or wherein moving the distal portion of the capsule deploys the posterior anchoring tab before the anterior anchoring tab.

Example 14 is the method of any of Examples 9-13, wherein the distal capsule portion further comprises an undulating or corrugated edge along a proximal edge of the distal capsule portion, wherein moving the distal portion of the capsule deploys the anterior anchoring tab before the ventricular skirt and the posterior anchoring tab, or wherein moving the distal portion of the capsule deploys the posterior anchoring tab before the ventricular skirt and the anterior anchoring tab.

Example 15 is the method of any of Examples 9-14, wherein the distal portion of the delivery system further comprises a slot, wherein the slot is axially oriented, and wherein actuating the distal portion of the delivery system disposes a portion of the ventricular portion into the slot thereby removing a constraint therefrom and allowing radial expansion thereof.

Example 16 is the method of any of Examples 9-15, wherein the anterior anchoring tab and posterior anchoring tab each comprise at least one elbow, wherein the prosthetic valve further comprises at least one commissure tab, and wherein the distal portion of the delivery system further comprises a capsule and an elongate shaft, the capsule comprising a distal capsule portion and a proximal capsule portion and, the elongate shaft comprising a commissure control element and an elbow control element, wherein the commissure control element and elbow control element are disposed inside the capsule, wherein the at least one elbow is coupled to the elbow control element, and the at least one commissure tab is coupled to the commissure control element, and wherein actuating the distal portion of the delivery system comprises moving the proximal portion of the capsule away from the distal portion of the capsule, thereby unconstraining the commissure control element and the elbow control element.

Example 17 is the method of any of Examples 9-16, wherein actuating the distal portion of the delivery system comprises deploying the at least one commissure tab, wherein separating the commissure tab from the commissure control element allows radial expansion thereof.

Example 18 is the method of any of Examples 9-17, wherein actuating the distal portion of the delivery system comprises releasing the at least one elbow from the elbow control element and releasing the at least one commissure tab from the commissure control element simultaneously.

Example 19 is the method of any of Examples 9-18, wherein actuating the distal portion of the delivery system comprises releasing the at least one elbow from the elbow control element before releasing the at least one commissure tab from the commissure control element, or releasing the at least one commissure tab from the commissure control element before releasing the at least one elbow from the elbow control element.

Example 20 is the method of any of Examples 9-19, wherein the commissure control element further comprises slots, or wherein the elbow control element further comprises slots, and wherein the distal portion of the ventricular portion comprises protrusions disposed in the slots, wherein actuating the distal portion of the delivery system comprises separating the protrusions from the commissure control element or the elbow control element, and wherein the separation allows the ventricular portion to expand.

Example 21 is a system for delivering a prosthetic valve to a native mitral valve of patient's heart, the native mitral valve having a native anterior leaflet and a native posterior leaflet, the system comprising: a prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange; and a delivery system wherein the prosthetic valve is coupled to a distal portion of the delivery system, wherein actuation of the distal portion of the delivery system unconstrains the prosthetic valve, to allow radial expansion of the ventricular portion first, and radial expansion of the atrial portion after the ventricular portion.

Example 22 is the system of Example 21, wherein the distal portion of the delivery system further comprises a capsule comprising a distal capsule portion and a proximal capsule portion, and wherein actuation of the distal portion of the delivery system is configured to move the proximal capsule portion away from the distal capsule portion.

Example 23 is the system of any of Examples 21-22, wherein the delivery system further comprises an elongate shaft coupled to the distal capsule portion, and wherein the distal movement of the elongate shaft moves the distal capsule portion relative to the proximal capsule portion, and wherein the distal movement of the distal capsule portion is configured to unconstrain the ventricular portion.

Example 24 is the system of any of Examples 21-23, wherein the distal capsule portion further comprises a straight edge along a proximal edge of the distal capsule portion, wherein movement of the distal portion of the capsule is configured to deploy the anterior anchoring tab and posterior anchoring tab simultaneously.

Example 25 is the system of any of Examples 21-24, wherein the distal portion of the capsule further comprises an elongate shaft, wherein the elongate shaft has a longitudinal axis, wherein movement of the distal portion of the capsule is configured to deploy the anterior anchoring tab before the posterior anchoring tab, or wherein the movement of the distal portion of the capsule is configured to deploy the posterior anchoring tab before the anterior anchoring tab.

Example 26 is the system of any of Examples 21-25, wherein the distal capsule portion further comprises an undulating or corrugated edge along the proximal edge of the distal capsule portion, wherein the movement of the distal portion of the capsule is configured to deploy the anterior anchoring tab before the ventricular skirt and the posterior anchoring tab, or wherein the movement of the distal capsule portion is configured to deploy the posterior anchoring tab before the ventricular skirt and the posterior anchoring tab.

Example 27 is the system of any of Examples 21-26, wherein the distal portion of the delivery system further comprises a slot, wherein the slot is axially oriented, and wherein the actuation of the distal portion of the delivery system is configured to dispose a portion of the ventricular portion into the slot thereby removing a constraint therefrom and allowing radial expansion thereof.

Example 28 is the system of any of Examples 21-27, wherein the anterior anchoring tab and posterior anchoring tab each comprise at least one elbow, wherein the prosthetic valve further comprises at least one commissure tab, the distal portion of the delivery system further comprises a capsule and an elongate shaft, the capsule comprising a distal portion and a proximal portion and, the elongate shaft comprising a commissure control element and an elbow control element, wherein the commissure control element and elbow control element are disposed inside the capsule, wherein the at least one elbow is coupled to the elbow control element, and the at least one commissure tab is coupled to the commissure control element, and wherein actuation of the distal portion of the delivery system is configured to separate the proximal portion of the capsule away from the distal portion of the capsule, thereby removing a constraint therefrom.

Example 29 is the system of any of Examples 21-28, wherein the actuation of the distal portion of the delivery system is configured to deploy the at least one commissure tab and separate the at least one commissure tab from the commissure control element, and wherein the separation is configured to allow the distal portion of the delivery system to expand.

Example 30 is the system of any of Examples 21-29, wherein actuation of the distal portion of the delivery system is configured to deploy the at least one elbow from the elbow control element and wherein the deployment of the at least one commissure tab from the commissure control element occurs simultaneously.

Example 31 is the system of any of Examples 21-30, wherein actuation of the distal portion of the delivery system is configured to deploy the at least one elbow from the elbow control element before the deployment of the at least one commissure tab from the commissure control element, or wherein the deployment of the at least one commissure tab from the commissure control element occurs before the deployment of the at least one elbow from the elbow control element.

Example 32 is the system of any of Examples 21-31, wherein the commissure control element further comprises slots, or wherein the elbow control element further comprises slots, and wherein the distal portion of the ventricular portion comprises protrusions disposed in the slots, wherein actuation of the distal portion of the delivery system is configured to separate the protrusions from the commissure control element or the elbow control element, and wherein the separation is configured to allow the ventricular portion to expand.

In Example 33, the apparatuses or method of any one or any combination of Examples 1-32 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method of delivering a prosthetic valve to a native mitral valve of patient's heart, the native mitral valve having a native anterior leaflet and a native posterior leaflet, the method comprising:

providing the prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange;

providing a delivery system wherein the prosthetic valve is coupled to a distal portion of the delivery system;

actuating the distal portion of the delivery system thereby removing a constraint from the prosthetic valve;

radially expanding the ventricular portion first; and radially expanding the atrial portion after the ventricular portion;

wherein the anterior anchoring tab and posterior anchoring tab each comprise at least one elbow, wherein the prosthetic valve further comprises at least one commissure tab, and wherein the distal portion of the delivery system further comprises a capsule and an elongate shaft, the capsule comprising a distal capsule portion and a proximal capsule portion and, the elongate shaft comprising a commissure control element and an elbow control element, wherein the commissure control element and elbow control element are disposed inside the capsule, wherein the at least one elbow is coupled to the elbow control element, and the at least one commissure tab is coupled to the commissure control element, and wherein actuating the distal portion of the delivery system comprises moving the proximal capsule portion of the capsule away from the distal portion of the capsule, thereby unconstraining the commissure control element and the elbow control element.

2. The method of claim 1, wherein actuating the distal portion of the delivery system comprises moving the proximal capsule portion away from the distal capsule portion.

3. The method of claim 2, wherein the delivery system further comprises an elongate shaft coupled to the distal capsule portion, and wherein moving the elongate shaft distally moves the distal capsule portion thereby unconstraining the ventricular portion.

4. The method of claim 2, wherein the distal capsule portion further comprises a straight edge along a proximal edge of the distal capsule portion, and wherein moving the distal portion of the capsule deploys the anterior anchoring tab and posterior anchoring tab simultaneously.

5. The method of claim 2, wherein the distal capsule portion further comprises an elongate shaft, wherein the elongate shaft has a longitudinal axis, and wherein a proximal edge of the distal capsule portion is transverse to the longitudinal axis, wherein moving the distal capsule portion of the capsule deploys the anterior anchoring tab before the posterior anchoring tab, or wherein moving the distal capsule portion of the capsule deploys the posterior anchoring tab before the anterior anchoring tab.

6. The method of claim 2, wherein the distal capsule portion further comprises an undulating or corrugated edge along a proximal edge of the distal capsule portion, wherein moving the distal portion of the capsule deploys the anterior anchoring tab before the ventricular skirt and the posterior anchoring tab, or wherein moving the distal portion of the capsule deploys the posterior anchoring tab before the ventricular skirt and the anterior anchoring tab.

7. The method of claim 1, wherein the distal portion of the delivery system further comprises a slotted region, wherein the slotted region is axially oriented, and wherein actuating the distal portion of the delivery system aligns a portion of the ventricular portion into the slotted region thereby removing a constraint from the ventricular portion and allowing radial expansion of the ventricular portion.

8. The method of claim 1, wherein actuating the distal portion of the delivery system comprises deploying the at least one commissure tab, wherein separating the commissure tab from the commissure control element allows radial expansion thereof.

9. The method of claim 1, wherein actuating the distal portion of the delivery system comprises releasing the at least one elbow from the elbow control element and releasing the at least one commissure tab from the commissure control element simultaneously.

10. The method of claim 1, wherein actuating the distal portion of the delivery system comprises releasing the at least one elbow from the elbow control element before releasing the at least one commissure tab from the commissure control element, or releasing the at least one commissure tab from the commissure control element before releasing the at least one elbow from the elbow control element.

11. The method of claim 1, wherein the commissure control element further comprises slots, or wherein the elbow control element further comprises slots, and wherein the distal portion of the ventricular portion comprises protrusions disposed in the slots, wherein actuating the distal portion of the delivery system comprises separating the protrusions from the commissure control element or the elbow control element, and wherein the separation allows the ventricular portion to expand.

12. A system for delivering a prosthetic valve to a native mitral valve of patient's heart, the native mitral valve having a native anterior leaflet and a native posterior leaflet, the system comprising:

a prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange; and a delivery system wherein the prosthetic valve is coupled to a distal portion of the delivery system, wherein actuation of the distal portion of the delivery system unconstrains the prosthetic valve, to allow radial expansion of the ventricular portion first, and radial expansion of the atrial portion after the ventricular portion;

wherein the anterior anchoring tab and posterior anchoring tab each comprise at least one elbow, wherein the prosthetic valve further comprises at least one commissure tab, the distal portion of the delivery system further comprises a capsule and an elongate shaft, the capsule comprising a distal capsule portion and a proximal capsule portion and, the elongate shaft comprising a commissure control element and an elbow control element, wherein the commissure control element and elbow control element are disposed inside the capsule, wherein the at least one elbow is coupled to the elbow control element, and the at least one commissure tab is coupled to the commissure control element, and wherein actuation of the distal portion of the delivery system is configured to separate the proximal capsule portion of the capsule away from the distal capsule portion of the capsule, thereby removing a constraint therefrom.

13. The system of claim 12, wherein actuation of the distal portion of the delivery system is configured to move the proximal capsule portion away from the distal capsule portion.

14. The system of claim 13, wherein the delivery system further comprises an elongate shaft coupled to the distal capsule portion, and wherein distal movement of the elongate shaft moves the distal capsule portion relative to the proximal capsule portion, and wherein the distal movement of the distal capsule portion is configured to unconstrain the ventricular portion.

15. The system of claim 13, wherein the distal capsule portion further comprises a straight edge along a proximal edge of the distal capsule portion, wherein movement of the distal portion of the capsule is configured to deploy the anterior anchoring tab and posterior anchoring tab simultaneously.

16. The system of claim 13, wherein the distal portion of the capsule further comprises an elongate shaft, wherein the elongate shaft has a longitudinal axis, wherein movement of the distal portion of the capsule is configured to deploy the anterior anchoring tab before the posterior anchoring tab, or wherein the movement of the distal portion of the capsule is configured to deploy the posterior anchoring tab before the anterior anchoring tab.

17. The system of claim 13, wherein the distal capsule portion further comprises an undulating or corrugated edge along a proximal edge of the distal capsule portion, wherein movement of the distal portion of the capsule is configured to deploy the anterior anchoring tab before the ventricular skirt and the posterior anchoring tab, or wherein the movement of the distal capsule portion is configured to deploy the posterior anchoring tab before the ventricular skirt and the posterior anchoring tab.

18. The system of claim 12, wherein the distal portion of the delivery system further comprises a slotted region, wherein the slotted region is axially oriented, and wherein the actuation of the distal portion of the delivery system is configured to align a portion of the ventricular portion into the slotted region thereby removing a constraint from the ventricular portion and allowing radial expansion of the ventricular portion.

19. The system of claim 12, wherein the actuation of the distal portion of the delivery system is configured to deploy the at least one commissure tab and separate the at least one commissure tab from the commissure control element, and wherein the separation is configured to allow the distal portion of the delivery system to expand.

20. The system of claim 12, wherein actuation of the distal portion of the delivery system is configured to deploy the at least one elbow from the elbow control element and wherein the deployment of the at least one commissure tab from the commissure control element occurs simultaneously.

21. The system of claim 12, wherein actuation of the distal portion of the delivery system is configured to deploy the at least one elbow from the elbow control element before the deployment of the at least one commissure tab from the commissure control element, or wherein the deployment of the at least one commissure tab from the commissure control element occurs before the deployment of the at least one elbow from the elbow control element.

22. The system of claim 12, wherein the commissure control element further comprises slots, or wherein the elbow control element further comprises slots, and wherein the distal portion of the ventricular portion comprises protrusions disposed in the slots, wherein actuation of the distal portion of the delivery system is configured to separate the protrusions from the commissure control element or the elbow control element, and wherein the separation is configured to allow the ventricular portion to expand.

23. A method of delivering a prosthetic valve to a native mitral valve of patient's heart, the native mitral valve having a native anterior leaflet and a native posterior leaflet, the method comprising:

providing the prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange;

providing a delivery system comprising an elongate shaft and a capsule comprising a distal capsule portion connected to the elongate shaft and a proximal capsule portion, wherein the prosthetic valve is coupled to a distal portion of the elongate shaft of the delivery system;

actuating the distal portion of the delivery system to move the distal capsule portion distally thereby removing a constraint from the prosthetic valve;

radially expanding the ventricular portion first; and radially expanding the atrial portion after the ventricular portion;

wherein the distal portion of the delivery system further comprises a slot, wherein the slot is axially oriented, and wherein actuating the distal portion of the delivery system aligns a portion of the ventricular portion into the slot thereby removing a constraint therefrom and allowing radial expansion thereof.

24. The method of claim 23, wherein the distal capsule portion further comprises a straight edge along a proximal edge of the distal capsule portion, and wherein moving the distal portion of the capsule deploys the anterior anchoring tab and posterior anchoring tab simultaneously.

25. The method of claim 23, wherein the elongate shaft has a longitudinal axis, and wherein a proximal edge of the distal capsule portion is transverse to the longitudinal axis, wherein moving the distal capsule portion of the capsule deploys the anterior anchoring tab before the posterior anchoring tab, or wherein moving the distal capsule portion of the capsule deploys the posterior anchoring tab before the anterior anchoring tab.

26. The method of claim 23, wherein the distal capsule portion further comprises an undulating or corrugated edge along a proximal edge of the distal capsule portion, wherein moving the distal portion of the capsule deploys the anterior anchoring tab before the ventricular skirt and the posterior anchoring tab, or wherein moving the distal portion of the capsule deploys the posterior anchoring tab before the ventricular skirt and the anterior anchoring tab.

27. A system for delivering a prosthetic valve to a native mitral valve of patient's heart, the native mitral valve having a native anterior leaflet and a native posterior leaflet, the system comprising:

a prosthetic valve comprising a ventricular portion and an atrial portion, wherein the ventricular portion comprises a ventricular skirt, an anterior anchoring tab disposed on the ventricular skirt, a posterior anchoring tab disposed on the ventricular skirt, and wherein the atrial portion comprises an atrial flange; and a delivery system comprising:

an elongate shaft; and a capsule comprising:

a distal capsule portion connected to the elongate shaft; and a proximal capsule portion:

wherein the prosthetic valve is coupled to a distal portion of the delivery system, wherein actuation of the distal portion of the delivery system unconstrains the prosthetic valve, to allow radial expansion of the ventricular portion first, and radial expansion of the atrial portion after the ventricular portion;

wherein the distal portion of the delivery system further comprises a slot, wherein the slot is axially oriented, and wherein the actuation of the distal portion of the delivery system is configured to align a portion of the ventricular portion into the slot thereby, removing a constraint therefrom and allowing radial expansion thereof.

28. The system of claim 27, wherein the distal capsule portion further comprises a straight edge along a proximal edge of the distal capsule portion, wherein movement of the distal portion of the capsule is configured to deploy the anterior anchoring tab and posterior anchoring tab simultaneously.

29. The system of claim 27, wherein the elongate shaft has a longitudinal axis, wherein movement of the distal portion of the capsule is configured to deploy the anterior anchoring tab before the posterior anchoring tab, or wherein the movement of the distal portion of the capsule is configured to deploy the posterior anchoring tab before the anterior anchoring tab.

30. The system of claim 27, wherein the distal capsule portion further comprises an undulating or corrugated edge along a proximal edge of the distal capsule portion, wherein distal movement of the distal portion of the capsule is configured to deploy the anterior anchoring tab before the ventricular skirt and the posterior anchoring tab, or wherein the distal movement of the distal capsule portion is configured to deploy the posterior anchoring tab before the ventricular skirt and the posterior anchoring tab.

* * * * *